United States Patent
Rafiee

(10) Patent No.: US 10,321,998 B2
(45) Date of Patent: Jun. 18, 2019

(54) METHODS AND SYSTEMS FOR DELIVERING PROSTHESES USING RAIL TECHNIQUES

(71) Applicant: Nasser Rafiee, Andover, MA (US)

(72) Inventor: Nasser Rafiee, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 676 days.

(21) Appl. No.: 13/886,983

(22) Filed: May 3, 2013

(65) Prior Publication Data

US 2014/0163668 A1    Jun. 12, 2014

Related U.S. Application Data

(63) Continuation-in-part of application No. PCT/US2011/059586, filed on Nov. 7, 2011, which is
(Continued)

(51) Int. Cl.
*A61F 2/24* (2006.01)
*A61B 17/04* (2006.01)

(52) U.S. Cl.
CPC .......... *A61F 2/2439* (2013.01); *A61F 2/2418* (2013.01); *A61B 17/0487* (2013.01);
(Continued)

(58) Field of Classification Search
CPC .... A61F 2/2454; A61F 2/2439; A61F 2/2436; A61F 2/2409; A61F 2/2466;
(Continued)

(56) References Cited

U.S. PATENT DOCUMENTS 4,106,129 A    8/1978    Carpentier et al.
4,259,753 A    4/1981    Liotta et al.
(Continued)

FOREIGN PATENT DOCUMENTS

EP    2412397 A1    2/2012
RU    100 718 U1    12/2010
(Continued)

OTHER PUBLICATIONS

Patent Examination Report issued in related Australian patent application No. 2013205892, dated Oct. 13, 2015.
(Continued)

*Primary Examiner* — David C Eastwood
*Assistant Examiner* — Erich Herbermann
(74) *Attorney, Agent, or Firm* — Crawford Maunu PLLC

(57) ABSTRACT

Exemplary embodiments provide methods and systems for delivering a prosthesis to a target location in a lumenal system of a patient. At least one tether is secured proximate the target location to serve as a rail, and a prosthesis is advanced along the rail to the target location and secured in place. Exemplary methods and systems provide for repair of the mitral and tricuspid valves, as well as abdominal aortic aneurysms, stomach valves, fallopian tubes and the pulmonary system, among others. Also disclosed are various prostheses suitable for use with the disclosed methods and systems.

10 Claims, 49 Drawing Sheets

Related U.S. Application Data a continuation-in-part of application No. 13/240,793, filed on Sep. 22, 2011, now abandoned.

(60) Provisional application No. 61/451,899, filed on Mar. 11, 2011, provisional application No. 61/431,384, filed on Jan. 10, 2011, provisional application No. 61/410,877, filed on Nov. 6, 2010, provisional application No. 61/385,843, filed on Sep. 23, 2010.

(52) U.S. Cl.
CPC . *A61B 2017/044* (2013.01); *A61B 2017/0417* (2013.01); *A61F 2/2436* (2013.01); *A61F 2/2457* (2013.01); *A61F 2220/0008* (2013.01); *A61F 2220/0016* (2013.01); *A61F 2230/0013* (2013.01); *A61F 2250/006* (2013.01)

(58) Field of Classification Search
CPC ...... A61F 2230/0133; A61F 2220/0016; A61F 17/08; A61F 17/122; A61F 2/24; A61F 2/95
USPC .............................. 606/157; 623/2.11, 1.26
See application file for complete search history.

(56) References Cited

U.S. PATENT DOCUMENTS

| | | |
|---|---|---|
| 4,666,442 A | 5/1987 | Arru et al. |
| 4,692,164 A | 9/1987 | Dzemeshkevich et al. |
| 5,411,552 A | 5/1995 | Andersen et al. |
| 5,449,384 A | 9/1995 | Johnson |
| 5,606,928 A | 3/1997 | Religa et al. |
| 5,788,715 A | 8/1998 | Watson, Jr. et al. |
| 5,861,028 A | 1/1999 | Angell |
| 5,895,410 A | 4/1999 | Forber et al. |
| 5,928,281 A | 7/1999 | Huynh et al. |
| 6,059,769 A | 5/2000 | Lunn et al. |
| 6,106,510 A | 8/2000 | Lunn et al. |
| 6,375,774 B1 | 4/2002 | Lunn et al. |
| 6,599,303 B1* | 7/2003 | Peterson ............ A61B 17/11 606/153 |
| 6,602,271 B2 | 8/2003 | Adams et al. |
| 6,716,231 B1 | 4/2004 | Rafiee et al. |
| 6,733,525 B2 | 5/2004 | Yang et al. |
| 6,790,229 B1* | 9/2004 | Berreklouw ......... A61B 17/11 606/153 |
| 6,797,000 B2 | 9/2004 | Simpson et al. |
| 6,800,081 B2 | 10/2004 | Parodi |
| 6,866,677 B2 | 3/2005 | Douk et al. |
| 6,893,459 B1* | 5/2005 | Macoviak ............ A61F 2/2403 623/2.11 |
| 6,911,036 B2 | 6/2005 | Douk et al. |
| 6,953,476 B1 | 10/2005 | Shalev |
| 6,960,217 B2 | 11/2005 | Bolduc |
| 7,044,958 B2 | 5/2006 | Douk et al. |
| 7,066,946 B2 | 6/2006 | Douk et al. |
| 7,189,259 B2 | 3/2007 | Simionescu et al. |
| 7,195,641 B2 | 3/2007 | Palmaz et al. |
| 7,201,772 B2 | 4/2007 | Schwammenthal et al. |
| 7,294,135 B2 | 11/2007 | Stephens et al. |
| 7,316,706 B2 | 1/2008 | Bloom et al. |
| 7,399,315 B2 | 7/2008 | Iobbi |
| 7,425,219 B2 | 9/2008 | Quadri |
| 7,442,204 B2 | 10/2008 | Schwammenthal et al. |
| 7,442,207 B2 | 10/2008 | Rafiee |
| 7,445,631 B2 | 11/2008 | Salahieh et al. |
| 7,481,838 B2 | 1/2009 | Carpentier et al. |
| 7,491,232 B2 | 2/2009 | Bolduc et al. |
| 7,524,330 B2 | 4/2009 | Berreklouw |
| 7,655,040 B2 | 2/2010 | Douk et al. |
| 7,682,352 B2 | 3/2010 | Rafiee et al. |
| 7,699,892 B2 | 4/2010 | Rafiee et al. |
| 7,716,801 B2 | 5/2010 | Douk et al. |
| 7,753,840 B2 | 7/2010 | Simionescu et al. |
| 7,753,949 B2 | 7/2010 | Lamphere et al. |
| 7,780,726 B2 | 8/2010 | Seguin |
| 7,799,069 B2 | 9/2010 | Bailey et al. |
| 7,806,917 B2 | 10/2010 | Xiao |
| 7,806,919 B2 | 10/2010 | Bloom et al. |
| 7,815,673 B2 | 10/2010 | Bloom et al. |
| 7,947,072 B2 | 5/2011 | Yang et al. |
| 7,955,384 B2 | 6/2011 | Rafiee et al. |
| 7,972,370 B2 | 7/2011 | Douk et al. |
| 7,998,188 B2 | 8/2011 | Zilla et al. |
| 8,002,825 B2 | 8/2011 | Letac et al. |
| 8,052,750 B2 | 11/2011 | Tuval et al. |
| 8,062,355 B2 | 11/2011 | Figulla et al. |
| 8,070,802 B2 | 12/2011 | Lamphere et al. |
| 8,092,518 B2 | 1/2012 | Schreck |
| 8,092,520 B2 | 1/2012 | Quadri |
| 8,092,524 B2 | 1/2012 | Nugent et al. |
| 8,226,710 B2 | 7/2012 | Nguyen et al. |
| 8,252,051 B2 | 8/2012 | Chau et al. |
| 8,308,798 B2 | 11/2012 | Pintor et al. |
| 8,337,541 B2 | 12/2012 | Quadri et al. |
| 8,348,995 B2 | 1/2013 | Tuval et al. |
| 8,348,996 B2 | 1/2013 | Tuval et al. |
| 8,353,954 B2 | 1/2013 | Cai et al. |
| 8,353,955 B2 | 1/2013 | Styrc et al. |
| 2001/0021872 A1 | 9/2001 | Bailey et al. |
| 2002/0032481 A1 | 3/2002 | Gabbay |
| 2002/0138138 A1 | 9/2002 | Yang |
| 2003/0055495 A1 | 3/2003 | Pease et al. |
| 2003/0065386 A1 | 4/2003 | Weadock |
| 2003/0097172 A1 | 5/2003 | Shalev et al. |
| 2004/0087998 A1 | 5/2004 | Lee et al. |
| 2004/0127916 A1 | 7/2004 | Bolduc et al. |
| 2004/0260317 A1 | 12/2004 | Bloom et al. |
| 2005/0038508 A1 | 2/2005 | Gabbay |
| 2005/0043790 A1 | 2/2005 | Seguin |
| 2005/0055082 A1 | 3/2005 | Ben-Muvhar et al. |
| 2005/0137769 A1 | 6/2005 | Salahieh et al. |
| 2005/0143809 A1 | 6/2005 | Salahieh et al. |
| 2005/0177180 A1 | 8/2005 | Kaganov et al. |
| 2005/0288706 A1 | 12/2005 | Widomski et al. |
| 2006/0085012 A1 | 4/2006 | Dolan |
| 2006/0106449 A1 | 5/2006 | Ben-Muvhar |
| 2006/0106450 A1 | 5/2006 | Ben-Muvhar |
| 2006/0173537 A1 | 8/2006 | Yang et al. |
| 2007/0016288 A1* | 1/2007 | Gurskis ............... A61F 2/2418 623/2.11 |
| 2007/0043435 A1 | 2/2007 | Seguin et al. |
| 2007/0067029 A1 | 3/2007 | Gabbay |
| 2007/0250160 A1 | 10/2007 | Rafiee |
| 2007/0255398 A1 | 11/2007 | Yang et al. |
| 2007/0260305 A1 | 11/2007 | Drews et al. |
| 2007/0288089 A1 | 12/2007 | Gurskis et al. |
| 2007/0293942 A1 | 12/2007 | Mizraee |
| 2008/0021537 A1 | 1/2008 | Ben-Muvhar et al. |
| 2008/0065191 A1 | 3/2008 | Bolduc et al. |
| 2008/0077234 A1 | 3/2008 | Styrc |
| 2008/0125860 A1 | 5/2008 | Webler et al. |
| 2008/0208328 A1 | 8/2008 | Antocci et al. |
| 2008/0221672 A1 | 9/2008 | Lamphere et al. |
| 2008/0281411 A1* | 11/2008 | Berreklouw ......... A61B 17/11 623/2.11 |
| 2009/0005863 A1 | 1/2009 | Goetz et al. |
| 2009/0062841 A1 | 3/2009 | Amplatz et al. |
| 2009/0149949 A1 | 6/2009 | Quinn |
| 2009/0270966 A1 | 10/2009 | Douk et al. |
| 2009/0270976 A1 | 10/2009 | Douk et al. |
| 2009/0306768 A1 | 12/2009 | Quadri |
| 2009/0319038 A1 | 12/2009 | Gurskis et al. |
| 2010/0036479 A1 | 2/2010 | Hill et al. |
| 2010/0082094 A1 | 4/2010 | Quadri et al. |
| 2010/0100167 A1 | 4/2010 | Bortlein et al. |
| 2010/0174363 A1 | 7/2010 | Castro |
| 2010/0179648 A1 | 7/2010 | Richter et al. |
| 2010/0179649 A1 | 7/2010 | Richter et al. |
| 2010/0185275 A1 | 7/2010 | Richter et al. |
| 2010/0249923 A1 | 9/2010 | Alkhatib et al. |
| 2010/0262232 A1 | 10/2010 | Annest |
| 2010/0280606 A1 | 11/2010 | Naor |

(56) References Cited

U.S. PATENT DOCUMENTS

| | | |
|---|---|---|
| 2010/0298931 A1 | 11/2010 | Quadri et al. |
| 2011/0112632 A1 | 5/2011 | Chau et al. |
| 2011/0137409 A1 | 6/2011 | Yang et al. |
| 2011/0172784 A1 | 7/2011 | Richter et al. |
| 2011/0282438 A1 | 11/2011 | Drews et al. |
| 2011/0313515 A1 | 12/2011 | Quadri et al. |
| 2011/0319988 A1 | 12/2011 | Schankereli et al. |
| 2011/0319989 A1 | 12/2011 | Lane et al. |
| 2012/0022639 A1* | 1/2012 | Hacohen .............. A61B 17/068 623/2.11 |
| 2012/0059450 A1 | 3/2012 | Chiang et al. |
| 2012/0078353 A1 | 3/2012 | Quadri et al. |
| 2012/0078360 A1 | 3/2012 | Rafiee |
| 2012/0179244 A1 | 7/2012 | Schankereli et al. |
| 2012/0215303 A1 | 8/2012 | Quadri et al. |
| 2012/0316642 A1 | 12/2012 | Yu et al. |
| 2012/0323316 A1 | 12/2012 | Chau et al. |
| 2014/0018906 A1 | 1/2014 | Rafiee |
| 2014/0039083 A1 | 2/2014 | Rafiee |
| 2014/0128965 A1 | 5/2014 | Rafiee |
| 2014/0163668 A1 | 6/2014 | Rafiee |
| 2014/0358223 A1 | 12/2014 | Rafiee et al. |

FOREIGN PATENT DOCUMENTS

| | | |
|---|---|---|
| WO | WO2007121314 A2 | 10/2007 |
| WO | 2012/061809 A2 | 5/2012 |
| WO | WO2013131069 A1 | 9/2013 |
| WO | WO2015069947 A1 | 5/2015 |
| WO | WO2015148821 A1 | 10/2015 |

OTHER PUBLICATIONS

USPTO's Non-Final Office Action issued in related U.S. Appl. No. 13/887,043, dated Jun. 5, 2015.
International Search Report, for related application No. PCT/US2011/059586, dated May 25, 2012.
International Preliminary Report on Patentability and Written Opinion, or related application No. PCT/US2011/059586, dated May 25, 2012.
BioIntegral Surgical, Mitral Valve Restoration System, 2009.
International Search Report for co-pending international application No. PCT/US2013/028774, dated Jun. 14, 2013.
International Preliminary Report on Patentability and Written Opinion, on related application No. PCT/US2014/064431 dated Mar. 26, 2015.
International Search Report, for related application No. PCT/US2015/022782, dated Jun. 18, 2015.

* cited by examiner

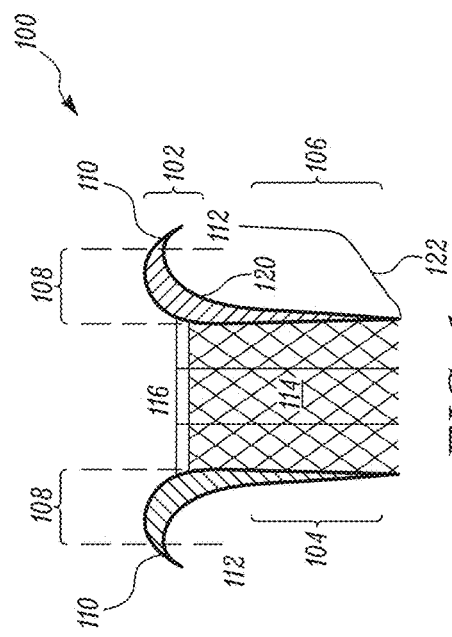
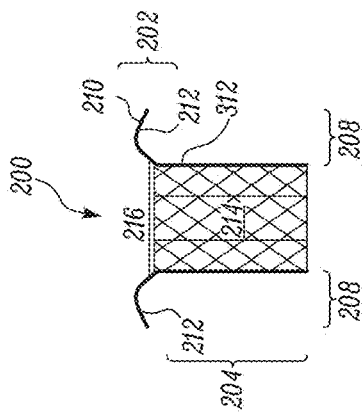
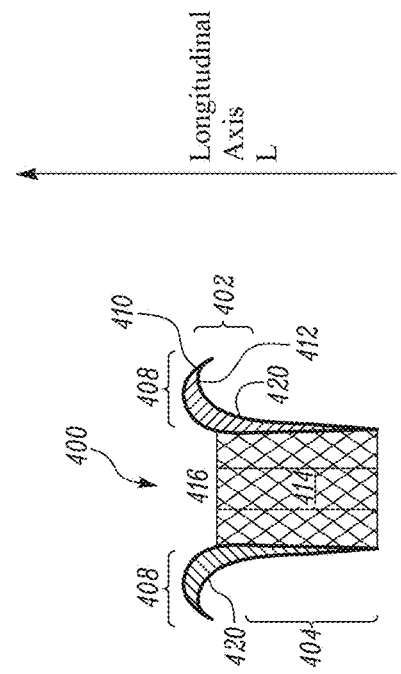
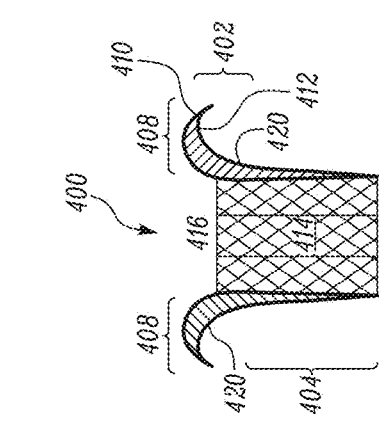

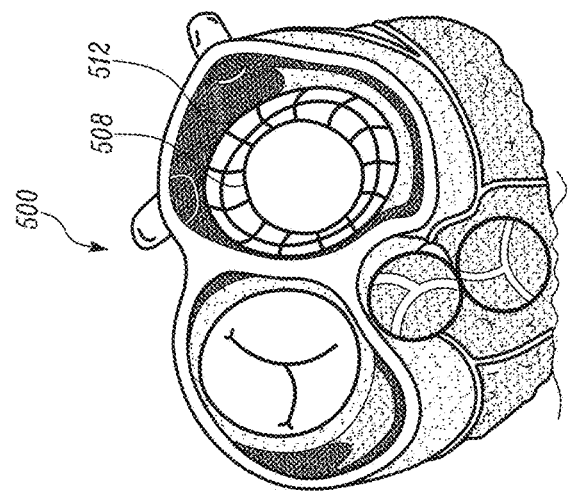
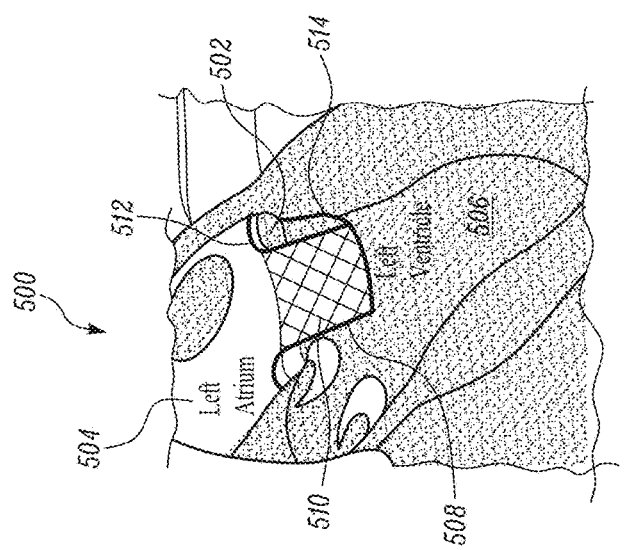
FIG. 5B
FIG. 5A

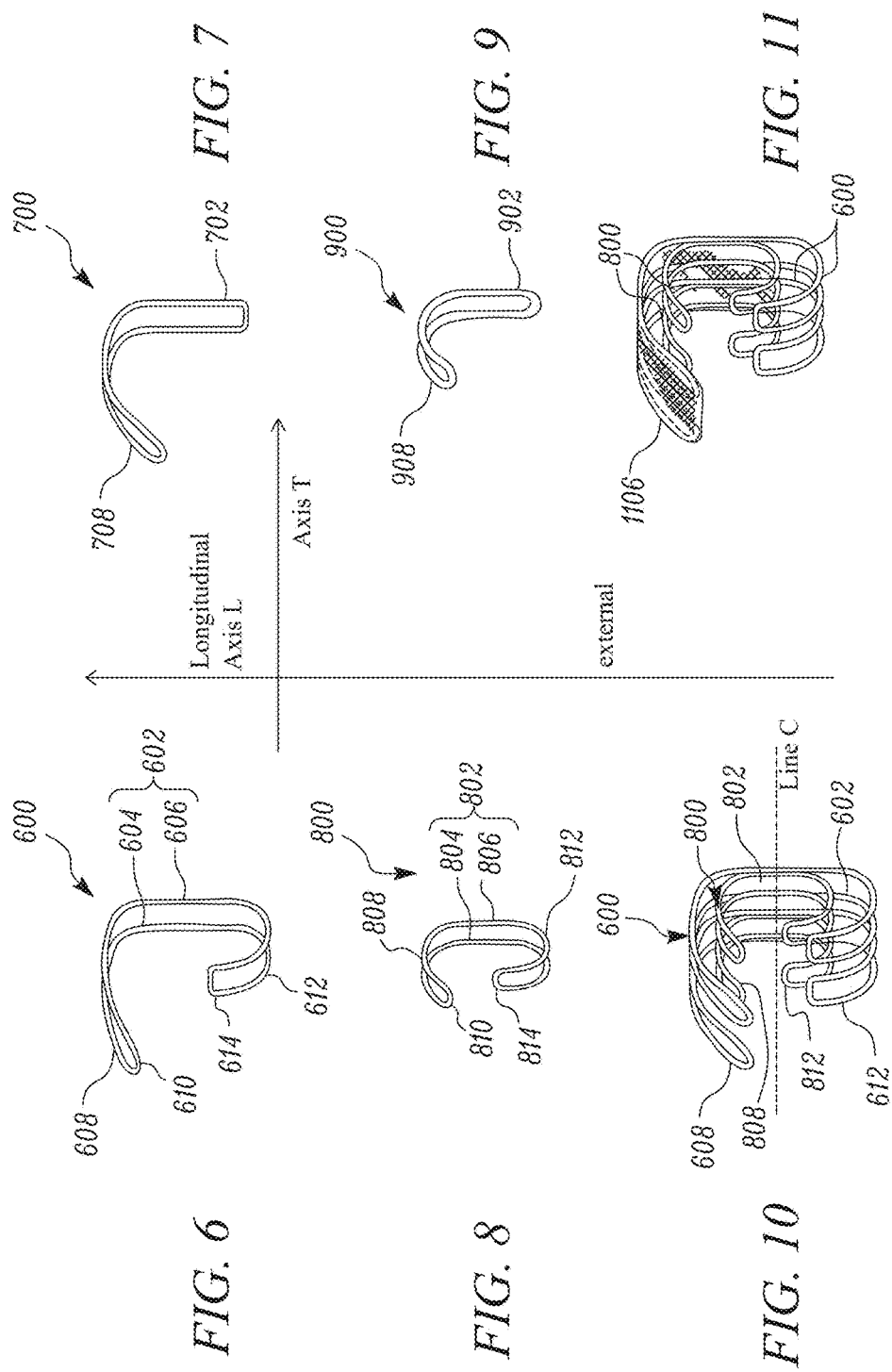

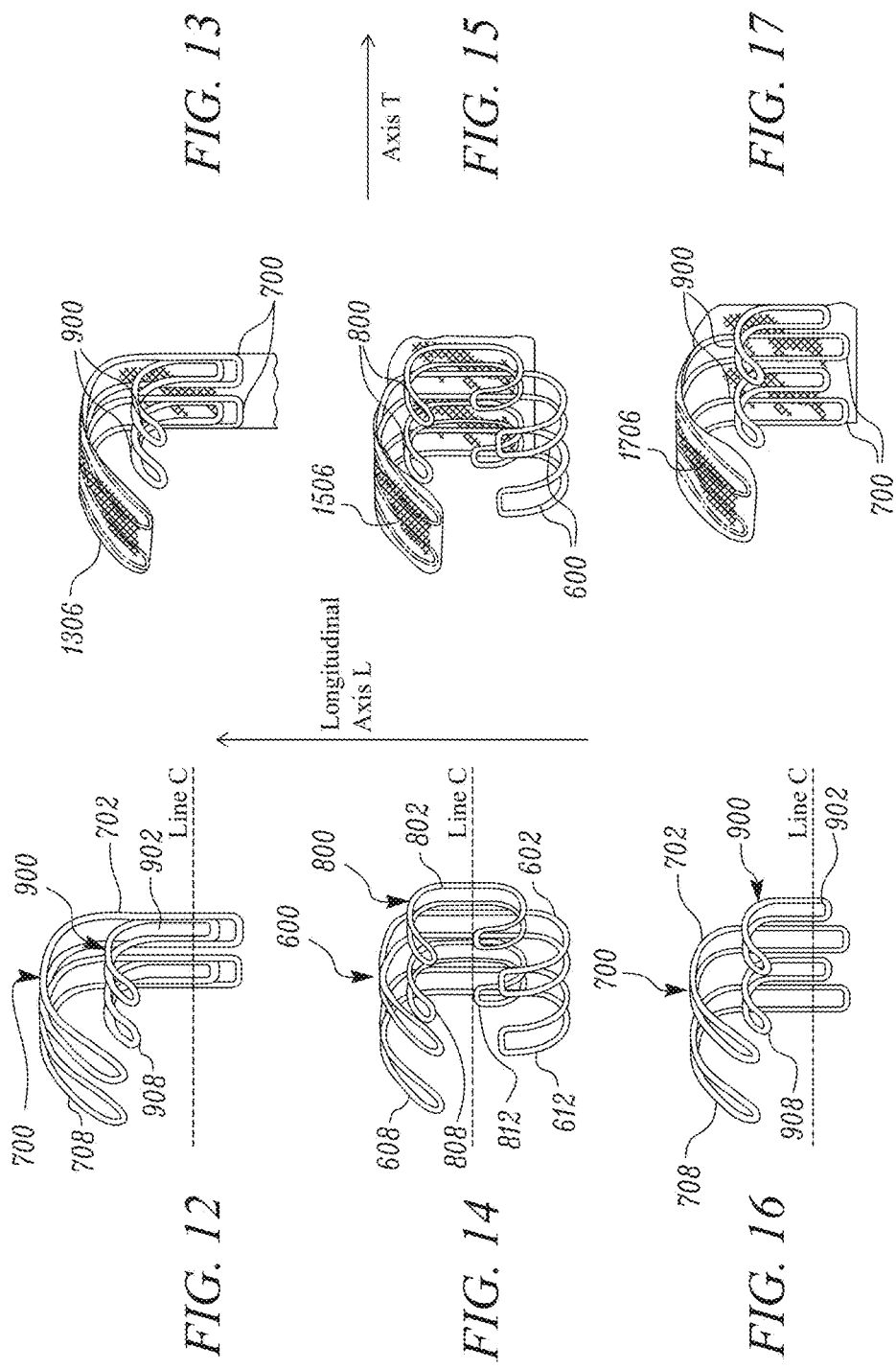

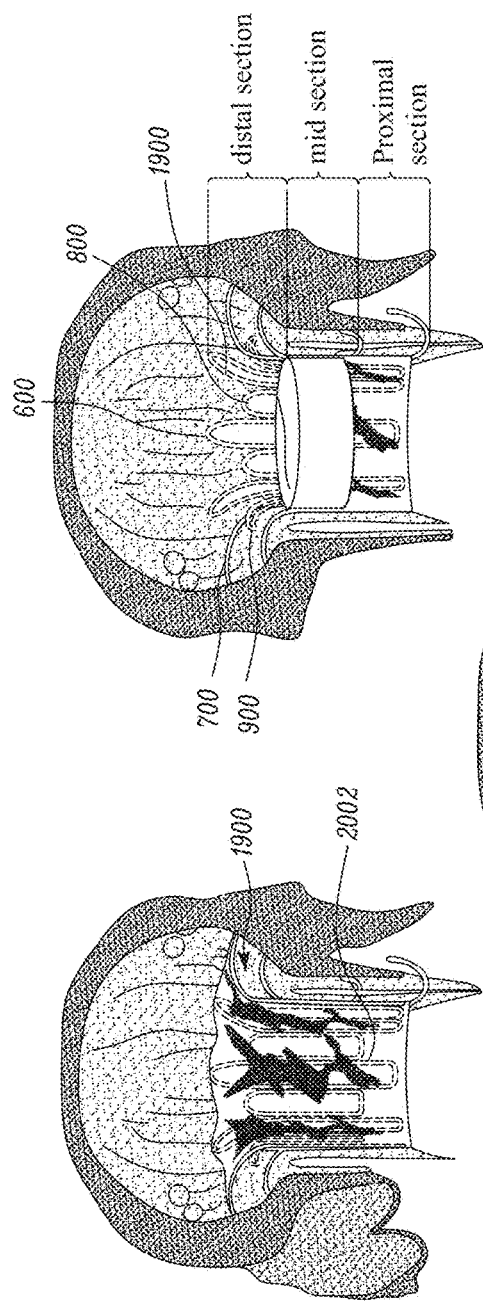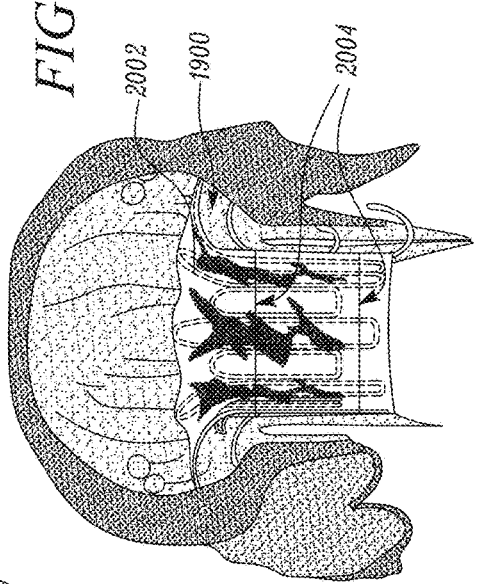

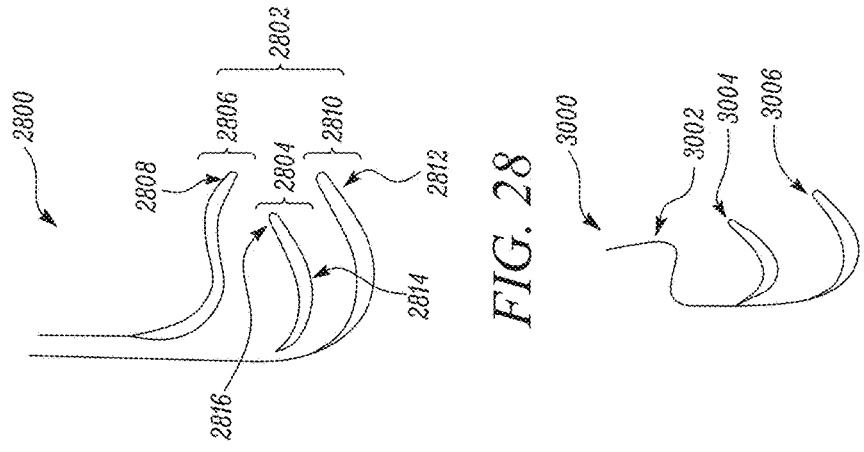
FIG. 28
FIG. 30
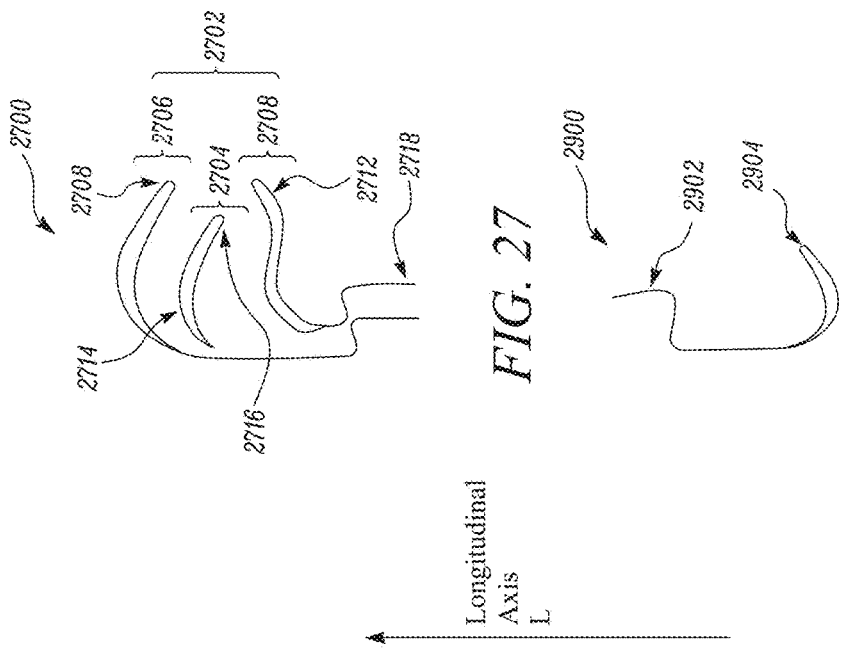
FIG. 27
FIG. 29
Longitudinal Axis L

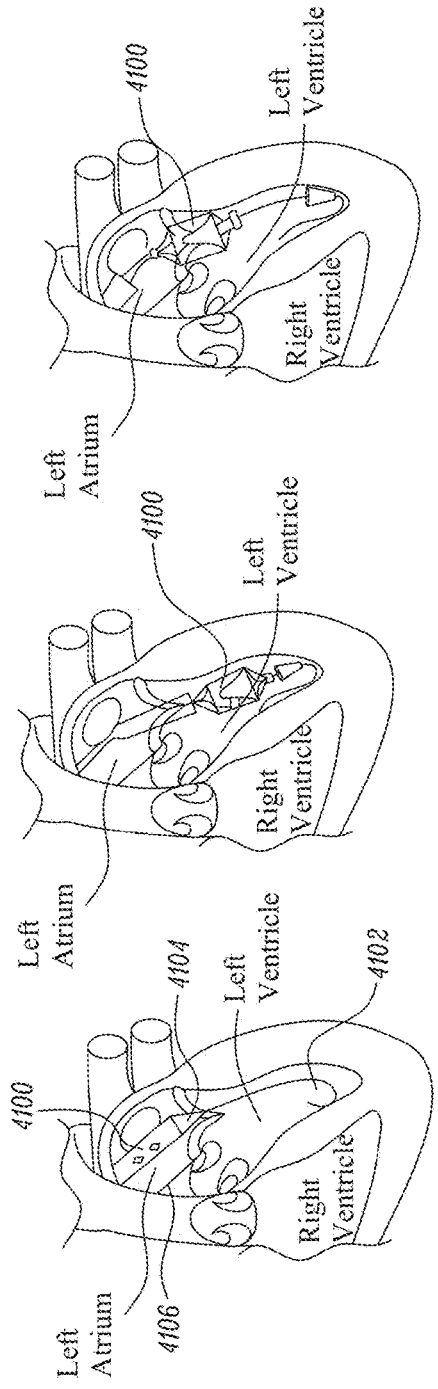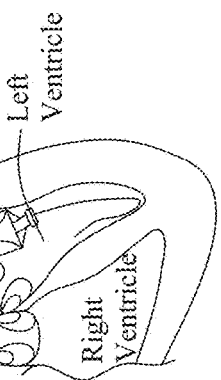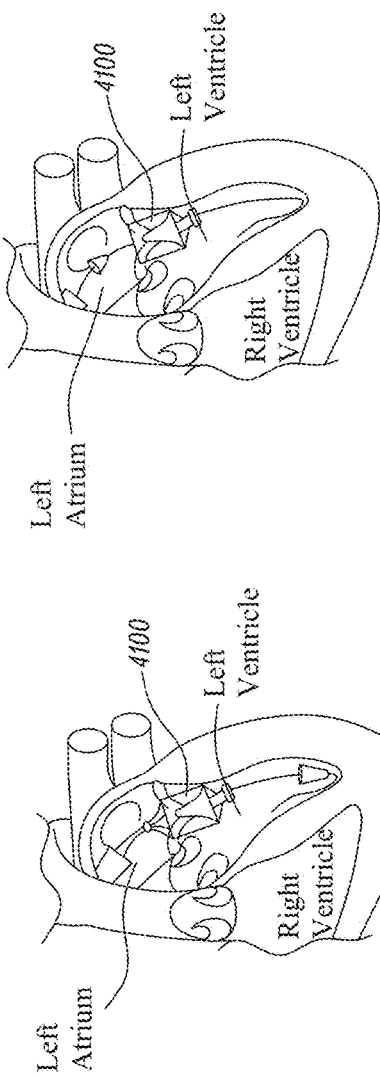
FIG. 47A  FIG. 47B  FIG. 47C
FIG. 47D  FIG. 47E

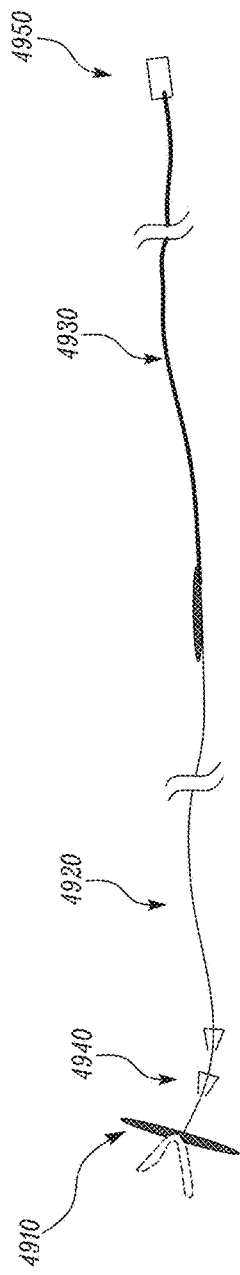
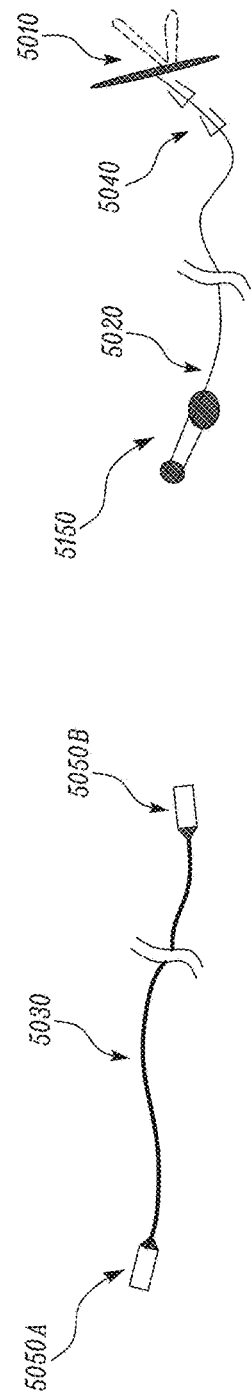

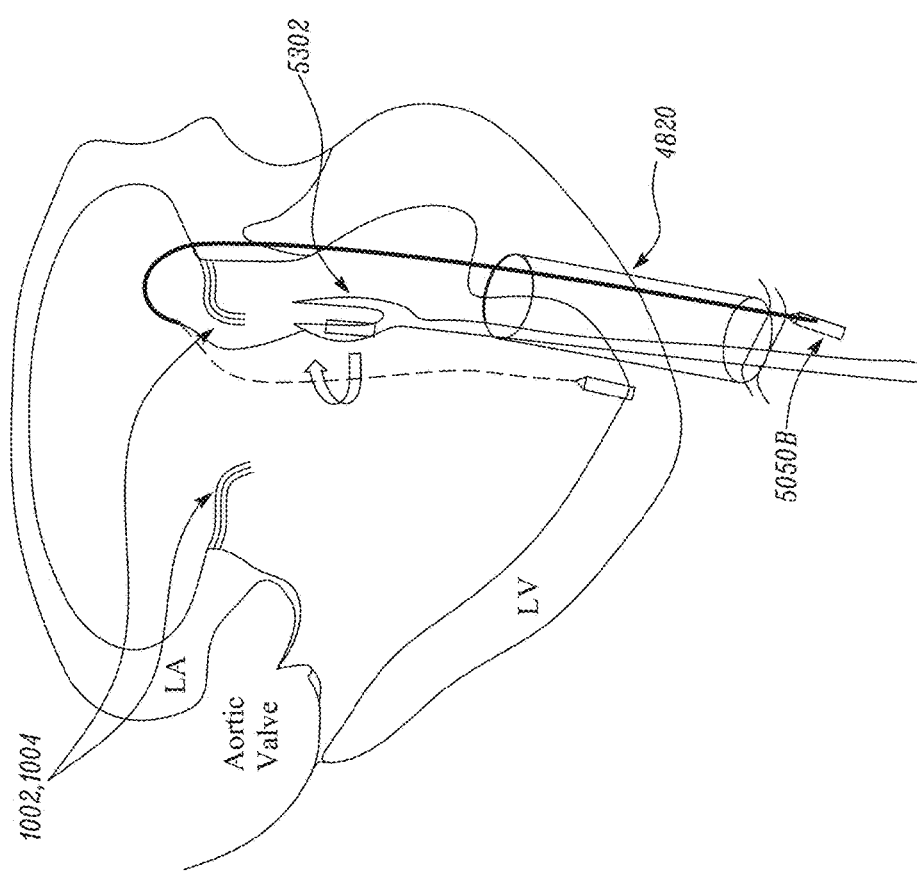

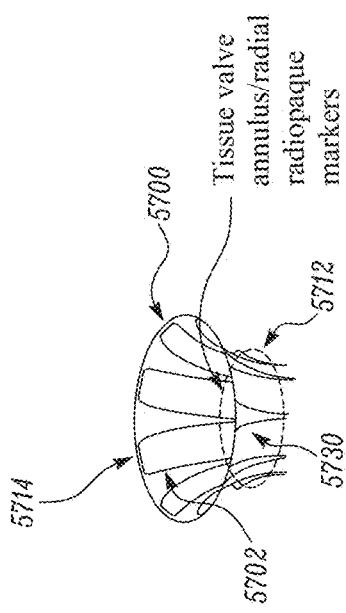
FIG. 57A
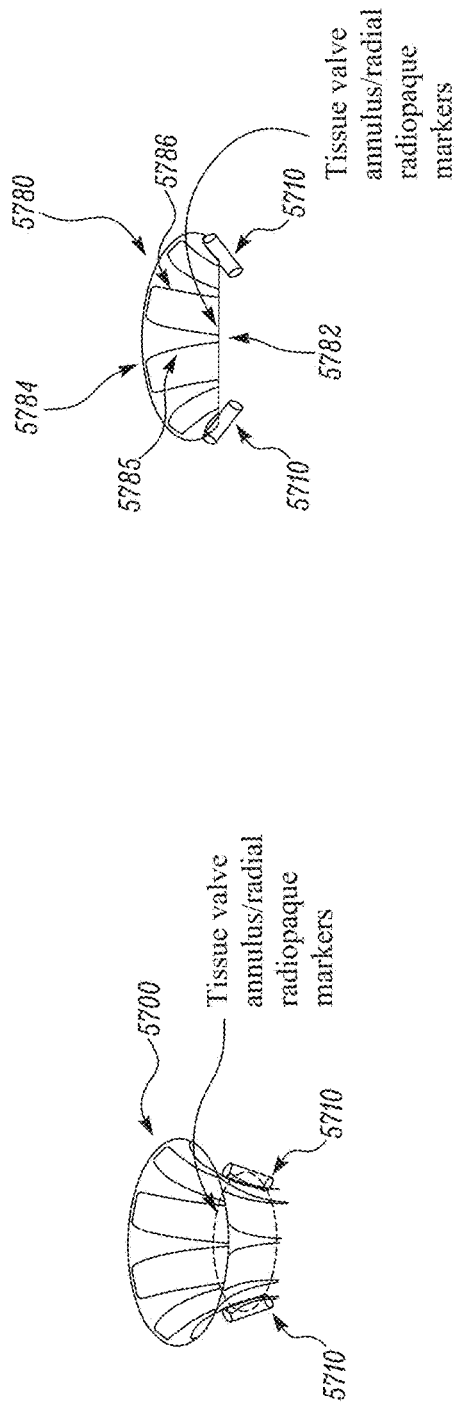
FIG. 57C
FIG. 57B

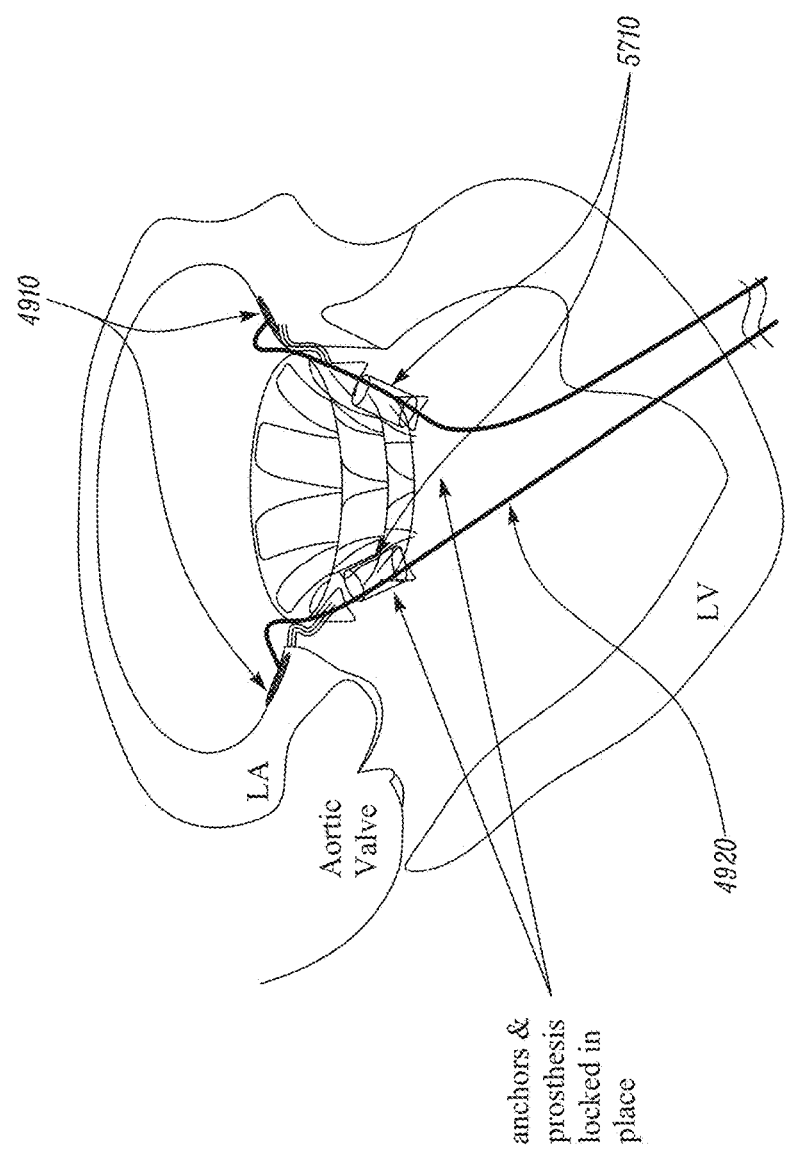

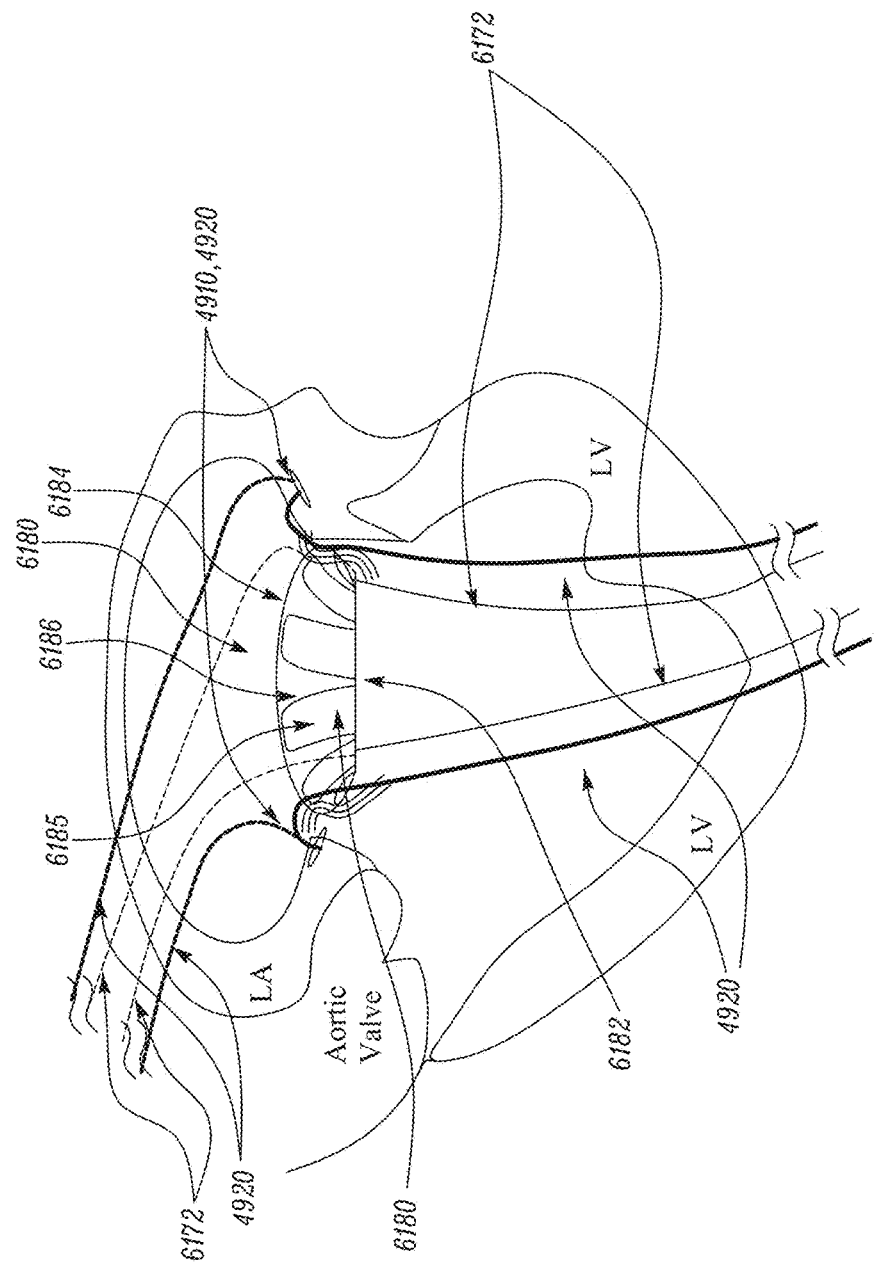

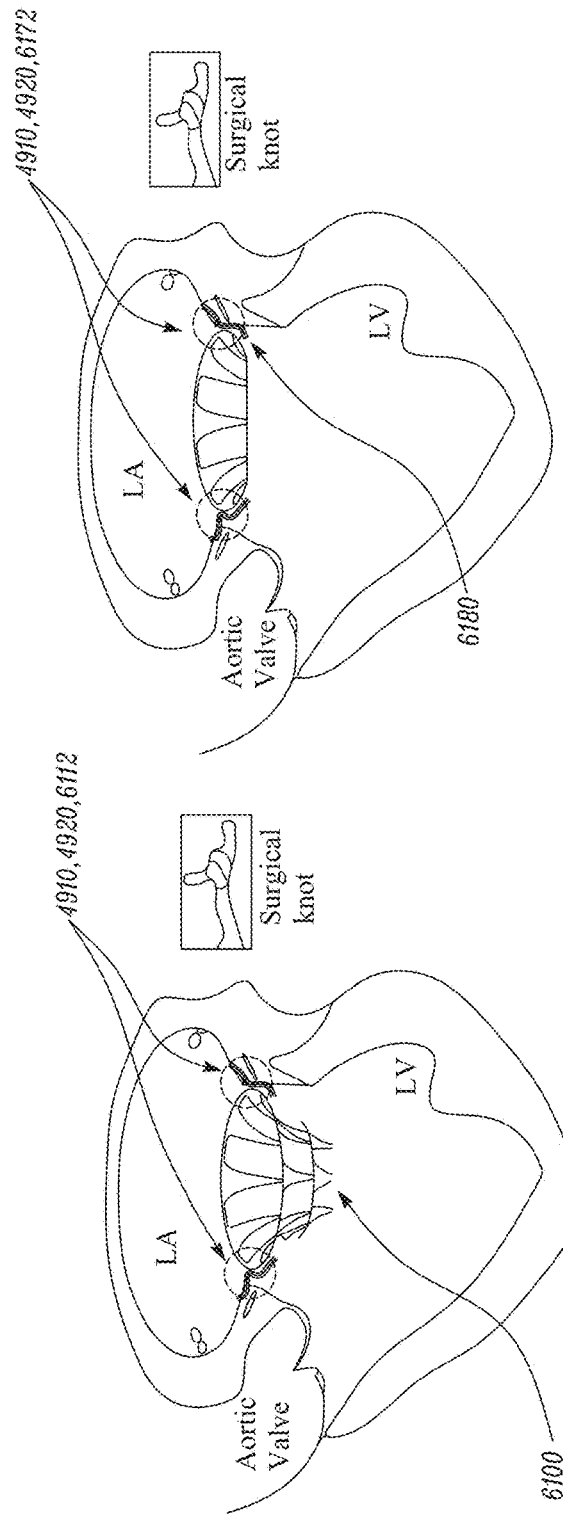

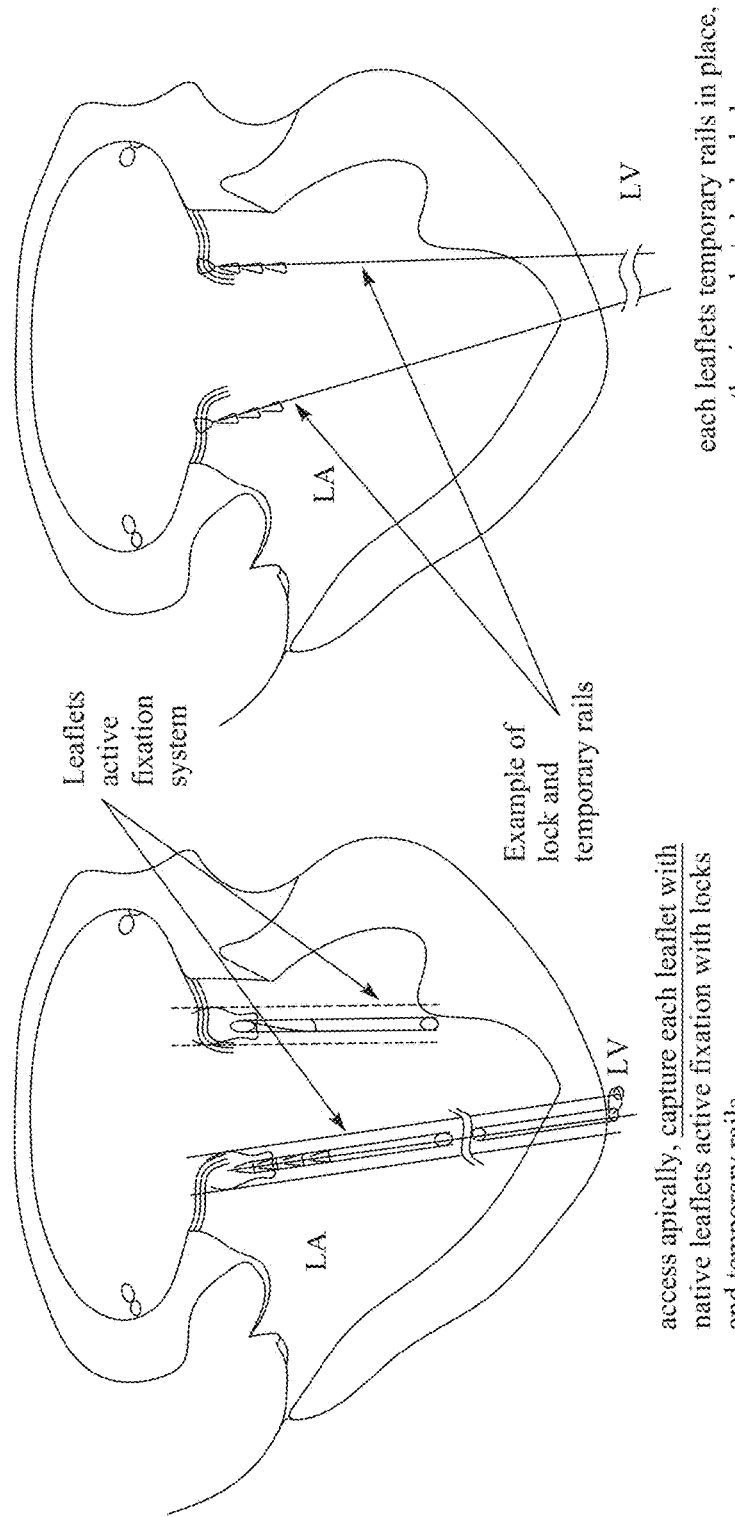

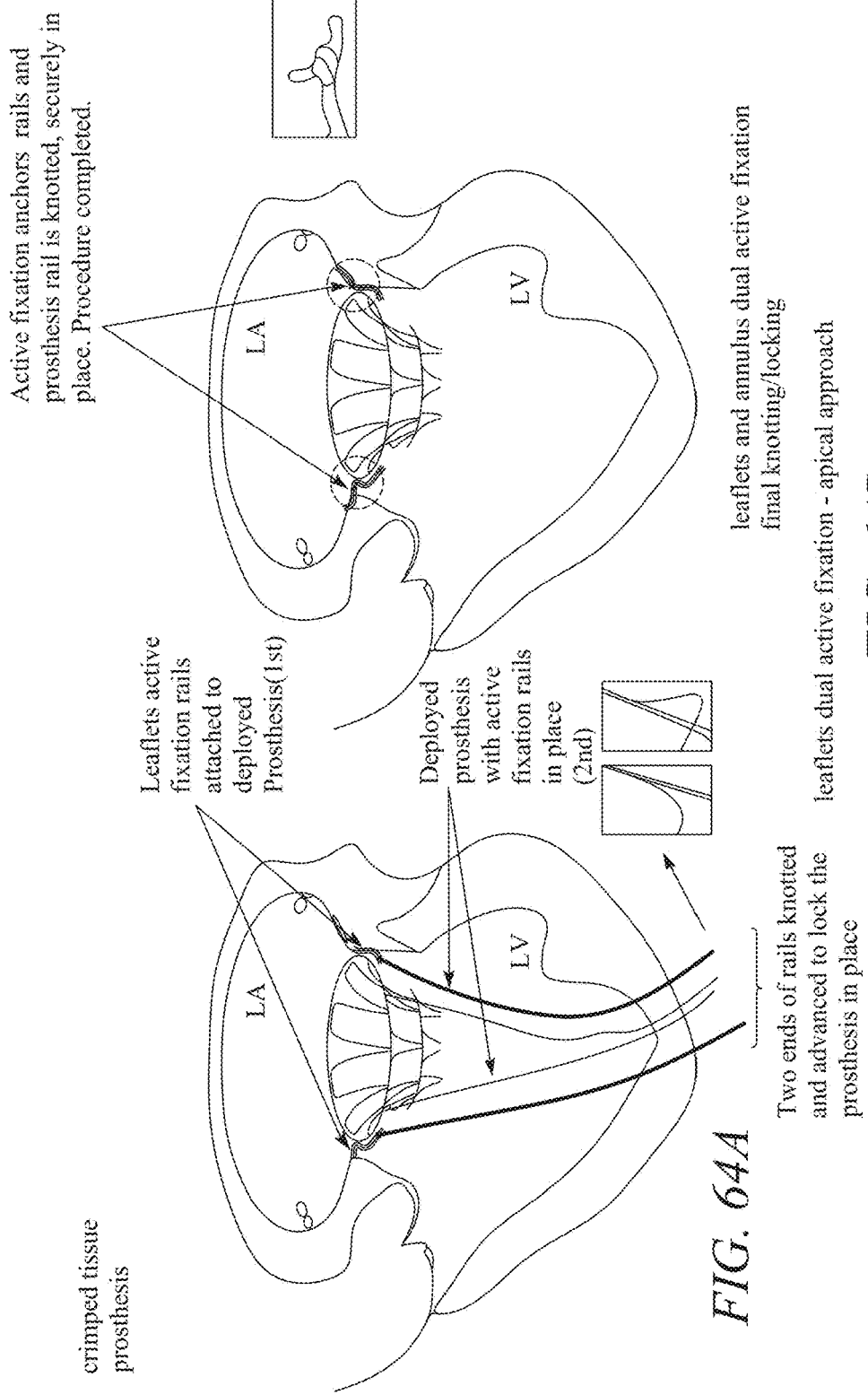

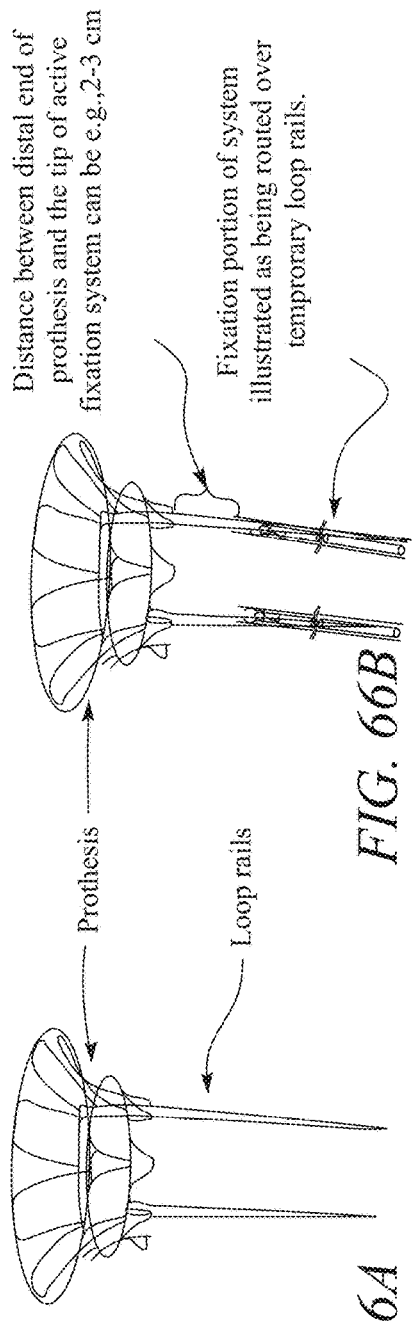
FIG. 66A
FIG. 66B
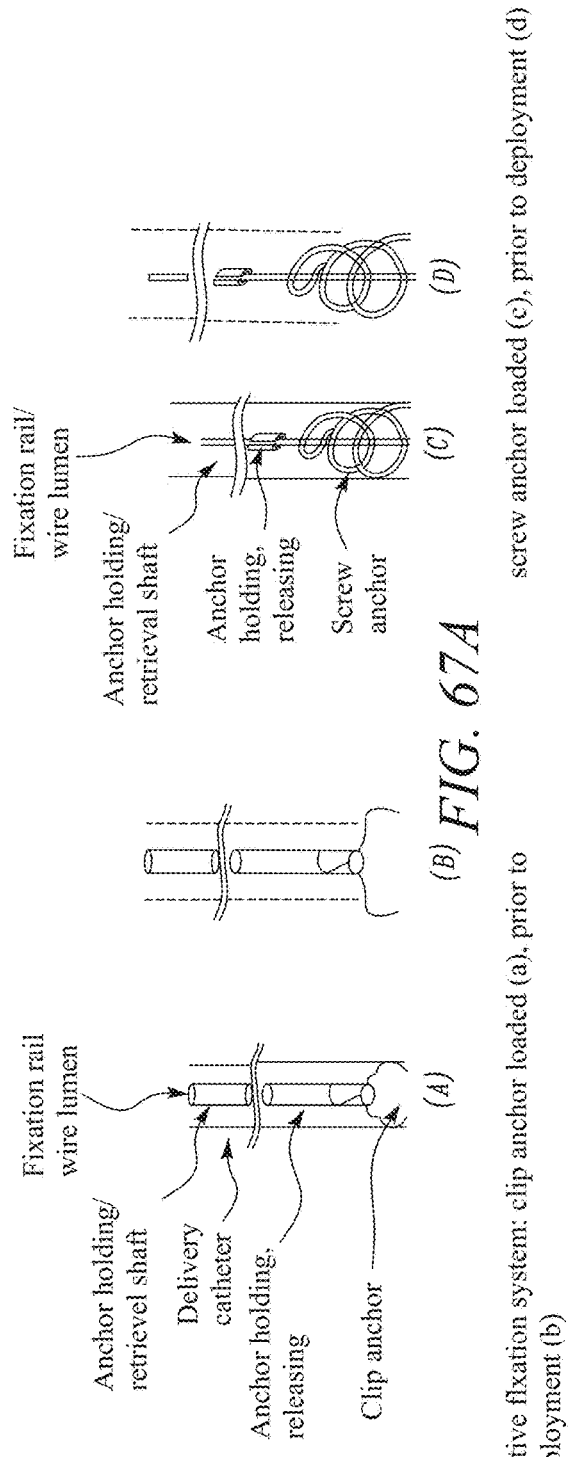
FIG. 67A
Active fixation system: clip anchor loaded (a), prior to deployment (b) screw anchor loaded (c), prior to deployment (d)

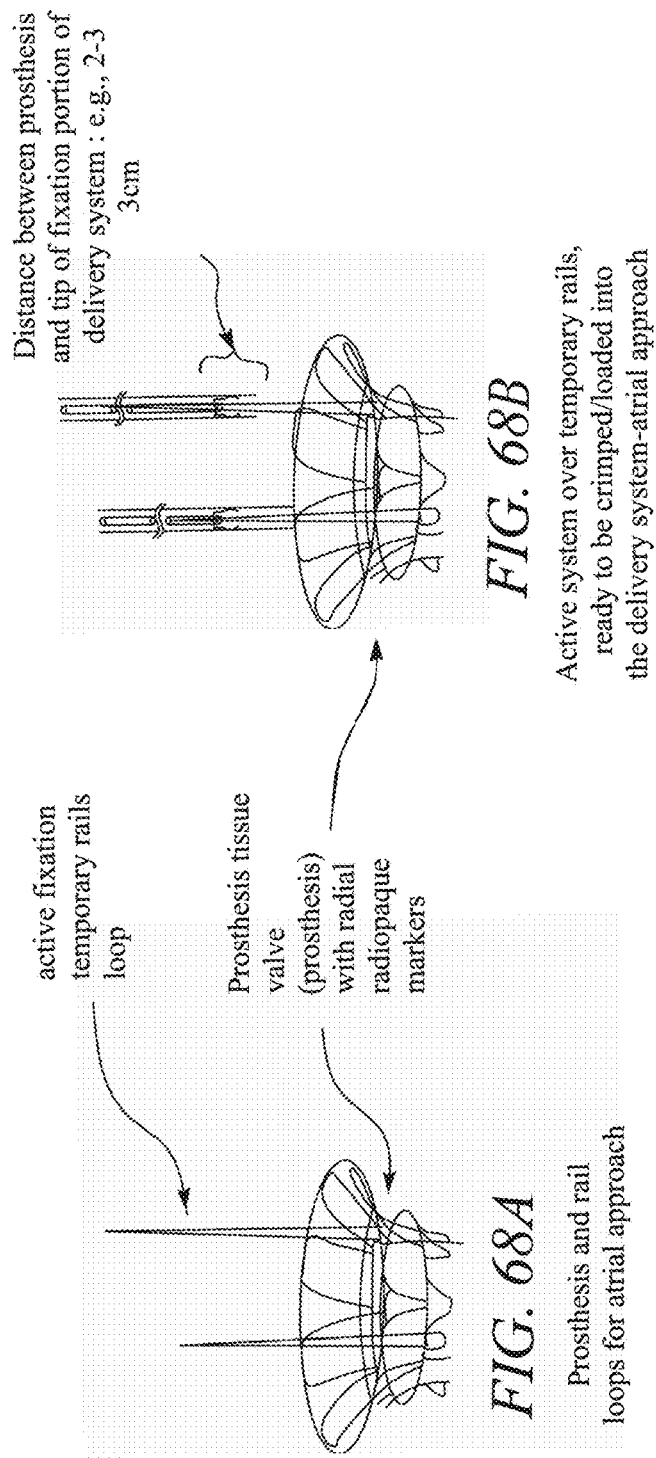

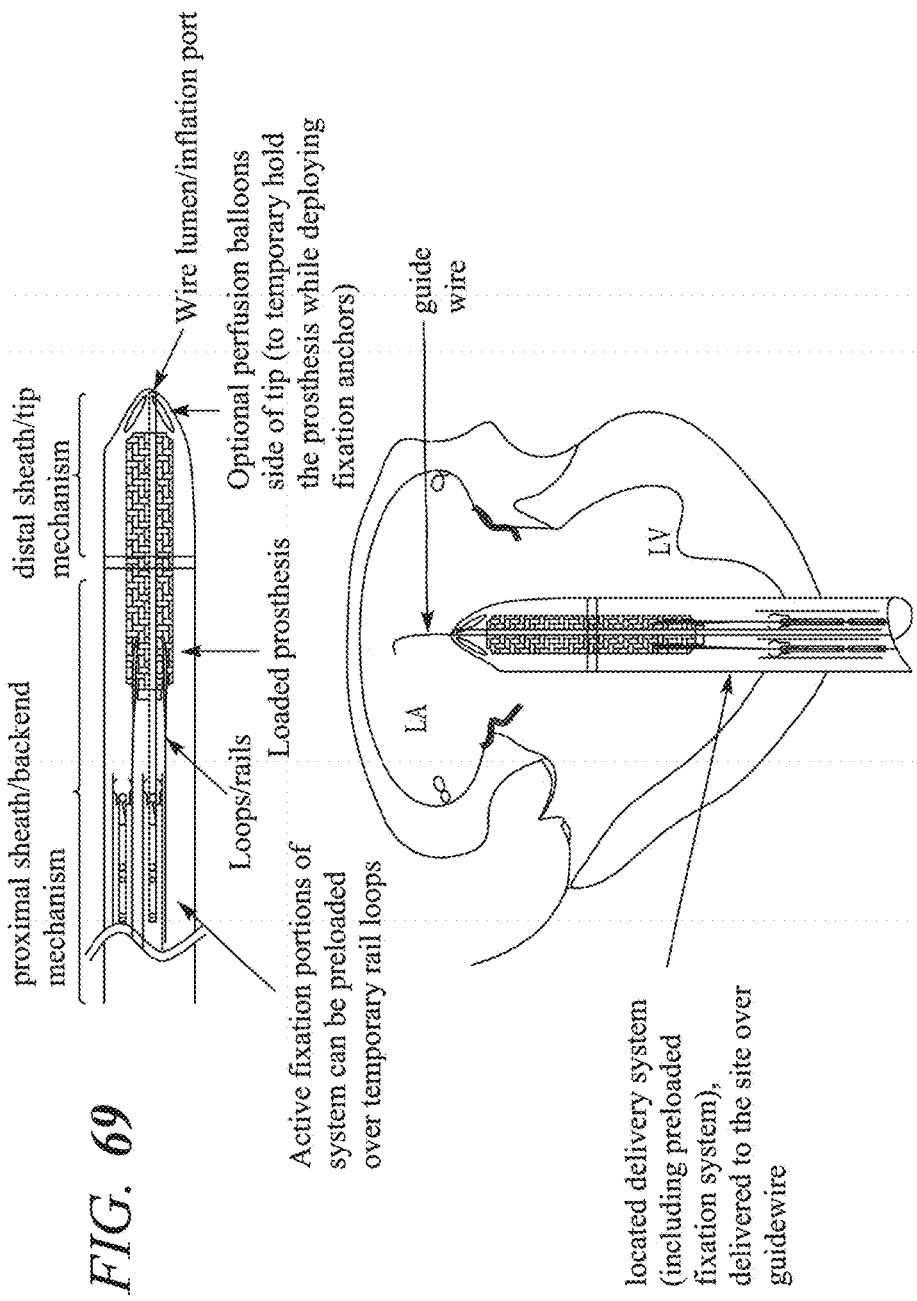

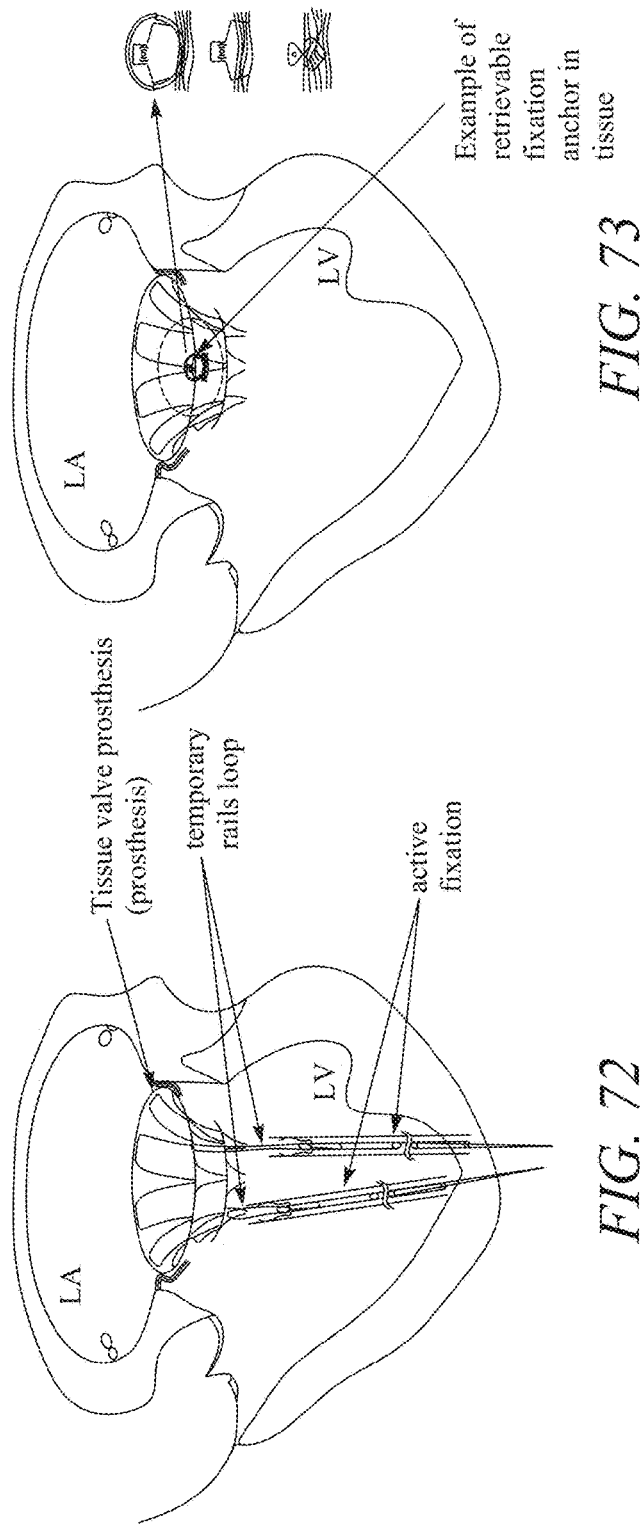

METHODS AND SYSTEMS FOR DELIVERING PROSTHESES USING RAIL TECHNIQUES

RELATED APPLICATIONS

This application is a continuation-in-part of and claims the benefit of International Application No. PCT/US2011/059586, filed Nov. 7, 2011, which in turn claims the benefit of priority to U.S. patent application Ser. No. 13/240,793, filed Sep. 22, 2011, now abandoned, U.S. Provisional Patent Application Ser. No. 61/410,877, filed Nov. 6, 2010, U.S. Provisional Patent Application Ser. No. 61/451,899, filed Mar. 11, 2011 and U.S. Provisional Patent Application Ser. No. 61/431,384, filed Jan. 10, 2011. This application is also related to U.S. Provisional Patent Application No. 61/385,843, filed Sep. 23, 2010, U.S. Provisional Patent Application No. 61/245,246, U.S. Provisional Patent Application No. 61/310,783 and U.S. Provisional Patent Application No. 61/354,298. The entire contents of each of the above-referenced applications are incorporated herein by reference in their entirety for any purpose whatsoever.

BACKGROUND

Valvular heart diseases include mitral valve prolapse in which a leaflet of the mitral valve is displaced into the left atrium during the systolic phase of a cardiac cycle. Mitral valve prolapse can lead to mitral regurgitation in which the mitral valve does not close properly during the systolic phase, causing abnormal leaking of blood from the left ventricle, through the mitral valve and into the left atrium.

Valvular heart diseases also include mitral stenosis in which the orifice of the mitral valve is abnormally narrowed, thus impeding blood flow into the left ventricle. Similarly, tricuspid stenosis can impede blood flow into the right ventricle. Some patients may be affected by a combination of mitral/tricuspid stenosis and mitral/tricuspid valve regurgitation, while others may be affected by either one or the other. Serious valvular heart diseases may be treated by replacing or repairing the defective heart valve in an open heart surgical procedure in which a patient's defective heart valve is manually or robotically replaced with a different valve. The open heart surgical replacement procedure requires placing the patient on cardiopulmonary bypass to stop blood flow through the heart when the heart is opened up.

SUMMARY

In accordance with one exemplary embodiment, a valve prosthesis is provided. The valve prosthesis may include a tubular member configured for deployment in a heart valve annulus, a first set of fastening mechanisms radially and outwardly disposed from the tubular member and configured to attach the valve prosthesis to cardiac tissue above the heart valve annulus, and a second set of fastening mechanisms radially and outwardly disposed from the tubular member and configured to attach the valve prosthesis to cardiac tissue below the heart valve annulus. The valve prosthesis may also include a third set of fastening mechanisms radially and outwardly disposed from the tubular member and configured to attach the valve prosthesis to cardiac tissue at or above the heart valve annulus.

The first set of fastening mechanisms may be formed by proximal portions of a series of loop elements that are connected to form a looped structure. The second set of fastening mechanisms may be formed by distal portions of a series of loop elements that are connected to form a looped structure.

The valve prosthesis may include a plurality of first loop elements connected to form a ring shape. Each of the first loop elements may include a mid portion, a proximal portion that extends radially and outwardly away from the mid portion at a first terminal end of the mid portion, and a distal portion that extends radially and outwardly away from the mid portion at a second terminal end of the mid portion. The mid portions of the plurality of first loop elements may form the tubular member of the valve prosthesis. The proximal portions of the plurality of first loop elements may form the first set of fastening mechanisms of the valve prosthesis. The distal portions of the plurality of first loop elements may form the second set of fastening mechanisms of the valve prosthesis.

The valve prosthesis may also include a plurality of second loop elements connected to form a ring shape. Each of the second loop elements may include a mid portion and a proximal portion that extends radially and outwardly away from the mid portion at a first terminal end of the mid portion. The mid portions of the plurality of first loop elements and the mid portions of the plurality of second loop elements may form the tubular member. The proximal portions of the plurality of first loop elements may form the first set of fastening mechanisms, the distal portions of the plurality of first loop elements may form the second set of fastening mechanisms, and the proximal portions of the plurality of second loop elements may form a third set of fastening mechanisms radially and outwardly disposed from the tubular member and configured to attach the valve prosthesis to cardiac tissue at or above the heart valve annulus.

The plurality of first loop elements and the plurality of second loop elements may be connected side-by-side in an alternating manner to form the ring shape. Each of the plurality of second loop elements may be provided within one of the plurality of first loop elements, and pairs of first and second loop elements may be connected side-by-side to form the ring shape.

The disclosure also provides a method for treating a lumenal anatomical location of a patient. The method includes advancing a distal region of a delivery catheter proximate a target location in a patient's lumenal system, dispensing a penetrating member from the delivery catheter proximate the target location, advancing the penetrating member through a first portion of lumenal tissue proximate the target location to define a first passage, advancing an end of a first tether through the first passage, the first tether having a first anchor disposed at the end thereof, advancing the first tether through the first passage until the first anchor bears against tissue proximate the first passage, disposing a prosthesis over the first tether, and advancing the prosthesis over the first tether to a position proximate the target location.

In accordance with further aspects, the method can further include advancing the penetrating member through a second portion of lumenal tissue proximate the target location to define a second passage. An end of a second tether can be advanced through the second passage, the second tether having a second anchor disposed at the end thereof. The second tether can be advanced through the second passage until the second anchor bears against tissue proximate the second passage. A prosthesis can be disposed over the first and second tethers, and the prosthesis can be advanced over the first and second tethers to a position proximate the target location.

The method can further include anchoring the prosthesis in place in the target location using at least one retainer. The retainer can be attached to the first tether and can urge the prosthesis and anchor toward one another along the first tether. The prosthesis can define an open lumen upon installation. The method can further include disposing a second prosthesis within the open lumen. The second prosthesis can include a lumenal valve that in turn includes synthetic material and/or living tissue.

In accordance with a further aspect, the target location can be proximate a patient's mitral annulus. The first and second passages can pass through the commissures of the mitral valve. The target location can alternatively proximate a patient's tricuspid valve. If desired, the target location can be proximate a patient's abdominal aorta. If so, the prosthesis can include a stent graft. In another embodiment, the target location can be inside a patient's lungs and the prosthesis can include a stent for maintaining patency of an airway. In another embodiment, the target location is inside a patient's gastrointestinal tract. The prosthesis can thus include a stent, such as one for maintaining patency of a portion of the gastrointestinal tract. In another embodiment, the prosthesis includes a replacement stomach valve.

In still another embodiment, the target location is inside a patient's reproductive system and the prosthesis can be a stent for maintaining the patency of a fallopian tube. In another embodiment, the target location can be inside a patient's urinary tract and the prosthesis can be a stent for maintaining the patency of the patient's urinary tract.

In another embodiment, the prosthesis can include at least one tether attached thereto, and the disclosed methods can include attaching the prosthesis tether to the first tether to secure the prosthesis in place.

In one embodiment, the delivery catheter can enter the heart through an incision proximate the bottom of the left ventricle. The delivery catheter can alternatively enters the heart through an incision proximate the top of the left atrium. Moreover, if desired, the delivery catheter can enter the heart percutaneously via an artery.

The disclosure further provides a method for treating a lumenal anatomical location. The method includes advancing a distal region of a delivery catheter proximate a target location in a patient's lumenal system, and deploying a prosthesis from a distal region of the catheter, the prosthesis having at least one tether connected thereto for controlling placement of the prosthesis. If desired, the method can further include directing a fixation catheter over the tether to the prosthesis, and applying at least one retainer to secure the prosthesis to the tissue of the patient. The method can likewise include inflating an inflatable member inside the prosthesis to hold the prosthesis in place while the fixation catheter is used to secure the prosthesis to the tissue of the patient.

The disclosure also provides a prosthesis comprising a tubular member configured for deployment in a lumenal system of a patient having at least one tether extending from the prosthesis for controlling placement of the prosthesis. The disclosure also provides a prosthesis delivery system including a central shaft, a prosthesis as discussed herein disposed on the central shaft, a retractable sheath covering the prosthesis, and a passage in the catheter for housing the least one tether attached to the prosthesis, the conduit having a proximal end and a distal end, the distal end being located proximate the prosthesis.

The disclosure still further provides a prosthesis including a tubular member configured for deployment in a lumenal system of a patient and at least one conduit connected to the tubular member, the conduit being adapted and configured to guide placement of the prosthesis. Similarly, an associated prosthesis delivery system is provided, including a central shaft, a prosthesis disposed on the central shaft, and at least one tether passing through the conduit.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 1 illustrates a cross-sectional view taken along a longitudinal axis of an exemplary valve prosthesis in its deployed state.

FIG. 2 illustrates a cross-sectional view taken along a longitudinal axis of another exemplary valve prosthesis in its deployed state.

FIG. 3 illustrates a cross-sectional view taken along a longitudinal axis of yet another exemplary valve prosthesis in its deployed state.

FIG. 4 illustrates a cross-sectional view taken along a longitudinal axis of still another exemplary valve prosthesis in its deployed state.

FIG. 5A illustrates a longitudinal sectional view of a heart that depicts the exemplary valve prosthesis of FIG. 3 deployed at the annulus of the mitral valve.

FIG. 5B illustrates a transverse sectional view of the heart of FIG. 5A in which the exemplary valve prosthesis is deployed at the annulus of the mitral valve.

FIG. 6 illustrates a perspective view of an exemplary primary loop configured for use and deployment in the posterior region of a heart valve.

FIG. 7 illustrates a perspective view of an exemplary primary loop configured for use and deployment in the anterior region of a heart valve.

FIG. 8 illustrates a perspective view of an exemplary secondary loop configured for deployment in the posterior region of a heart valve.

FIG. 9 illustrates a perspective view of an exemplary secondary loop configured for deployment in the anterior region of a heart valve.

FIG. 10 illustrates a perspective view of an exemplary configuration of a valve prosthesis in which secondary loops (as illustrated in FIG. 8) are disposed within and/or nested within and/or attached to primary loops (as illustrated in FIG. 6), as configured for deployment in the posterior region of a heart valve.

FIG. 11 illustrates a perspective view of the exemplary loops of FIG. 10 where at least a portion of the surface of the primary loops and/or the secondary loops is covered by a tissue and/or non-tissue graft material (e.g., PS base woven or braided depending on end use applications and rate of tissue growth).

FIG. 12 illustrates a perspective view of an exemplary configuration of a valve prosthesis in which secondary loops (as illustrated in FIG. 9) are disposed within and/or nested within and/or attached to primary loops (as illustrated in FIG. 7), as configured for deployment in the posterior region of a heart valve.

FIG. 13 illustrates a perspective view of the exemplary loops of FIG. 12 where at least a portion of the surface of the primary loops is covered by a tissue and/or non-tissue graft material (e.g., PS base woven or braided depending on end use applications and rate of tissue growth).

FIG. 14 illustrates a perspective view of an exemplary configuration of a valve prosthesis in which secondary loops (as illustrated in FIG. 8) and primary loops (as illustrated in FIG. 6) are disposed alternately in a side-by-side manner and/or attached to each other, as configured for deployment in the posterior region of a heart valve.

FIG. 15 illustrates a perspective view of the exemplary loops of FIG. 14 where at least a portion of the surface of the primary loops and/or the secondary loops is covered by a tissue and/or non-tissue graft material.

FIG. 16 illustrates a perspective view of an exemplary configuration of a valve prosthesis in which secondary loops (as illustrated in FIG. 9) and primary loops (as illustrated in FIG. 7) are disposed alternately in a side-by-side manner and/or attached to each other, as configured for deployment in the anterior region of a heart valve.

FIG. 17 illustrates a perspective view of the exemplary loops of FIG. 16 where at least a portion of the surface of the primary loops and/or the secondary loops is covered by a tissue and/or non-tissue graft material.

FIG. 20 illustrates a cross-sectional view taken through a mitral valve in which an exemplary valve prosthesis is deployed at the annulus of the mitral valve and where at least a portion of the surface of the prosthesis is covered by a tissue and/or non-tissue graft material.

FIG. 21 illustrates a cross-sectional view taken through a mitral valve in which an exemplary uncovered valve prosthesis is deployed at the annulus of the mitral valve.

FIGS. 22 illustrates a cross-sectional view taken through the mitral valve shown in FIG. 20 where the valve prosthesis is provided with radio-opaque markers.

FIG. 27 illustrates an exemplary valve prosthesis with a mid portion and/or a distal portion extending below the annular ring that is skirted.

FIG. 28 illustrates a longitudinal section view taken through an exemplary valve prosthesis that is an inverted version of the exemplary valve prosthesis of FIG. 26.

FIG. 29 illustrates a longitudinal section view taken through an exemplary valve prosthesis in which a proximal portion that extends above the annular ring into the atrium is skirted.

FIG. 30 illustrates a longitudinal section view taken through another exemplary valve prosthesis in which a proximal portion that extends above the annular ring into the atrium is skirted.

FIGS. 47A-47E illustrate left ventricular transapical access of an exemplary delivery device for delivering a valve prosthesis.

FIG. 49 illustrates certain aspects of an exemplary portion of a delivery system in accordance with the present disclosure.

FIG. 50 illustrates an alternative embodiment of a portion of a delivery system in accordance with the present disclosure.

FIG. 51 illustrates still further aspects of a delivery system in accordance with the present disclosure.

FIGS. 52B, 53B, 54B, 55B and 56B illustrate a second exemplary method and system for disposing a pair of guide rails in the mitral annulus, wherein anchors are disposed on the top side of the annulus of the mitral valve by way of the left ventricle.

FIG. 57A illustrates an exemplary prosthesis that can serve as a valve prosthesis or open conduit once implanted in accordance with the disclosure.

FIG. 57B illustrates the prosthesis of FIG. 57A with a pair of guides for accepting a pair of guide rails to facilitate implantation of the prosthesis.

FIG. 57C illustrates a half or hemi prosthesis having a pair of guides for accepting a pair of guide rails to facilitate implantation of the prosthesis.

FIGS. 58A-58B and 60A illustrate an exemplary placement of a full prosthesis in the mitral orifice by way of rails anchored from beneath the mitral annulus.

FIGS. 61A and 62A illustrate an exemplary placement of a full prosthesis having a plurality of tethers attached thereto in the mitral annulus.

FIGS. 61B and 62B illustrate an exemplary placement of a half prosthesis having a plurality of tethers attached thereto in the mitral annulus.

FIGS. 63A, 63B, 63C, 63D, 63E, and 64A-64B illustrate embodiments of techniques utilizing rails anchored in valve leaflets.

FIGS. 66A, 66B, 67A, 68A, 68B, 69-73 illustrate further exemplary methods and systems for deploying a prosthesis using temporary rails.

DETAILED DESCRIPTION

Figure 18A:
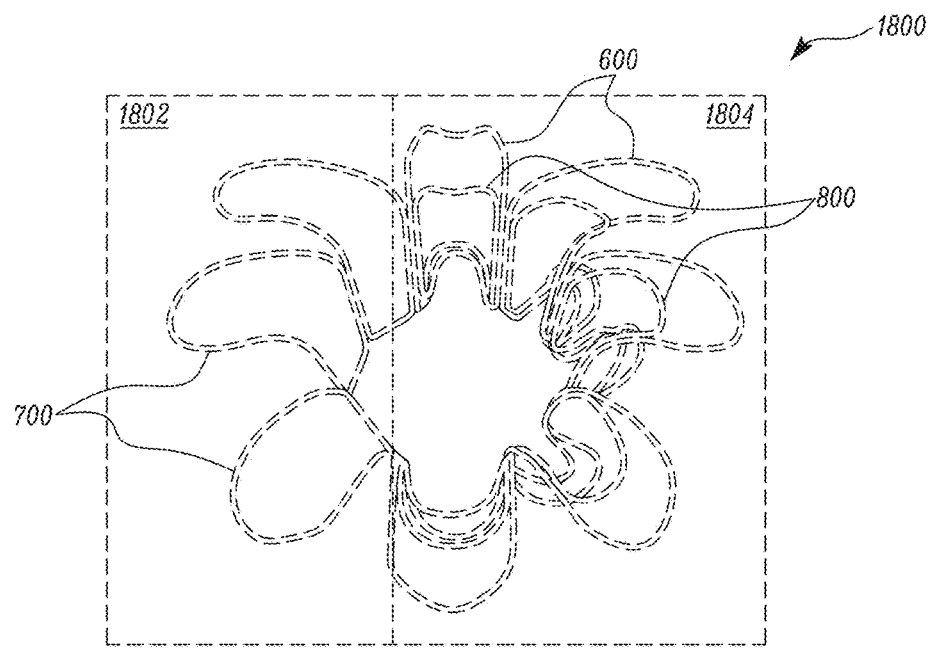
FIG. 18A illustrates a top view of an exemplary valve prosthesis in which an anterior portion for deployment in the anterior region of a heart valve is configured differently from a posterior portion for deployment in the posterior region of a heart valve.

Exemplary embodiments provide systems, devices and methods for replacing a mitral or tricuspid valve of the heart in a minimally invasive and/or percutaneous manner. In other embodiments, systems and methods are provided for repairing other aspects of lumenal systems. Some exemplary embodiments provide stent-based valve prostheses configured for deployment at and replacement of the mitral or tricuspid valve of the heart. Valve replacement and other procedures described herein using exemplary systems, devices and methods as disclosed herein lowers the cost of the overall therapy compared to conventional surgical valve replacement and allows improved patient care including, but not limited to, shorter procedure and hospitalization times.

Certain exemplary valve prostheses include looped elements joined together to form radial planes that extend from the longitudinal stent body of the prosthesis and that fasten the prosthesis against and/or to the surrounding cardiac anatomy. The spacings between the loop elements and within each loop element in an exemplary valve prosthesis may be configured such that the valve prosthesis is compliant and conforms to the shape and the anatomy of the valve annulus in a natural manner, without compromising the radial strength for the mid and distal portions of the loop elements that anchor to the valve tissue. The spacings between the loop elements and within each loop element in an exemplary valve prosthesis may be adjusted and covered with tissue, a graft with tissue (e.g., PS base woven or braided depending on end use applications and rate of tissue growth), and/or any other suitable material, e.g., a porous layer. In an exemplary embodiment, a graft material may be impregnated with a tissue growth agent in desired portions of the prosthesis in order to encourage faster tissue growth which, in turn, allows for enhanced prosthesis fixation and lower fatigue.

An exemplary valve prosthesis may be collapsible and may have a first smaller diameter or lateral dimension when in a collapsed state. The valve prosthesis may be disposed inside a delivery device in the collapsed state for delivery to a heart valve annulus. An exemplary valve may be expandable from its collapsed state and may have a second larger diameter when in an expanded and deployed state. The valve prosthesis may self-expand or may be expanded by a catheter upon delivery for deployment at a heart valve annulus. The expansion of the valve prosthesis allows the prosthesis to naturally conform to the anatomy of the heart valve annulus and allows, in conjunction with fastening mechanisms, secure fastening of the valve prosthesis to the surrounding cardiac anatomy.

Exemplary valve prostheses may be formed of any suitable material including, but not limited to, stainless steel (e.g., flat or round spring tempered stainless steel, etc.), one or more shape memory alloys such as nickel titanium or NiTi (e.g., in the form of a laser-cut stent or one or more wires set to a particular shape using heat, etc.), Drawn Filed Tubing (DFT) mix of NiTi and Platinum (Pt) or NiTi, etc. The thickness of the DFT core may be configured and tailored for enhanced radio-opacity and fatigue resistance based on the end use application of the valve prosthesis. Portions of exemplary valve prostheses may be bare or grafted with, for example, tissue and/or fabric (e.g., PS base woven or braided depending on end use applications and rate of tissue growth).

In some exemplary embodiments, one or more inflatable channels may be provided or attached to the mid and/or distal portions of an exemplary valve prosthesis in a radial or series configuration. After deployment of the prosthesis, the channels may be inflated to provide additional friction and fixation, if necessary. In an exemplary embodiment, the mid and/or distal portions of a valve prosthesis may be impregnated with a hydrophobic material that may be released in a timed manner. After deployment of the prosthesis, the material may be activated and may act as a sponge, thereby providing additional friction and fixation.

FIGS. 1-4 illustrate cross-sectional views taken along a longitudinal axis L of an exemplary stented valve prostheses in their deployed state.

FIG. 1 illustrates a cross-sectional view taken along the longitudinal axis L of an exemplary stented valve prosthesis 100 including a proximal portion 102 that is configured to fasten or secure the valve prosthesis 100 to the atrium, a mid portion 104 that is disposed in the annulus of a heart valve (e.g., the mitral valve or the tricuspid valve), and a distal portion 106 that is configured to fasten or secure the valve prosthesis 100 to the ventricle.

The proximal portion 102 of the valve prosthesis 100 may include one or more annular size reducers 108 that extend radially about the proximal portion 102 in spaced apart fashion to form a ring shape. The annular size reducers 108 configure the valve prosthesis 100 to have a smaller valve size, while fastening the valve prosthesis 100 securely and in a compliant manner to the atrium and the ventricle. The annular size reducers 108 can also prevent paravalvular leaks that may occur through small openings or spaces that may exist between the heart and the valve prosthesis 100.

The proximal portion 102 may include one or more fastening, anchoring or bracing mechanisms 110 for fastening the valve prosthesis 100 to an upper portion of the region of the heart in which the valve prosthesis 100 is deployed. In an exemplary embodiment in which the valve prosthesis 100 is deployed to replace the mitral valve, the fastening mechanism 110 may be used to fasten the valve prosthesis 100 to/against the left atrium or to/against an upper portion of the annulus of the mitral valve. In another exemplary embodiment in which the valve prosthesis 100 is deployed to replace the tricuspid valve, the fastening mechanism 110 may be used to fasten the valve prosthesis 100 to the right atrium or to an upper portion of the annulus of the tricuspid valve.

The fastening mechanism 110 may form a compliant structure that conforms to the anatomy of the surrounding heart tissue and that, therefore, securely fastens the valve prosthesis 100 to the surrounding heart tissue. Exemplary fastening mechanisms 110 may include individual or multiple palm-like contoured anchoring, fastening or bracing mechanisms. Exemplary fastening mechanisms 110 may be formed of the radially extending proximal portions of a connected series of loop elements.

In an exemplary embodiment, the fastening mechanism 110 includes one or more arcuate structures that initially extend radially and outwardly in a substantially perpendicular direction relative to the stent body 114 of the valve prosthesis 100, and that transition to a downward arc toward the distal portion 106 until reaching a terminal end 112. The fastening mechanism 110 extends above the valve leaflets such that the leaflets are disposed under the arcuate structure and such that the end 112 of the arcuate structure fastens the valve prosthesis 100 to heart tissue found above and/or near the valve leaflets.

The proximal portion 102 may also include one or more mechanisms for holding, repositioning, retrieving and releasing the valve prosthesis 100 to be used during deployment of the valve prosthesis 100 to the annulus of a heart valve by a delivery system, discussed in further detail below.

The mid portion 104 of the valve prosthesis 100 includes a stent body 114 having a bore configured to be placed within the annulus of a heart valve. At its top end, the stent body 114 opens into an annulus 116 of the heart valve. In exemplary embodiments, one or more radio-opaque markers may be placed on the stent body 114 to facilitate in positioning and deploying the valve prosthesis 100 by a delivery system. The markers may also enhance physician feedback and a tactile feeling. The radio-opaque markers may be placed only on the posterior side of the stent body 114, only on the anterior side of the stent body 114, or on both posterior and anterior sides of the stent body 114. Exemplary markers may include, but are not limited to, radial markers, individual markers, pad printed markers and/or woven monofilament markers.

A portion of the outer surface of the proximal portion 102 and/or a portion of the outer surface of the mid portion 104 may include a compliant pocket 120 that is configured to further eliminate paravalvular leaks around the valve prosthesis 100. In an exemplary embodiment, the compliant pocket 120 is mounted on the stent body 114 and extends radially around the stent body 114. In an exemplary embodiment, the compliant pocket 120 may extend to the distal portion 106 of the valve prosthesis. The compliant pocket 120 may also facilitate fastening and anchoring of the valve prosthesis 100 to the surrounding cardiac anatomy while minimizing damage to cardiac tissue. The compliant pocket 120 may enhance the overall compliance integrity of the valve prosthesis 100 and fatigue resistance.

In an exemplary embodiment, the outer surface of the compliant pocket 120 may be impregnated with tissue growth and/or with a coating of another material to keep the outer surfaces of the valve prosthesis 100 on the anterior side away from the anterior region of the mitral valve. This configuration protects the cardiac anatomy in the anterior region of the heart from inadvertent damage caused by the valve prosthesis 100. In other exemplary embodiments, the outer surface of the compliant pocket 120 may be impregnated with tissue growth and/or with a coating of another material on the anterior side of the prosthesis, on the posterior side of the prosthesis, or on both the anterior and posterior sides of the prosthesis. The compliant pocket 120 may have a porous exterior layer, e.g., a cushioned layer, that extends on the posterior side, the anterior side, or both the posterior and anterior sides. The porous exterior layer may enhance the overall system compliance, integrity and fatigue resistance. The porous exterior layer may be impregnated with tissue growth and/or other coatings.

The distal portion 106 of the valve prosthesis 100 includes one or more fastening, anchoring or bracing mechanisms 122 for fastening the valve prosthesis 100 to a lower portion of the region of the heart in which the valve prosthesis 100 is deployed. In an exemplary embodiment in which the valve prosthesis 100 is deployed to replace the mitral valve, the fastening mechanism 122 may be used to fasten the valve prosthesis 100 to the left ventricle or to a lower portion of the annulus of the mitral valve. In another exemplary embodiment in which the valve prosthesis 100 is deployed to replace the tricuspid valve, the fastening mechanism 122 may be used to fasten the valve prosthesis 100 to the right ventricle or to a lower portion of the annulus of the tricuspid valve.

The fastening mechanism 122 may form a compliant structure that conforms to the anatomy of the surrounding heart tissue (or otherwise, as disclosed below) and that, therefore, securely fastens the valve prosthesis 100 to the surrounding heart tissue. Exemplary fastening mechanisms 122 may include individual or multiple palm-like contoured anchoring, fastening or bracing mechanisms. Exemplary fastening mechanisms 122 may be formed of the radially extending proximal portions of a connected series of loop elements.

In an exemplary embodiment, the fastening mechanism 122 includes one or more arcuate structures that initially extend outwardly in a substantially perpendicular direction relative to the stent body 114 of the valve prosthesis 100, and that transition to an upward arc toward the proximal portion 102. The fastening mechanism 122 extends below the valve leaflets such that leaflets are disposed above the arcuate structure and such that the end of the arcuate structure fastens the valve prosthesis 100 to heart tissue found under and/or near the valve leaflets.

In an exemplary embodiment, the fastening mechanism 122 is anchored underneath one or both of the two mitral valve commissures. In this exemplary embodiment, the fastening mechanism 122 may include two sets of arcuate structures placed about 180 degrees apart on the stent body 114 to engage both the mitral valve commissures. Each set of arcuate structures may include one or more arcuate structures. The arcuate structures may extend radially about the outer surface of the stent body 114 in a spaced apart manner.

The distal portion 106 may also include one or more mechanisms for holding, repositioning, retrieving and releasing the valve prosthesis 100 to be used during deployment of the valve prosthesis 100 to the annulus of a heart valve by a delivery system.

FIG. 2 illustrates a cross-sectional view taken along a longitudinal axis of another exemplary stented valve prosthesis 200 in its deployed state. The valve prosthesis 200 includes a proximal portion 202 that is configured to fasten the valve prosthesis 200 to the atrium and a mid portion 204 that is disposed in the annulus of a heart valve. The valve prosthesis 200 lacks a distal portion configured to fasten the valve prosthesis 200 to the ventricle.

The proximal portion 202 of the valve prosthesis 200 may include one or more annular size reducers 208 that configure the valve prosthesis 200 to have a smaller valve size while fastening the valve prosthesis securely and in a compliant manner to the atrium and the ventricle. The annular size reducers 208 extend radially about the proximal portion 202 in spaced apart fashion to form a ring shape. The proximal portion 202 of the valve prosthesis 200 lacks a compliant pocket in this illustrative embodiment.

The proximal portion 202 may include one or more fastening, anchoring or bracing mechanisms 210 for fastening the valve prosthesis 200 to an upper portion of the region of the heart in which the valve prosthesis 200 is deployed. The fastening mechanism 210 may form a compliant structure that conforms to the anatomy of the surrounding heart tissue and that, therefore, securely fastens the valve prosthesis 200 to the surrounding heart tissue. The fastening mechanism 210 extends above the valve leaflets such that leaflets are disposed under the arcuate structure and such that the end 212 of the arcuate structure fastens the valve prosthesis 200 to heart tissue found above and/or near the valve leaflets.

The mid portion 204 of the valve prosthesis 200 includes a stent body 214 having a bore configured to be placed within the annulus of a heart valve. At its top end, the stent body 214 opens into an annulus 216 of the heart valve.

FIG. 3 illustrates a cross-sectional view taken along a longitudinal axis of another exemplary stented valve prosthesis 300 in its deployed state. The valve prosthesis 300 includes a proximal portion 302 that is configured to fasten the valve to the atrium, a mid portion 304 that is disposed in the annulus of a heart valve, and a distal portion 306 that is configured to fasten the valve prosthesis 300 to the ventricle.

The proximal portion 302 of the valve prosthesis 300 may include one or more annular size reducers 308 that configure the valve prosthesis 300 to have a smaller valve size while fastening the valve prosthesis securely and in a compliant manner to the atrium and the ventricle. The annular size reducers 308 extend radially about the proximal portion 302 in spaced apart fashion to form a ring shape. The proximal portion 302 of the valve prosthesis 300 lacks a compliant pocket.

The proximal portion 302 may include one or more fastening, anchoring or bracing mechanisms 310 for fastening the valve prosthesis 300 to an upper portion in the region of the heart in which the valve prosthesis 300 is deployed. The fastening mechanism 310 may form a compliant structure that conforms to the anatomy of the surrounding heart tissue and that, therefore, securely fastens the valve prosthesis 300 to the surrounding heart tissue. The fastening mechanism 310 extends above the valve leaflets such that leaflets are disposed under the arcuate structure and such that the end 312 of the arcuate structure fastens the valve prosthesis 300 to heart tissue found above and/or near the valve leaflets.

The mid portion 304 of the valve prosthesis 300 includes a stent body 314 having a bore configured to be placed within the annulus of a heart valve. At its top end, the stent body 314 opens into an annulus 316 of the heart valve.

The distal portion 306 of the valve prosthesis 300 includes one or more fastening, anchoring or bracing mechanisms 322 for fastening the valve prosthesis 300 to a lower portion in the region of the heart in which the valve prosthesis 300 is deployed. The fastening mechanism 322 may form a compliant structure that conforms to the anatomy of the surrounding heart tissue and that, therefore, securely fastens the valve prosthesis 300 to the surrounding heart tissue.

FIG. 4 illustrates a cross-sectional view taken along a longitudinal axis of another exemplary stented valve prosthesis 400 in its deployed state. The valve prosthesis 400 includes a proximal portion 402 that is configured to fasten the valve to the atrium and a mid portion 404 that is disposed in the annulus of a heart valve. The proximal portion 402 of the valve prosthesis 400 has a compliant pocket 406. The valve prosthesis 400 lacks a distal portion configured to fasten the valve prosthesis 400 to the ventricle.

The proximal portion 402 of the valve prosthesis 400 may include one or more annular size reducers 408 that configure the valve prosthesis 400 to have a smaller valve size while fastening the valve prosthesis securely and in a compliant manner to the atrium and the ventricle. The annular size reducers 408 extend radially about the proximal portion 402 in spaced apart fashion to form a ring shape. The proximal portion 402 of the valve prosthesis 400 includes a compliant pocket 420 that is configured to further eliminate paravalvular leak around the valve prosthesis 400. The compliant pocket 420 may also facilitate fastening and anchoring of the valve prosthesis 400 to the surrounding cardiac anatomy, while minimizing damage to cardiac tissue.

The proximal portion 402 may include one or more fastening, anchoring or bracing mechanisms 410 for fastening the valve prosthesis 400 to an upper portion in the region of the heart in which the valve prosthesis 400 is deployed. The fastening mechanism 410 may form a compliant structure that conforms to the anatomy of the surrounding heart tissue and that, therefore, securely fastens the valve prosthesis 400 to the surrounding heart tissue. The fastening mechanism 410 extends above the valve leaflets such that leaflets are disposed under the arcuate structure and such that the end 412 of the arcuate structure fastens the valve prosthesis 400 to heart tissue found above and/or near the valve leaflets.

The mid portion 404 of the valve prosthesis 400 includes a stent body 414 having a bore configured to be placed within the annulus of a heart valve. At its top end, the stent body 414 opens into an annulus 416 of the heart valve.

FIG. 5A illustrates a longitudinal sectional view of a heart that shows the exemplary valve prosthesis of FIG. 3 deployed at the annulus of the mitral valve. FIG. 5A depicts a heart 500 with the mitral valve annulus 502 formed between the left atrium 504 and the left ventricle 506. The exemplary valve prosthesis 508 of FIG. 3 is deployed at the mitral valve annulus 502 to replace the mitral valve. The mid portion 510 forming the stent body 508 of the valve prosthesis 500 is positioned in and contacts the annulus of the mitral valve and extends into the left ventricle. The proximal portion 512 of the valve prosthesis 500 is disposed above the valve leaflets in an exemplary embodiment, or above where the leaflets would be in another exemplary embodiment in which the valve leaflets are removed. One or more fastening mechanisms in the proximal portion 512 anchor the valve prosthesis 500 to the walls of the left atrium above the valve leaflets. The distal portion 514 of the valve prosthesis 500 is disposed under the valve leaflets. One or more fastening mechanisms in the distal portion 514 anchor the valve prosthesis 500 to the walls of the left ventricle under the valve leaflets.

That is, in an exemplary embodiment, the proximal portion of the valve prosthesis 500 is fastened to the left atrium by one or more fastening mechanisms and the distal portion of the valve prosthesis 500 is fastened to the left ventricle by one or more fastening mechanisms. The combination of the fastening mechanisms securely anchors the valve prosthesis 500 both above and below the annulus of the heart valve. In other exemplary embodiments, additional fastening mechanisms may be provided to fasten the valve prosthesis 500 to cardiac tissue in the annulus of the heart valve.

FIG. 5B illustrates a transverse sectional view of the heart 500 of FIG. 5A in which the valve prosthesis 508 is deployed in the mitral valve. The top view of the valve leaflets is obscured by the proximal portion 512 of the valve prosthesis 508 which extends over the valve leaflets and fastens the valve prosthesis to the left atrium.

Exemplary valve prostheses 100, 200 and 400 illustrated in FIGS. 1, 2 and 4, respectively, may be deployed at a mitral or a tricuspid valve in a manner similar to the exemplary deployment of the valve prosthesis shown in FIGS. 5A and 5B.

A valve prosthesis may include one or more series of loop elements, each series of looped elements being connected to form a looped structure. The looped structures may be disposed along the circumference of the annulus of a heart valve, and may provide uniform support of the valve prosthesis against the annulus of a heart valve. In an exemplary embodiment in which the prosthesis is configured for deployment at a mitral valve, the looped structures forming the prosthesis may be substantially D-shaped to conform naturally to the substantially D-shaped cross-section of the mitral valve. In an exemplary embodiment in which the prosthesis is configured for deployment at a tricuspid valve, the looped structures forming the prosthesis may be substantially circular in shape when deployed to conform naturally to the substantially circular cross-section of the tricuspid valve.

Exemplary valve prostheses may include one or more types of loop elements, e.g., primary loops and/or secondary loops. A looped structure formed of a connected series of loop elements may include single type of loop element (e.g., primary loops or secondary loops) or may include two or more types of loop elements (e.g., primary and secondary loops). In an exemplary embodiment, the primary loops may be longer along the longitudinal axis L than the secondary loops.

FIG. 6 illustrates a perspective view of an exemplary primary loop 600 configured for use and deployment in the posterior region of a heart valve. An exemplary primary loop 600 includes a mid portion 602 that is formed of two or more substantially straight segments, such as first segment 604 and second segment 606 that extend substantially parallel to each other. In other exemplary embodiments, the segments 604 and 608 may not be straight. The mid portion 602 is configured to be positioned in the heart valve annulus adjacent to the heart wall in the valve annulus, such that the straight segments 604 and 606 extend along the longitudinal axis L of the heart valve annulus.

In an exemplary embodiment, additional support structures, e.g., one or more struts, may be included in the mid portion 602 to tailor the compliance of the mid portion 602 to the annulus of the heart valve. The support structures may include one or more zigzagging struts that extend across the mid portion 602 along the circumference of the valve prosthesis. In an exemplary embodiment, the struts may extend across the mid portion 602 in a substantially serpentine configuration.

An exemplary primary loop 600 includes a proximal portion 608 that forms a first terminal end of the loop element. The proximal portion 608 is curved and extends radially and outwardly away from the longitudinal axis L of the valve prosthesis in an arcuate manner. The tip 610 of the proximal portion 608 curves downwardly to some extent in an exemplary embodiment. The proximal portion 608 is configured to be positioned just above the annular ring of the heart valve such that the arcuate shape of the proximal portion 608 provides a fastening mechanism for radial fastening of the valve prosthesis to the atrium or to an upper portion of the heart valve annulus. The fastening mechanism also provides an outer radial force against the top of the heart valve annulus which securely attaches the valve prosthesis to the heart valve annulus. In the looped structure formed by multiple primary loops 600, the proximal portions 608 adapt to the shape of the annulus of a heart valve and provide natural coverage and a complete radial seal that eliminates paravalvular leaks. In an exemplary embodiment, the tip 610 of the proximal portion 608 may be adjustable and may include a sharp end, e.g., a barb, to penetrate the valve annulus to further secure the valve prosthesis to the annulus.

In the exemplary embodiment, the primary loop 600 includes a distal portion 612 that forms a second terminal end of the loop element. The distal portion 612 is curved and extends radially and outwardly away from the longitudinal axis L of the valve prosthesis in an arcuate manner. The tip 614 of the distal portion 612 curves upwardly to some extent in an exemplary embodiment. The distal portion 612 is configured to be positioned under the valve leaflets such that the arcuate shape of the distal portion 612 provides a fastening mechanism for radial fastening of the valve prosthesis to the ventricle below the valve leaflets. The fastening mechanism also provides an outer radial force against the valve annulus which securely attaches the valve prosthesis to the valve annulus and that provides a radial seal between the outer surface of the valve prosthesis and the annulus of a heart valve to prevent paravalvular leaks.

In exemplary embodiments, the proximal portions 608 and/or distal portions 612 of the primary loops 600 are flexible, and the curvature and mushroom shape formed by the looped series of primary loops 600 are automatically adjustable, e.g., by adjusting the curvature radium, due to the flexible nature of the proximal and/or distal portions. This adjustability allows for adjusting the shape of the annulus formed by the valve prosthesis. This allows an exemplary valve prosthesis to conform to the annular shape of any heart valve. That is, a looped series of connected primary loops may be placed in any heart valve annulus, and the compliant nature of the loops will allow the prosthesis to conform to the particular structure of the valve annulus. As such, one size of the valve prosthesis may fit any annulus and this may reduce the overall delivery profile of the prosthesis for a delivery device and may, consequently, reduce the access puncture point and improve deliverability and tactile feeling of the valve prosthesis. In addition, a clinically relevant smaller valve annulus size may have improved shelf life.

FIG. 7 illustrates a perspective view of an exemplary primary loop 700 configured for use and deployment in the anterior region of a heart valve. The exemplary primary loop 700 lacks the distal portion, e.g., similar to the distal portion 612 in FIG. 6. That is, in exemplary primary loop 700, the second terminal end of the loop element is not curved and does not extend radially outwardly and away from the longitudinal axis L of the valve prosthesis in an arcuate manner.

The proximal portions and/or the distal portions of the primary loops may also include one or more mechanisms for holding, repositioning, retrieving and releasing the valve prosthesis to be used during deployment of the valve prosthesis to the heart valve annulus by a delivery system. In exemplary embodiments, the proximal portions, the mid portions and/or the distal portions of the primary loops may be covered with tissue, a graft with tissue (e.g., PS base woven or braided depending on end use applications and rate of tissue growth), and/or any other suitable material, e.g., a porous layer.

In exemplary embodiments, one or more markers, e.g., radio-opaque markers, may be placed along the radial length of the proximal, mid and/or distal portions of the primary loops. The markers may take the form of bands or pad prints in some exemplary embodiments.

FIG. 8 illustrates a perspective view of an exemplary secondary loop 800 configured for use and deployment in the posterior region of a heart valve. The exemplary secondary loop 800 includes a mid portion 802 that is formed of two or more substantially straight segments 804 and 806 that extend substantially parallel to each other. The mid portion 802 is configured to be positioned in the heart valve annulus and adjacent to the heart wall in the heart valve annulus, such that the straight segments 804 and 806 extend along the longitudinal axis L of the heart valve annulus.

In an exemplary embodiment, additional support structures, e.g., struts, may be included in the mid portion 802 to tailor the compliance of the mid portion 802 to the annulus of the heart valve. The support structures may include one or more zigzagging struts that extend across the mid portion 802 along the circumference of the valve prosthesis. In an exemplary embodiment, the struts may extend across the mid portion 802 in a substantially serpentine configuration. Exemplary support structures may be included in any of the exemplary primary and/or secondary loops described herein.

An exemplary secondary loop 800 includes a proximal portion 808 that forms a first terminal end of the loop element. The proximal portion 808 is curved and extends radially outwardly and away from the longitudinal axis L of the valve prosthesis in an arcuate manner. The tip 810 of the proximal portion 808 curves downwardly to some extent in an exemplary embodiment. In an exemplary embodiment, the proximal portion 808 is configured to be positioned in the heart valve annulus such that the arcuate shape of the proximal portion 808 provides a fastening mechanism for attaching the valve prosthesis to the heart wall in the annulus. In another exemplary embodiment, the proximal portion 808 is configured to be positioned over the valve leaflets such that the arcuate shape of the proximal portion 808 provides a fastening mechanism for attaching the valve prosthesis to the atrium or to an upper portion of the valve annulus. In exemplary embodiments, the proximal portions 808 of the secondary loops 800 provide a spacing between the heart valve and the valve prosthesis. In an exemplary embodiment, the tip 810 of the proximal portion 800 may be adjustable and may include a sharp end, e.g., a barb, to penetrate the valve annulus to further secure the valve prosthesis to the annulus.

In an exemplary embodiment, the secondary loop 800 includes a distal portion 812 that forms a second terminal end of the loop element. The distal portion 812 is curved and extends radially outwardly and away from the mid portion 802 of the valve prosthesis in an arcuate manner. The tip 814 of the distal portion 812 curves upwardly to some extent in an exemplary embodiment. In an exemplary embodiment, the distal portion 812 is configured to be positioned in the valve annulus such that the arcuate shape of the distal portion 812 provides a fastening mechanism for radially fastening the valve mechanism to the heart wall in the annulus. In another exemplary embodiment, the distal portion 812 is configured to be positioned under the valve leaflets such that the arcuate shape of the distal portion 812 provides a fastening mechanism for radially fastening the valve prosthesis to the ventricle below the valve leaflets. The fastening mechanism also provides an outer radial force against the valve annulus which securely attaches the valve prosthesis to the heart valve annulus and that provides a radial seal between the outer surface of the valve prosthesis and the heart valve annulus to prevent paravalvular leaks.

FIG. 9 illustrates a perspective view of an exemplary secondary loop 900 configured for deployment in the anterior region of a heart valve. The secondary loop 900 lacks the distal portion (e.g., the distal portion 812 illustrated in FIG. 8). That is, in exemplary secondary loop 900, the second terminal end of the loop element is not curved and does not extend radially outwardly and away from the longitudinal axis L of the valve prosthesis in an arcuate manner.

The proximal portions and/or the distal portions of the secondary loops may also include one or more mechanisms for holding, repositioning, retrieving and releasing the valve prosthesis to be used during deployment of the valve prosthesis to the heart valve annulus by a delivery system. In exemplary embodiments, the proximal portions, the mid portions and/or the distal portions of the secondary loops may be covered with tissue, a graft with tissue (e.g., PS base woven or braided depending on end use applications and rate of tissue growth), and/or any other suitable material, e.g., a porous layer. The proximal portions of the secondary loops, covered with a layer or uncovered, may act as compliant spacers between the native tissue valve and the valve prosthesis. In exemplary embodiments, the mid portions of the secondary loops may act as a spacer and radial support between the valve prosthesis and the native tissue valve.

In exemplary embodiments, one or more markers, e.g., radio-opaque markers, may be placed along the radial length of the proximal, mid and/or distal portions of the secondary loops. The markers may take the form of bands or pad prints in some exemplary embodiments.

In exemplary embodiments, the primary loops may all have the same size and configuration or may have varied sizes and configurations. In exemplary embodiments, the secondary loops may all have the same size and configuration or may have varied sizes and configurations. In an exemplary embodiment, the secondary loops are smaller in size than the primary loops.

In an exemplary embodiment, the anterior and posterior regions of the valve prosthesis, respectively configured for deployment in the anterior and posterior regions of a heart valve, have the same structural configuration. In exemplary embodiments suitable for application in mitral and tricuspid valves of the heart, the valve prosthesis is configured differently in its anterior region and its posterior region respectively configured for deployment in the anterior and posterior regions of a heart valve. In exemplary embodiments, the anterior and posterior regions of the valve prosthesis may be configured such that the radial extensions and/or radial lengths of the proximal and distal portions of the loops are configured differently for the anterior and posterior regions. In exemplary embodiments, the anterior and posterior regions of the valve prosthesis may be configured such that the primary and/or secondary loops in the anterior regions have different structural configurations than the primary and/or secondary loops in the posterior regions. As illustrated in FIGS. 6 and 8, the primary loops 600 and secondary loops 800 configured for deployment in the posterior region of a heart valve may include the distal portions 612 and 812, respectively. As illustrated in FIGS. 7 and 9, the primary loops 700 and secondary loops 900 configured for deployment in the anterior region may lack the distal portions for improved safety and for efficacy of the valve replacement procedure, while securing the valve prosthesis against the aortic valve and the aortic trunk. The lack of the distal portions in the anterior region protects the aortic valve and the aortic trunk that are present in the anterior region of the heart from inadvertent damage caused by radially extending distal portions.

As illustrated in FIGS. 6 and 7, in exemplary embodiments, the primary loops 600 configured for deployment in the anterior region may have proximal portions 608 that are curved in a more exaggerated arcuate shape than the proximal portions 708 of the primary loops 700 that are configured for deployment in the anterior region of a heart valve. That is, the proximal portion 708 may curve downward from the transverse axis T toward the distal portion of the loop element to a greater extent than the proximal portion 608 curves downward from the transverse axis T toward the distal portion of the loop element.

Similarly, as illustrated in FIGS. 8 and 9, in exemplary embodiments, the secondary loops 900 configured for deployment in the anterior region of a heart valve may have proximal portions 908 that are curved in a more exaggerated arcuate shape than the proximal portions 808 of the secondary loops 800 that are configured for deployment in the posterior region of a heart valve. That is, the proximal portion 908 may curve downward from the transverse axis T toward the distal portion of the loop to a greater extent than the proximal portion 808 curves downward from the transverse axis T toward the distal portion of the loop. The different configurations of the loop elements allow the anterior and posterior portions of the valve prosthesis to closely conform to the surrounding anterior and posterior anatomy, respectively, of the heart.

The primary and secondary loops in the posterior region may act as compliant spacers between the posterior region of the heart and the valve prosthesis.

In the assembled valve prosthesis, the primary and secondary loop elements may be connected together with their centers substantially aligned along a radial plane. The loop elements may be connected by sutures or may be laser-cut to form a contiguous or substantially contiguous looped structure extending radially about a radial plane.

In exemplary embodiments illustrated in FIGS. 10-13, the primary loops connected side-by-side in series to form a looped structure that fits into a heart valve annulus and that supports the valve prosthesis against the annulus of the heart valve. The secondary loops are provided within and/or nested within the primary loops.

FIG. 10 illustrates a perspective view of an exemplary configuration of a valve prosthesis in which secondary loops 800 (as illustrated in FIG. 8) are disposed within and/or nested within primary loops 600 (as illustrated in FIG. 6), as configured for deployment in the posterior region of a heart valve. The primary loops 600 are aligned with each other and connected side-by-side to form a looped structure that can fit into the annulus of a heart valve. In the looped structure formed by the primary loops 600, the proximal portions 608 of the primary loops 600 are aligned along a first radial plane, and the distal portions 612 of the primary loops 600 are aligned along a second radial plane. In an exemplary embodiment, the primary loops 600 are connected side-by-side, leaving an amount of spacing between adjacent primary loops. In another exemplary embodiment, the primary loops 600 are connected side-by-side, leaving no or negligible spacing between adjacent primary loops.

The secondary loops 800 are aligned with each other to form a looped structure that can fit into the annulus of a heart valve. In the looped structure formed by the secondary loops 800, the proximal portions 808 of the secondary loops 800 are aligned along a third radial plane, and the distal portions 812 of the secondary loops 800 are aligned along a fourth radial plane.

In exemplary embodiments, the secondary loops 800 are connected to the primary loops 600 to form an integral valve prosthesis. In the exemplary embodiment illustrated in FIGS. 10 and 11, the secondary loops 800 are disposed within and/or nested within the primary loops 600. In an exemplary embodiment, the centers of the mid portions 602 of the primary loops 600 and the mid portions 802 of the secondary loops 800 are aligned along a centerline C. The entire mid portions 802 of the secondary loops 800 may fit within the longer mid portions 602 of the primary loops 600.

In an exemplary embodiment, each secondary loop 800 may be connected to the primary loop 600 that the secondary loop is disposed within. In an exemplary embodiment, there is a amount of space between each secondary loop 800 and the corresponding primary loop 600 to which the secondary loop is connected. In another exemplary embodiment, there is no or negligible spacing between each secondary loop 800 and the corresponding primary loop 600 to which the secondary loop is connected.

In another exemplary embodiment, the secondary loops 800 may be aligned with each other and connected side-by-side to form a looped structure. In an exemplary embodiment, the secondary loops 800 are connected side-by-side, leaving an amount of spacing between adjacent secondary loops. In another exemplary embodiment, the secondary loops 800 are connected side-by-side, leaving no or negligible spacing between adjacent secondary loops.

FIG. 11 illustrates a perspective view of the exemplary loops of FIG. 10 where at least a portion of the surface of the primary loops 600 and/or the secondary loops 800 is covered by a tissue and/or non-tissue graft material 1106 (e.g., PS base woven or braided depending on end use applications and rate of tissue growth).

FIG. 12 illustrates a perspective view of an exemplary configuration of a valve prosthesis in which secondary loops 900 (as illustrated in FIG. 9) are disposed within and/or nested within primary loops 700 (as illustrated in FIG. 7), as configured for deployment in the posterior region of a heart valve. The primary loops 700 are aligned with each other and connected side-by-side to form a looped structure that can fit into the annulus of a heart valve. In the looped structure formed by the primary loops 700, the proximal portions 708 of the primary loops 700 are aligned along a first radial plane. In an exemplary embodiment, the primary loops 700 are connected side-by-side, leaving an amount of spacing between adjacent primary loops. In another exemplary embodiment, the primary loops 700 are connected side-by-side, leaving no or negligible spacing between adjacent primary loops.

The secondary loops 900 are aligned with each other to form a looped structure that can fit into the annulus of a heart valve. In the looped structure formed by the secondary loops 900, the proximal portions 908 of the secondary loops 900 are aligned along a first radial plane.

In exemplary embodiments, the secondary loops 900 are connected to the primary loops 700 to form an integral valve prosthesis. In the exemplary embodiment illustrated in FIGS. 12 and 13, the secondary loops 900 are disposed within and/or nested within the primary loops 700. In an exemplary embodiment, the centers of the mid portions 702 of the primary loops 700 and the mid portions 902 of the secondary loops 900 are aligned along a centerline C. The entire mid portions 902 of the secondary loops 900 may fit within the longer mid portions 702 of the primary loops 700.

In an exemplary embodiment, each secondary loop 900 may be connected to the primary loop 700 that the secondary loop is disposed within. In an exemplary embodiment, there is a amount of space between each secondary loop 900 and the corresponding primary loop 700 to which the secondary loop is connected. In another exemplary embodiment, there is no or negligible spacing between each secondary loop 900 and the corresponding primary loop 700 to which the secondary loop is connected.

In another exemplary embodiment, the secondary loops 900 may be aligned with each other and connected side-by-side to form a looped structure. In an exemplary embodiment, the secondary loops 900 are connected side-by-side, leaving an amount of spacing between adjacent secondary loops. In another exemplary embodiment, the secondary loops 900 are connected side-by-side, leaving no or negligible spacing between adjacent secondary loops.

FIG. 13 illustrates a perspective view of the exemplary loops of FIG. 12 where at least a portion of the surface of the primary loops 700 and/or the secondary loops 900 is covered by a tissue and/or non-tissue graft material 1306 (e.g., PS base woven or braided depending on end use applications and rate of tissue growth).

In other exemplary embodiments illustrated in FIGS. 14-17, the primary loops and the secondary loops are alternately connected side-by-side in series to form a looped structure formed of alternating primary and secondary loops that fits into a heart valve annulus and that supports the valve prosthesis against the annulus of the heart valve. That is, each primary loop is connected at each side to a secondary loop, and each secondary loop is connected at each sides to a primary loop.

FIG. 14 illustrates a perspective view of an exemplary configuration of a valve prosthesis in which secondary loops 800 (as illustrated in FIG. 8) and primary loops 600 (as illustrated in FIG. 6) are disposed alternately in a side-by-side manner, as configured for deployment in the posterior region of a heart valve. The primary loops 600 and secondary loops 800 are aligned with each other and connected side-by-side to form a looped structure that can fit into the annulus of a heart valve. Each primary loop 600 is connected at each side to a secondary loop 800, and each secondary loop 800 is connected at each side to a primary loop 600 to form an integral valve prosthesis.

In the looped structure formed by the primary loops 600 and the secondary loops 800, the proximal portions 608 of the primary loops 600 are aligned along a first radial plane, the distal portions 612 of the primary loops 600 are aligned along a second radial plane, the proximal portions 808 of the secondary loops 800 are aligned along a third radial plane, and the distal portions 812 of the secondary loops 800 are aligned along a fourth radial plane.

In an exemplary embodiment, the loops are connected side-by-side, leaving an amount of spacing between adjacent loops. In another exemplary embodiment, the loops are connected side-by-side, leaving no or negligible spacing between adjacent loops.

In an exemplary embodiment, the centers of the mid portions 602 of the primary loops 600 and the mid portions 802 of the secondary loops 800 are aligned along a centerline C.

FIG. 15 illustrates a perspective view of the exemplary loops of FIG. 14 where at least a portion of the surface of the primary loops 600 and/or the secondary loops 800 is covered by a tissue and/or non-tissue graft material 1506 (e.g., PS base woven or braided depending on end use applications and rate of tissue growth).

FIG. 16 illustrates a perspective view of an exemplary configuration of a valve prosthesis in which secondary loops 900 (as illustrated in FIG. 9) and primary loops 700 (as illustrated in FIG. 7) are disposed alternately in a side-by-side manner, as configured for deployment in the anterior region of a heart valve. The primary loops 700 and secondary loops 900 are aligned with each other and connected side-by-side to form a looped structure that can fit into the annulus of a heart valve. Each primary loop 700 is connected at each side to a secondary loop 900, and each secondary loop 900 is connected at each side to a primary loop 700 to form an integral valve prosthesis.

In the looped structure formed by the primary loops 700 and the secondary loops 900, the proximal portions 708 of the primary loops 700 are aligned along a first radial plane, and the proximal portions 908 of the secondary loops 900 are aligned along a second radial plane.

In an exemplary embodiment, the loops are connected side-by-side, leaving an amount of spacing between adjacent loops. In another exemplary embodiment, the loops are connected side-by-side, leaving no or negligible spacing between adjacent loops.

In an exemplary embodiment, the centers of the mid portions 702 of the primary loops 700 and the mid portions 902 of the secondary loops 900 are aligned along a centerline C.

FIG. 17 illustrates a perspective view of the exemplary loops of FIG. 16 where at least a portion of the surface of the primary loops 700 and/or the secondary loops 900 is covered by a tissue and/or non-tissue graft material 1706 (e.g., PS base woven or braided depending on end use applications and rate of tissue growth).

In some exemplary embodiments, an anterior portion of the valve prosthesis for deployment in the anterior region of a heart valve is configured in the same way as a posterior portion of the valve prosthesis for deployment in the posterior region of a heart valve. In other exemplary embodiments, the anterior and posterior portions of the valve prosthesis are configured differently.

In an exemplary embodiment, the anterior and posterior regions of the valve prosthesis have the same structural configuration. In exemplary embodiments suitable for application in mitral and tricuspid valves of the heart, the valve prosthesis is configured differently in its anterior region and its posterior region. In exemplary embodiments illustrated in FIGS. 18A, 18B, 19A and 19B, the anterior and posterior regions of the valve prosthesis may be configured such that the radial extensions of the proximal and distal portions of the loops are configured differently for the anterior and posterior regions. In exemplary embodiments illustrated in FIGS. 18A, 18B, 19A and 19B, the anterior and posterior regions of the valve prosthesis may be configured such that the primary and/or secondary loops in the anterior regions have different structural configurations than the primary and/or secondary loops in the posterior regions.

FIG. 18A illustrates a top view of an exemplary valve prosthesis 1800 in which an anterior portion 1802 for deployment in the anterior region of a heart valve is configured differently from a posterior portion 1804 for deployment in the posterior region of a heart valve. The anterior portion 1802 includes a series of primary loops 700 as illustrated in FIG. 7 connected side-by-side. The posterior portion 1804 includes a series of primary loops 600 as illustrated in FIG. 6 connected side-by-side and a series of secondary loops 800 as illustrated in FIG. 8 connected side-by-side. The secondary loops 800 are provided within and/or attached to the primary loops 600 as illustrated in FIG. 10. In an exemplary embodiment, the mid portions of the primary loops 600 may be connected to the mid portions of the adjacent primary loops to form a substantially circular arrangement (as viewed from the top of the valve prosthesis) to provide uniform support at the valve annulus. In an exemplary embodiment, the mid portions of the secondary loops 800 may be connected to the mid portions of the adjacent secondary loops to form a substantially semi-circular arrangement (as viewed from the top of the valve prosthesis).

In an exemplary embodiment, the primary and/or secondary loops of the valve prosthesis may include sub-annular loops, drapes, anchors, barbs, etc., in only the posterior portion 1804 for aortic and left outflow track and overall anterior prosthesis area protection, while providing clinically relevant fixation. In an exemplary embodiment, a skirted area may be included only in the posterior portion 1804 with/without primary sub-valvular loops. A skirted area may have a greater diameter (taken from the center of the valve annulus) than and may extend radially outwardly from a portion of the looped element below the skirted section along the longitudinal axis L.

Figure 18B:
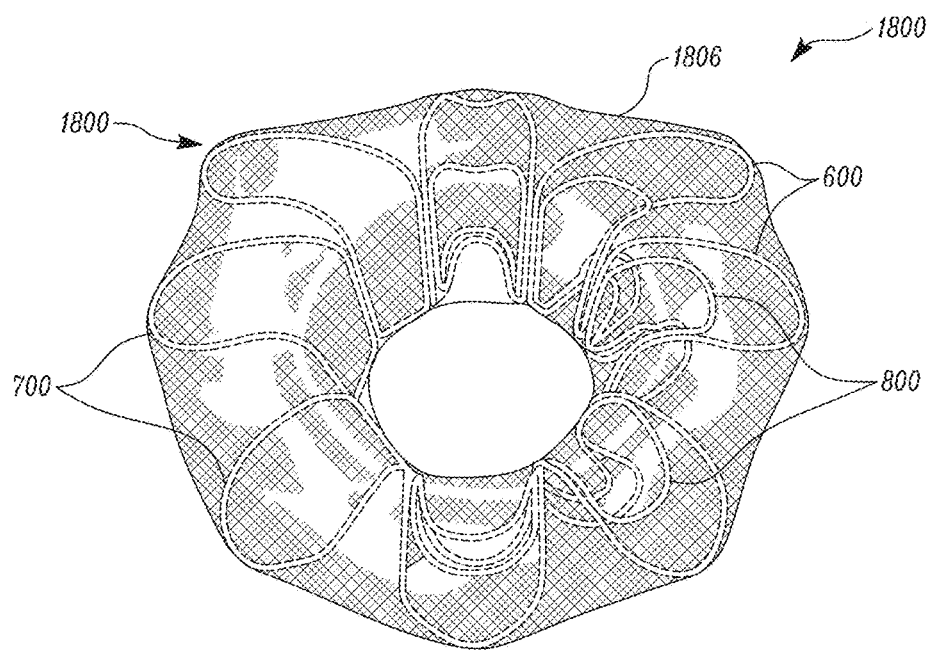
FIG. 18B illustrates a top view of the valve prosthesis of FIG. 18A as covered with a tissue and/or non-tissue graft material, in its deployed state.

FIG. 18B illustrates a top view of the valve prosthesis 1800 of FIG. 18A as covered with a tissue and/or non-tissue graft material 1806 (e.g., PS base woven or braided depending on end use applications and rate of tissue growth), in its deployed state.

Figure 19A:
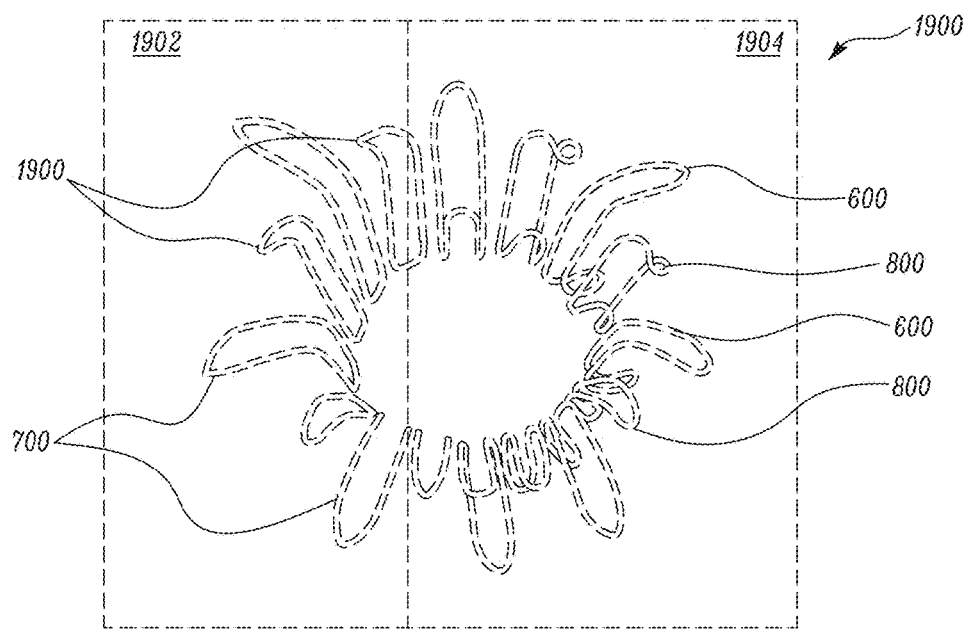
FIG. 19A illustrates a top view of another exemplary valve prosthesis in which an anterior portion for deployment in the anterior region of a heart valve is configured differently from a posterior portion for deployment in the posterior region of a heart valve.

FIG. 19A illustrates a top view of an exemplary valve prosthesis 1900 in which an anterior portion 1902 for deployment in the anterior region of a heart valve is configured differently from a posterior portion 1904 for deployment in the posterior region of a heart valve. The anterior portion 1902 includes primary loops 700 as illustrated in FIG. 7 and secondary loops 900 as illustrated in FIG. 9. The primary loops 700 and secondary loops 900 are connected side-by-side in an alternating manner as illustrated in FIG. 16. The posterior portion 1904 includes primary loops 600 as illustrated in FIG. 6 and secondary loops 800 as illustrated in FIG. 8. The primary loops 600 and secondary loops 800 are connected side-by-side in an alternating manner as illustrated in FIG. 14. In an exemplary embodiment, the mid portions of the loops 600/800 may be connected to the mid portions of the adjacent loops to form a substantially circular arrangement (as viewed from the top of the valve prosthesis) to provide uniform support at the valve annulus.

Figure 19B:
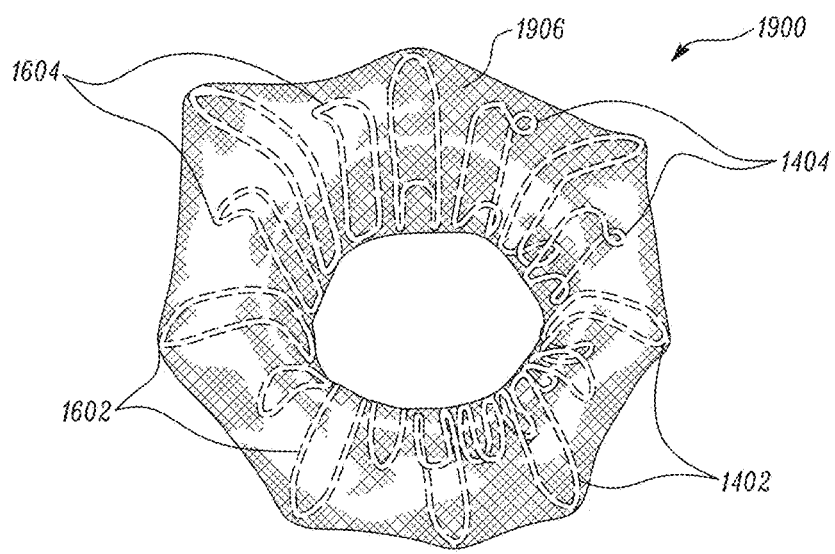
FIG. 19B illustrates a top view of the valve prosthesis of FIG. 19A as covered with a tissue and/or non-tissue graft material, in its deployed state.

FIG. 19B illustrates a top view of the valve prosthesis 1900 of FIG. 19A as covered with a tissue and/or non-tissue graft material 1906 (e.g., PS base woven or braided depending on end use applications and rate of tissue growth), in its deployed state.

FIG. 20 illustrates a longitudinal section taken through a mitral valve in which the exemplary valve prosthesis 1900 of FIGS. 19A and 19B is deployed at the annulus of the mitral valve and where at least a portion of the surface of the prosthesis is covered by a tissue and/or non-tissue graft material 2002 (e.g., PS base woven or braided depending on end use applications and rate of tissue growth).

FIG. 21 illustrates a longitudinal section taken through a mitral valve in which the exemplary valve prosthesis 1900 of FIGS. 19A and 19B is deployed at the annulus of the mitral valve.

FIG. 22 illustrates a longitudinal section taken through the mitral valve shown in FIGS. 20 and 21 where the valve prosthesis 1900 is provided with radio-opaque markers 2004. FIG. 22A illustrates a longitudinal section taken through the mitral valve shown in FIGS. 20 and 21 where the valve prosthesis 2006 is provided with radio-opaque markers 2004.

As illustrated in FIGS. 20-22A, the valve prosthesis 2000 is expanded when deployed in a heart valve annulus and is safely and securely held in place by the combined configuration of the primary and secondary loops. The spacing between the loop elements and within each loop element in the valve prosthesis may be configured such that the valve prosthesis is compliant and conforms to the shape and the anatomy of the valve annulus in a natural manner.

In an exemplary embodiment, at least a portion of the outer surface of the primary loops is covered by a tissue and/or non-tissue graft material (e.g., PS base woven or braided depending on end use applications and rate of tissue growth) to provide a radial seal around the valve prosthesis to prevent paravalvular leaks. The covered portions on the primary loops may be the bottom of the mid portion of the primary loops. In an exemplary embodiment, at least a portion of the outer surface of the secondary loops is covered by a tissue and/or non-tissue graft material (e.g., PS base woven or braided depending on end use applications and rate of tissue growth) to provide a radial seal around the valve prosthesis to prevent paravalvular leaks. The covered portions on the secondary loops may be the bottom portion of the secondary loops. The non-tissue graft material (e.g., PS base woven or braided depending on end use applications and rate of tissue growth) could be impregnated with one or more tissue growth agents in desired areas of the valve prosthesis. This encourages faster tissue growth which, in turn, would allow for enhanced fastening of the valve prosthesis to the cardiac anatomy and lower fatigue of the valve prosthesis.

In exemplary embodiments, one or more radio-opaque markers may be placed on the primary and/or secondary loops to facilitate in positioning and deploying the valve prosthesis by a delivery system. The radio-opaque markers may be placed only in the posterior region of the valve prosthesis, only in the anterior region of the valve prosthesis, or in both the posterior and anterior regions. Exemplary markers may include, but are not limited to, pad printed markers or woven monofilament markers.

Figure 23:
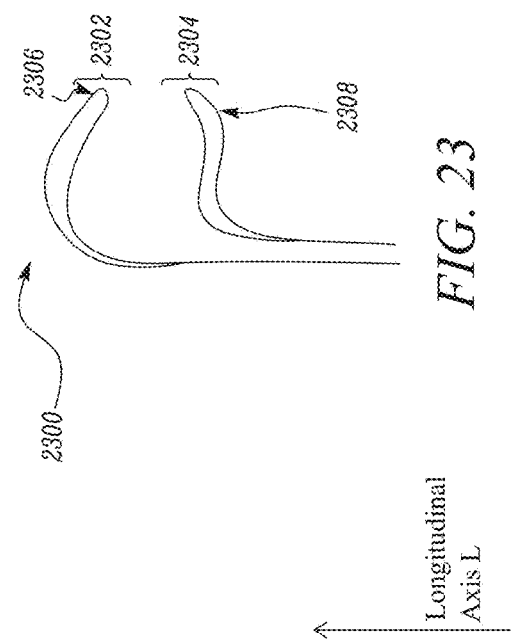
FIG. 23 illustrates a longitudinal sectional view taken through an exemplary valve prosthesis.

FIG. 23 is a side view of a single primary loop 2300 having a proximal portion 2302 ending in a terminal tip 2306 and a distal sub-annular portion 2304 ending in a terminal tip 2308. A valve housing portion 2310 may extend below the distal sub-annular portion 2304. In an exemplary embodiment, multiple primary loops 2300 are aligned with each other and connected side-by-side in series to form a looped structure that fits into a heart valve annulus and that supports the valve prosthesis against the annulus of the heart valve. In the looped structure formed by the primary loops 2300, the proximal portions 2302 of the primary loops 2300 are aligned along a first radial plane, and the distal sub-annular portions 2304 of the primary loops 2300 are aligned along a second radial plane.

The proximal portion 2302 is curved and extends radially and outwardly away from the longitudinal axis L of the valve prosthesis in an arcuate manner. The tip 2306 of the proximal portion 2302 curves downwardly to some extent in an exemplary embodiment. The proximal portion 2302 is configured to be positioned just above the annular ring of the heart valve such that the arcuate shape of the proximal portion 2302 provides a fastening mechanism for radial fastening of the valve prosthesis to the atrium or to an upper portion of the heart valve annulus. The fastening mechanism also provides an outer radial force against the top of the heart valve annulus which securely attaches the valve prosthesis to the heart valve annulus. In the looped structure formed by multiple primary loops 2300, the proximal portions 2302 adapt to the shape of the annulus of a heart valve and provide natural coverage and a complete radial seal that eliminates paravalvular leaks. In an exemplary embodiment, the tip 2306 of the proximal portion 2302 may be adjustable and may include a sharp end, e.g., a barb, to penetrate the valve annulus to further secure the valve prosthesis to the annulus.

The distal sub-annular portion 2304 is curved and extends radially and outwardly away from the longitudinal axis L of the valve prosthesis in an arcuate manner. The tip 2308 of the distal portion 2304 curves upwardly to some extent in an exemplary embodiment. The distal portion 2304 is configured to be positioned under the valve leaflets such that the arcuate shape of the distal portion 2304 provides a fastening mechanism for radial fastening of the valve prosthesis to the ventricle below the valve leaflets. The fastening mechanism also provides an outer radial force against the valve annulus which securely attaches the valve prosthesis to the valve annulus and that provides a radial seal between the outer surface of the valve prosthesis and the annulus of a heart valve to prevent paravalvular leaks.

In exemplary embodiments, the proximal portions 2302 and/or the distal sub-annular portions 2304 of the primary loops 2300 are flexible, and the curvature and mushroom shape formed by a looped series of primary loops 2300 are automatically adjustable due to the flexible nature of the proximal and/or distal portions. This adjustability allows for adjusting the shape of the annulus formed by the valve prosthesis. This allows an exemplary valve prosthesis to conform to the annular shape of any heart valve. That is, a looped series of connected primary loops may be placed in any heart valve annulus, and the compliant nature of the loops will allow the prosthesis to conform to the particular structure of the valve annulus. As such, one size of the valve prosthesis may fit any annulus and this may reduce the overall profile for a delivery device and may, consequently, reduce the access puncture point and improve deliverability and tactile feeling of the valve prosthesis. In addition, a clinically relevant smaller valve annulus size may have improved shelf life.

Figure 31:
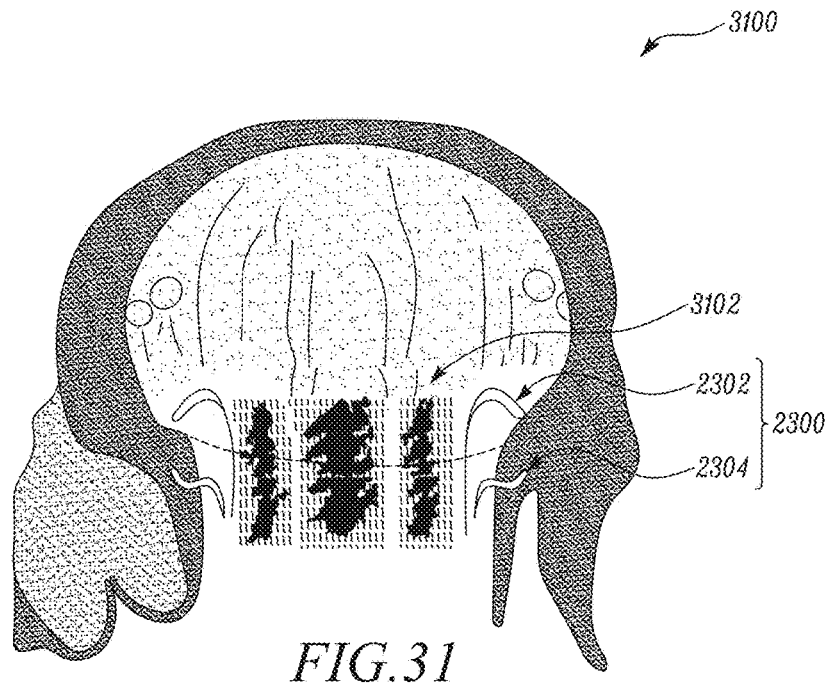
FIG. 31 illustrates a longitudinal sectional view taken through the exemplary valve prosthesis of FIG. 23 as deployed in the annulus of the mitral valve.

FIG. 31 illustrates a longitudinal sectional taken through a heart 3100 in which an exemplary valve prosthesis 3102 formed by a looped series of the primary loops 2300 (illustrated in FIG. 23) is disposed in the annulus of the mitral valve.

Figure 24:
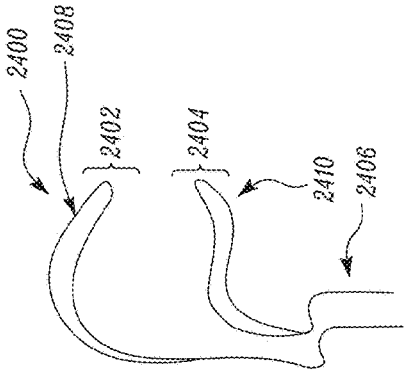
FIG. 24 illustrates an exemplary valve prosthesis with a mid portion and/or a distal portion extending below the annular ring that is skirted.

FIG. 24 is a side view of a single primary loop 2400 having a proximal portion 2402 ending in a terminal tip 2408 and a distal sub-annular portion 2404 ending in a terminal tip 2410. An exemplary valve prosthesis formed by the loops of FIG. 24 includes a skirted section 2406 that has a larger diameter than the valve housing portion 2310 illustrated in FIG. 23, provided distal to the primary loops 2400. That is, the skirted section 2406 extending downward from the portions 2402 and 2404 along the longitudinal axis L has a greater diameter (taken from the center of the valve annulus) than and extends radially outwardly from a portion below the skirted section along the longitudinal axis L.

Figure 25:
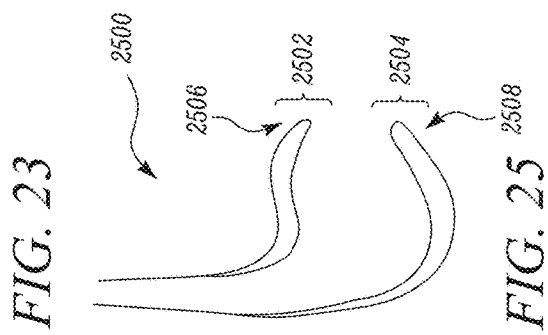
FIG. 25 illustrates a longitudinal section view taken through an exemplary valve prosthesis that is an inverted version of the exemplary valve prosthesis of FIG. 23.

FIG. 25 is a side view of a single primary loop 2500 that is an inverted version of the exemplary primary loop 2300 of FIG. 23. The primary loop 2500 has a proximal portion 2502 ending in a terminal tip 2506 and a distal portion 2504 ending in a terminal tip 2508. A valve housing portion 2510 may extend above the proximal portion 2502.

The proximal portion 2502 is curved and extends radially and outwardly away from the longitudinal axis L of the valve prosthesis in an arcuate manner. The tip 2506 of the proximal portion 2502 curves downwardly to some extent in an exemplary embodiment. The proximal portion 2502 is configured to be positioned just above the annular ring of the heart valve such that the arcuate shape of the proximal portion 2502 provides a fastening mechanism for radial fastening of the valve prosthesis to the atrium or to an upper portion of the heart valve annulus. The fastening mechanism also provides an outer radial force against the top of the heart valve annulus which securely attaches the valve prosthesis to the heart valve annulus. In an exemplary embodiment, the tip 2506 of the proximal portion 2502 may be adjustable and may include a sharp end, e.g., a barb, to penetrate the valve annulus to further secure the valve prosthesis to the annulus.

The distal portion 2504 is curved and extends radially and outwardly away from the longitudinal axis L of the valve prosthesis in an arcuate manner. The tip 2508 of the distal portion 2504 curves upwardly to some extent in an exemplary embodiment. The distal portion 2504 is configured to be positioned under the valve leaflets such that the arcuate shape of the distal portion 2504 provides a fastening mechanism for radial fastening of the valve prosthesis to the ventricle below the valve leaflets. The fastening mechanism also provides an outer radial force against the valve annulus which securely attaches the valve prosthesis to the valve annulus and that provides a radial seal between the outer surface of the valve prosthesis and the annulus of a heart valve to prevent paravalvular leaks. In an exemplary embodiment, the tip 2508 of the proximal portion 2504 may be adjustable and may include a sharp end, e.g., a barb, to penetrate the valve annulus to further secure the valve prosthesis to the annulus.

In exemplary embodiments, the proximal portions 2502 and/or the distal sub-annular portions 2504 of the primary loops 2500 are flexible, and the curvature and mushroom shape formed by a looped series of primary loops 2500 are automatically adjustable due to the flexible nature of the proximal and/or distal portions. This adjustability allows for adjusting the shape of the annulus formed by the valve prosthesis. This allows an exemplary valve prosthesis to conform to the annular shape of any heart valve. That is, a looped series of connected primary loops may be placed in any heart valve annulus, and the compliant nature of the loops will allow the prosthesis to conform to the particular structure of the valve annulus. As such, one size of the valve prosthesis may fit any annulus and this may reduce the overall profile for a delivery device and may, consequently, reduce the access puncture point and improve deliverability and tactile feeling of the valve prosthesis. In addition, a clinically relevant smaller valve annulus size may have improved shelf life.

Figure 33:
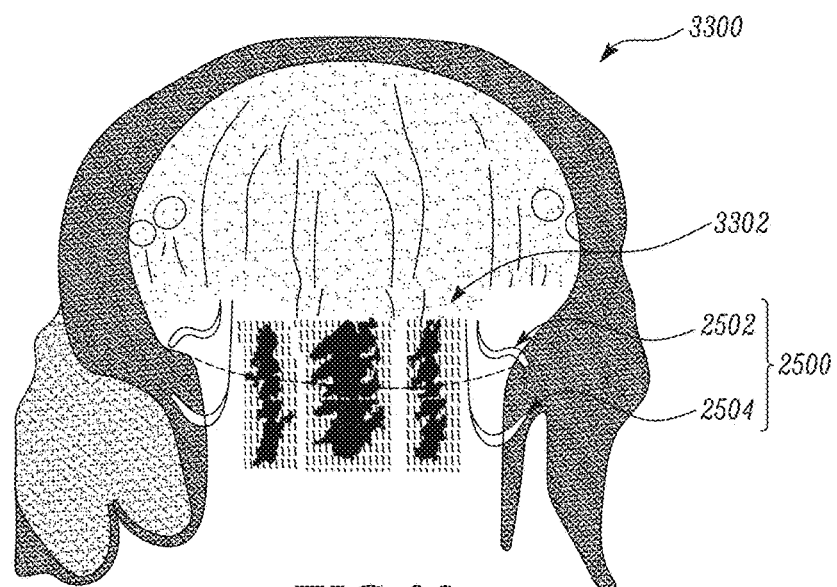
FIG. 33 illustrates a longitudinal sectional view taken through the exemplary valve prosthesis of FIG. 25 as deployed in the annulus of the mitral valve.

FIG. 33 illustrates a longitudinal sectional taken through a heart 3300 in which an exemplary valve prosthesis 3302 formed by a looped series of the primary loops 2500 (illustrated in FIG. 25) is disposed in the annulus of the mitral valve.

Figure 26:
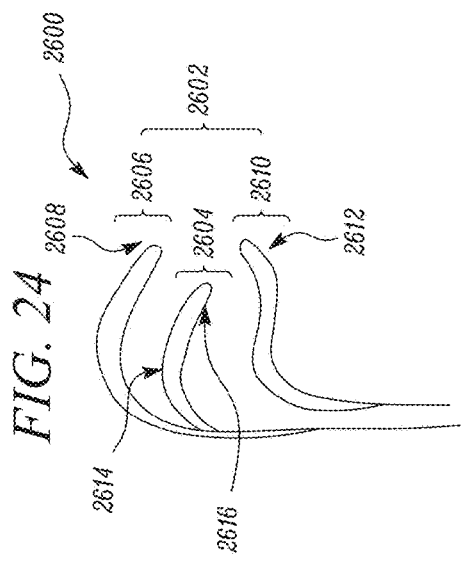
FIG. 26 illustrates a longitudinal sectional view taken through another exemplary valve prosthesis.

FIG. 26 is a side view of a single pairing 2600 of a primary loop 2602 and a secondary loop 2604. The primary loop 2602 has a proximal portion 2606 ending in a terminal tip 2608 and a distal sub-annular portion 2610 ending in a terminal tip 2612. The secondary loop 2604 has a proximal portion 2614 ending in a terminal tip 2616. A valve housing portion 2618 may extend below the distal sub-annular portion 2610.

In an exemplary embodiment, multiple primary loops 2602 are aligned with each other and connected side-by-side in series to form a looped structure that fits into the heart valve annulus and that supports the valve prosthesis against the annulus of the heart valve. Multiple secondary loops 2604 are aligned with each other and connected side-by-side in series to form a looped structure that fits into the heart valve annulus and that supports the valve prosthesis against the annulus of the heart valve. The secondary loops 2604 may be provided within the primary loops 2602 in an exemplary embodiment.

In the looped structure formed by the primary loops 2602 and the secondary loops 2604, the proximal portions 2606 of the primary loops 2602 are aligned along a first radial plane, the proximal portions 2614 of the secondary loops 2604 are aligned along a second radial plane below the first radial plane, and the distal sub-annular portions 2610 of the primary loops 2602 are aligned along a third radial plane below the first and second radial planes.

The proximal portion 2606 of the primary loop 2602 and the proximal portion 2614 of the secondary loop 2604 are curved and extend radially and outwardly away from the longitudinal axis L of the valve prosthesis in an arcuate manner. The tip 2608 of the proximal portion 2606 of the primary loop 2602 and the tip 2616 of the proximal portion 2614 of the secondary loop 2604 curve downwardly to some extent in an exemplary embodiment. The proximal portion 2606 of the primary loop 2602 and the proximal portion 2614 of the secondary lop 2604 are configured to be positioned just above the annular ring of the heart valve such that the arcuate shape of the proximal portions provides a fastening mechanism for radial fastening of the valve prosthesis to the atrium or to an upper portion of the heart valve annulus. The fastening mechanism also provides an outer radial force against the top of the heart valve annulus which securely attaches the valve prosthesis to the heart valve annulus.

The distal sub-annular portion 2610 of the primary loop 2602 is curved and extends radially and outwardly away from the longitudinal axis L of the valve prosthesis in an arcuate manner. The tip 2612 of the distal portion 2610 curves upwardly to some extent in an exemplary embodiment. The distal portion 2610 is configured to be positioned under the valve leaflets such that the arcuate shape of the distal portion 2610 provides a fastening mechanism for radial fastening of the valve prosthesis to the ventricle below the valve leaflets. The fastening mechanism also provides an outer radial force against the valve annulus which securely attaches the valve prosthesis to the valve annulus and that provides a radial seal between the outer surface of the valve prosthesis and the annulus of a heart valve to prevent paravalvular leaks.

Figure 32:
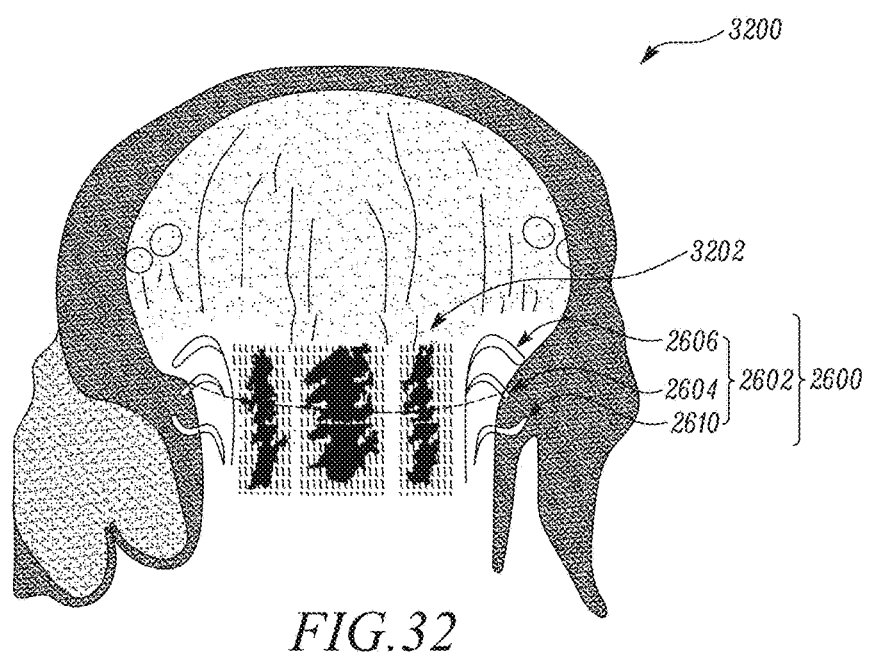
FIG. 32 illustrates a longitudinal sectional view taken through the exemplary valve prosthesis of FIG. 26 as deployed in the annulus of the mitral valve.

FIG. 32 illustrates a longitudinal sectional taken through a heart 3200 in which an exemplary valve prosthesis 3202 formed by a looped series of the primary loops 2602 (illustrated in FIG. 26) and a looped series of the secondary loops 2604 (illustrated in FIG. 26) is disposed in the annulus of the mitral valve.

FIG. 27 is a side view of a single pairing 2700 of a primary loop 2702 and a secondary loop 2704. The primary loop 2702 has a proximal portion 2706 ending in a terminal tip 2708 and a distal sub-annular portion 2708 ending in a terminal tip 2712. The secondary loop 2704 has a proximal portion 2714 ending in a terminal tip 2716. An exemplary valve prosthesis formed by the loops of FIG. 27 includes a skirted section 2718, that has a larger diameter than the embodiment illustrated in FIG. 26, provided distal to the primary and secondary loops. That is, the skirted section 2718 extending downward from the portion 2702 along the longitudinal axis L has a greater diameter (taken from the center of the valve annulus) than and extends radially outwardly from a portion below the skirted section along the longitudinal axis L.

FIG. 28 is a side view of a single pairing 2800 of a primary loop 2802 and a secondary loop 2804 that is an inverted version of the exemplary primary loop 2600 of FIG. 26. The primary loop 2802 has a proximal portion 2806 ending in a terminal tip 2808 and a distal sub-annular portion 2810 ending in a terminal tip 2812. The secondary loop 2804 has a distal portion 2814 ending in a terminal tip 2816.

The proximal portion 2806 of the primary loop 2802 is curved and extends radially and outwardly away from the longitudinal axis L of the valve prosthesis in an arcuate manner. The tip 2808 of the proximal portion 2806 of the primary loop 2806 curves downwardly to some extent in an exemplary embodiment. The proximal portion 2806 of the primary loop 2802 is configured to be positioned just above the annular ring of the heart valve such that the arcuate shape of the proximal portions provides a fastening mechanism for radial fastening of the valve prosthesis to the atrium or to an upper portion of the heart valve annulus. The fastening mechanism also provides an outer radial force against the top of the heart valve annulus which securely attaches the valve prosthesis to the heart valve annulus.

The distal sub-annular portion 2810 of the primary loop 2802 and the distal portion 2814 of the secondary loop 2804 are curved and extend radially and outwardly away from the longitudinal axis L of the valve prosthesis in an arcuate manner. The tip 2812 of the distal portion 2810 of the primary loop 2802 and the tip 2816 of the distal portion 2814 of the secondary loop 2804 curve upwardly to some extent in an exemplary embodiment. The distal portions 2810 and 2814 are configured to be positioned under the valve leaflets such that the arcuate shape of the distal portions provides a fastening mechanism for radial fastening of the valve prosthesis to the ventricle below the valve leaflets. The fastening mechanism also provides an outer radial force against the valve annulus which securely attaches the valve prosthesis to the valve annulus and that provides a radial seal between the outer surface of the valve prosthesis and the annulus of a heart valve to prevent paravalvular leaks.

Figure 34:
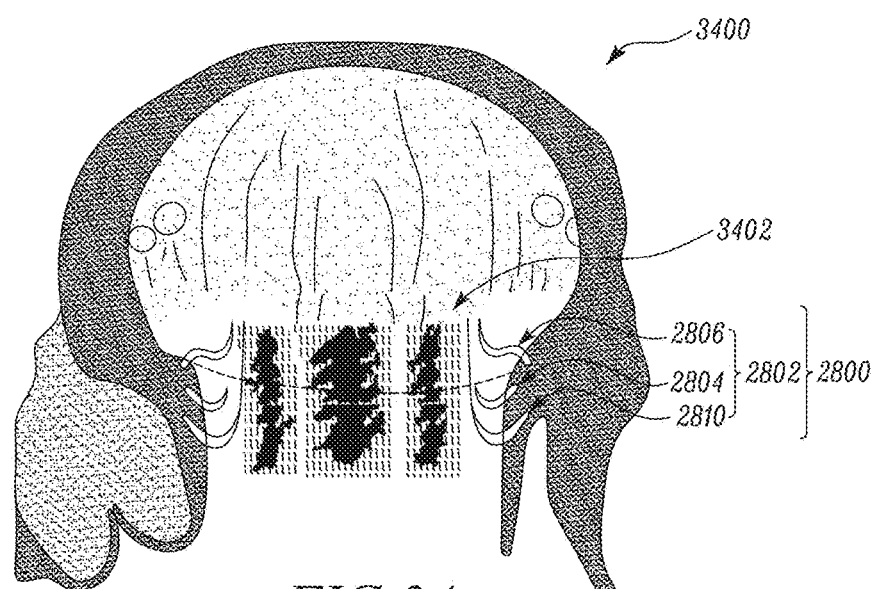
FIG. 34 illustrates a longitudinal sectional view taken through the exemplary valve prosthesis of FIG. 28 as deployed in the annulus of the mitral valve.

FIG. 34 illustrates a longitudinal sectional taken through a heart 3400 in which an exemplary valve prosthesis 3402 formed by a looped series of the primary loops 2800 (illustrated in FIG. 28) is disposed in the annulus of the mitral valve.

FIG. 29 is a side view of a loop element 2900 for a valve prosthesis having a proximal skirted region 2902 that extends above the annular ring and that fastens the valve prosthesis to the atrial wall, and a primary sub-annular loop 2904 that extends at or below the valve leaflets in the annular ring and that fastens the valve prosthesis to the annular wall or to the ventricle.

Figure 35:
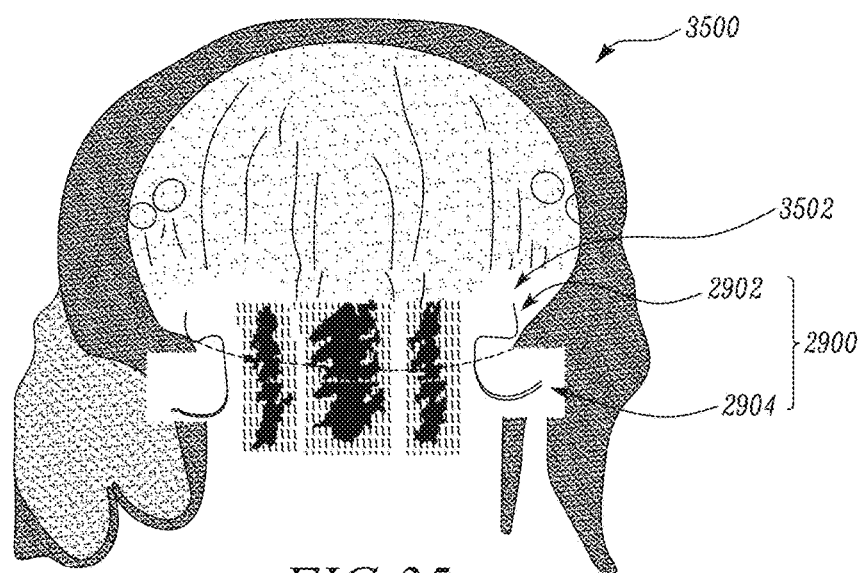
FIG. 35 illustrates a longitudinal sectional view taken through the exemplary valve prosthesis of FIG. 29 as deployed in the annulus of the mitral valve.

FIG. 35 illustrates a longitudinal sectional taken through a heart 3500 in which an exemplary valve prosthesis 3502 formed by a looped series of the loop elements 2900 (illustrated in FIG. 29) is disposed in the annulus of the mitral valve.

FIG. 30 is a side view of a loop element 3000 for a valve prosthesis having a proximal skirted region 3002 that extends above the annular ring and that fastens the valve prosthesis to the atrial wall, a primary sub-annular loop 3006 that extends at or below the valve leaflets in the annular ring and that fastens the valve prosthesis to the annular wall or to the ventricle, and a secondary sub-annular loop 3004 that extends at or below the valve leaflets in the annular ring and that fastens the valve prosthesis to the annular wall or to the ventricle. The secondary loop 3004 may be nested within the primary loop 3002 and may be disposed proximally above the primary loop 3002.

Figure 36:
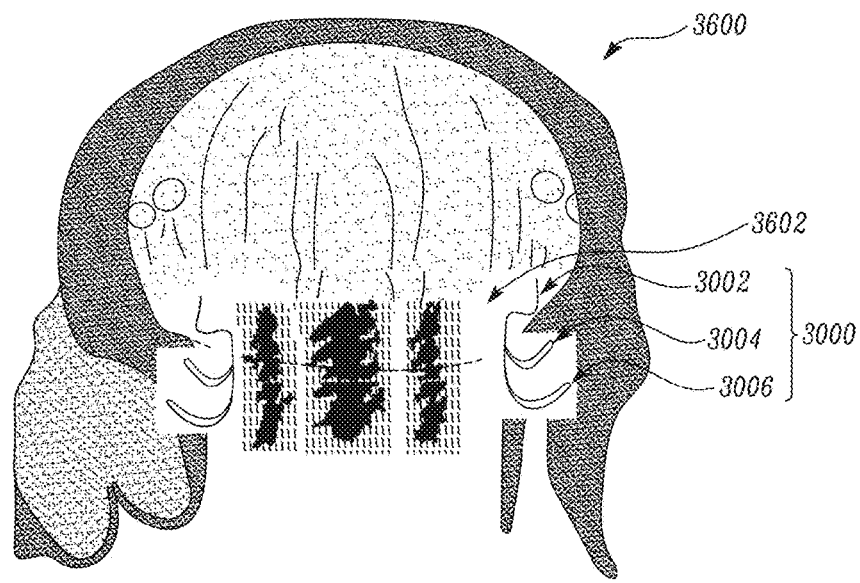
FIG. 36 illustrates a longitudinal sectional view taken through the exemplary valve prosthesis of FIG. 30 as deployed in the annulus of the mitral valve.

FIG. 36 illustrates a longitudinal sectional taken through a heart 3600 in which an exemplary valve prosthesis 3602 formed by a looped series of the loop elements 3000 (illustrated in FIG. 30) is disposed in the annulus of the mitral valve. Any portion of the surfaces of the loops of FIGS. 23-30 may be covered with a tissue and/or non-tissue graft material (e.g., PS base woven or braided depending on end use applications and rate of tissue growth). The loops may include fastening mechanisms including, but not limited to, barbs, anchors, fixations, spacers, drapes, etc.

Figure 37:
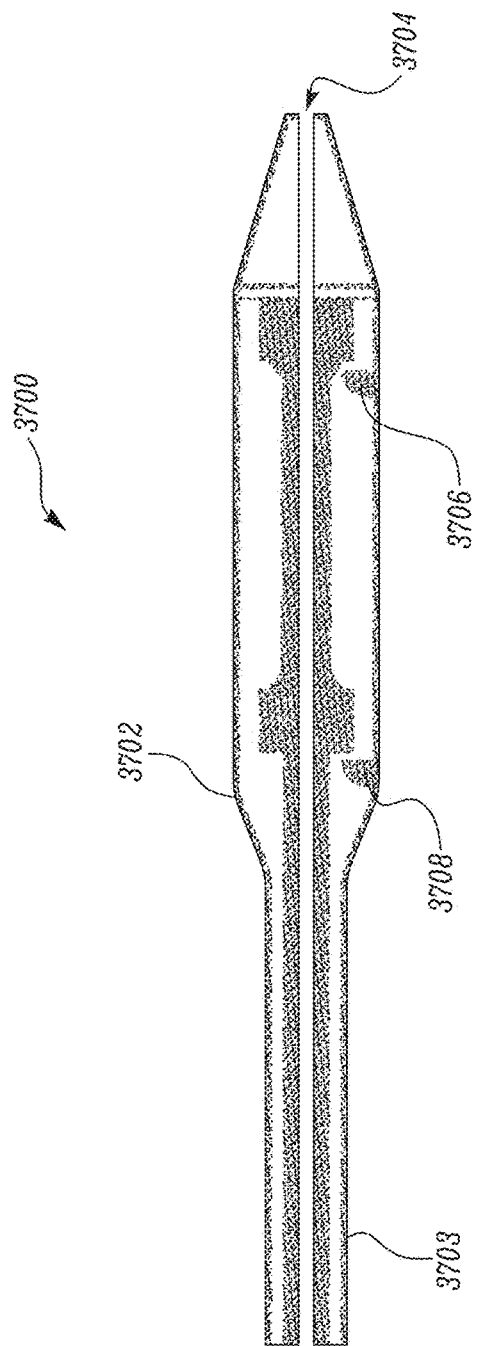
FIG. 37 illustrates an exemplary delivery device for delivering a valve prosthesis to the annulus of a heart valve.

FIG. 37A illustrates a top view of an exemplary valve prosthesis formed of the exemplary loops of FIG. 23 or FIG. 26, with one or more primary loops 4202 covered with a material layer 4204. FIG. 37B illustrates a top view of the exemplary valve prosthesis of FIG. 37A as deployed in a heart valve annulus. In some exemplary embodiments, the material may extend over and across a gap formed between the loops. In some exemplary embodiments, the material may extend over and across the loops, but not the gaps between the loops.

FIG. 37C illustrates a bottom view of an exemplary valve prosthesis formed of the exemplary loops of FIG. 23, showing distal portions of primary loops 4202 deployed under the heart valve annulus. In an exemplary embodiment, areas of the distal portion of the primary loops 4202 may be provided with a material layer 4204. In some exemplary embodiments, the primary loops may push the native annulus aside and reach into the top portions of the valve leaflets under the annulus. In the exemplary embodiment shown in FIG. 37C, primary loops are provided both in the posterior and anterior regions.

Figure 38:
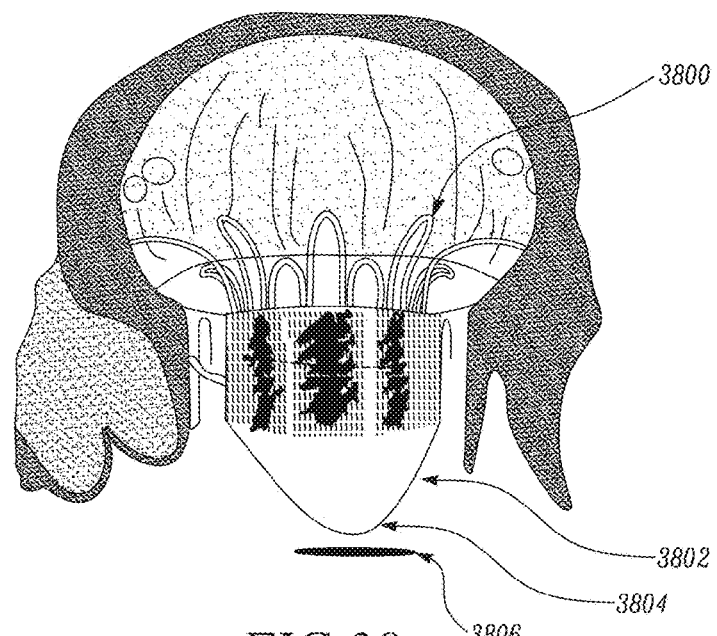
FIG. 38 illustrates an exemplary valve prosthesis formed of the exemplary loops of FIG. 23 used in replacing a mitral valve.

FIG. 38 illustrates an exemplary valve prosthesis formed of the exemplary loops of FIG. 23 used for replacing a mitral valve 4312 at a mitral annulus 4308. The prosthesis may form a new annulus 4306. The valve prosthesis is formed of the exemplary loops attached in a circular arrangement. Each of the primary loops may include a proximal portion 4302 (including, for example, one or more fixation or anchoring components 4310), a distal sub-annular portion 4314 (including, for example, one or more fixation or anchoring components), and a valve housing portion 4304.

Figure 39:
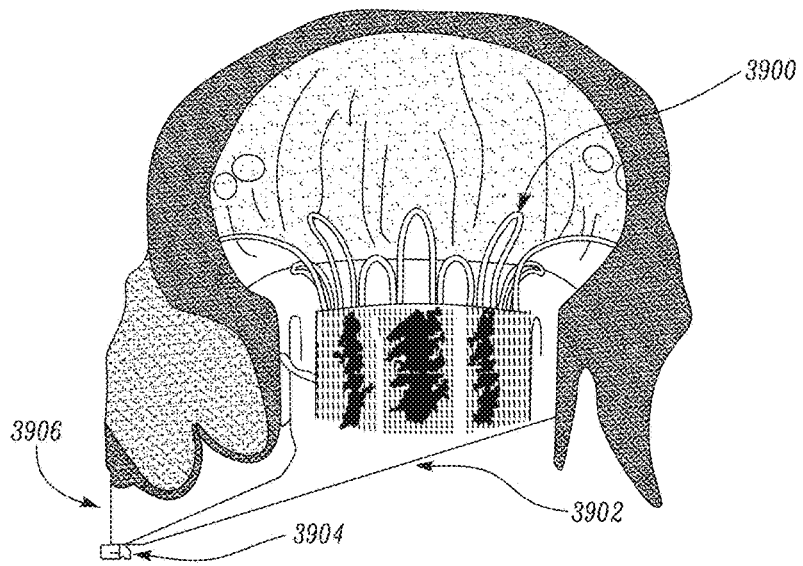
FIG. 39 illustrates a top view of an exemplary valve prosthesis of FIG. 26 deployed in a heart valve annulus showing primary and second loops above the annulus.

FIG. 39 illustrates a top view of an exemplary valve prosthesis of FIG. 26 deployed in a heart valve annulus showing proximal portions of primary loops 4402 and secondary loops 4404 above the native annulus.

Figure 40:
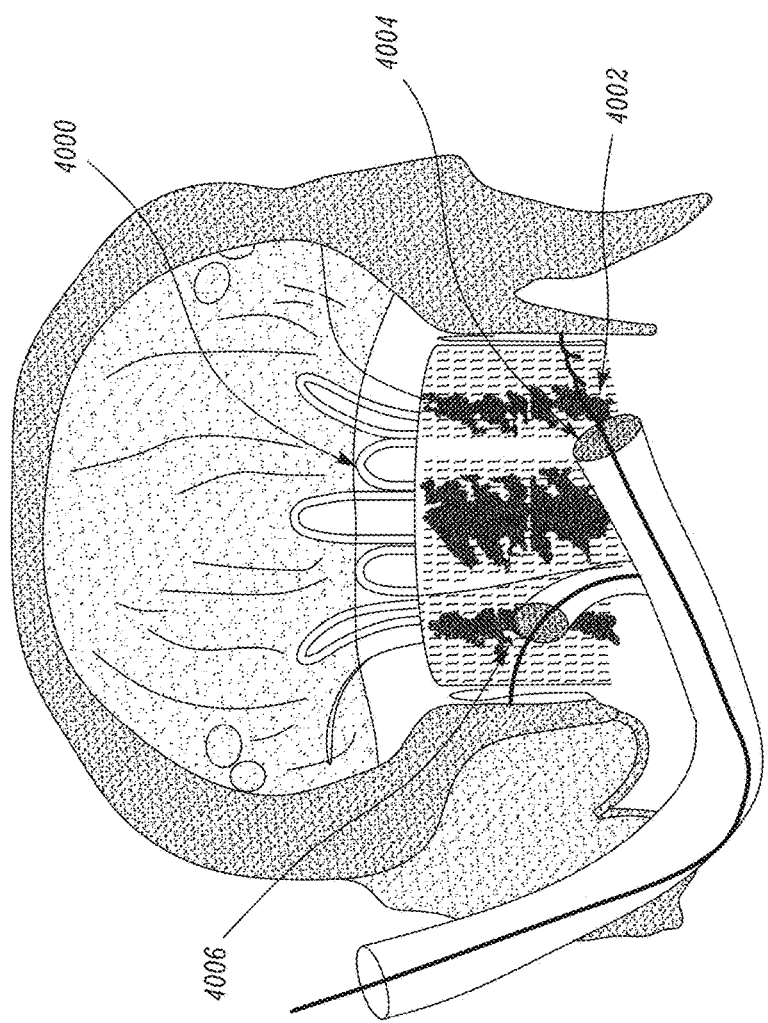
FIG. 40 illustrates a distal side view of an exemplary valve prosthesis showing primary and secondary loops.

FIG. 40 illustrates a distal side view of an exemplary valve prosthesis showing exemplary primary loops having a distal portion 4502 and a proximal portion 4504, and secondary loops having a proximal portion 4506.

Figure 41:
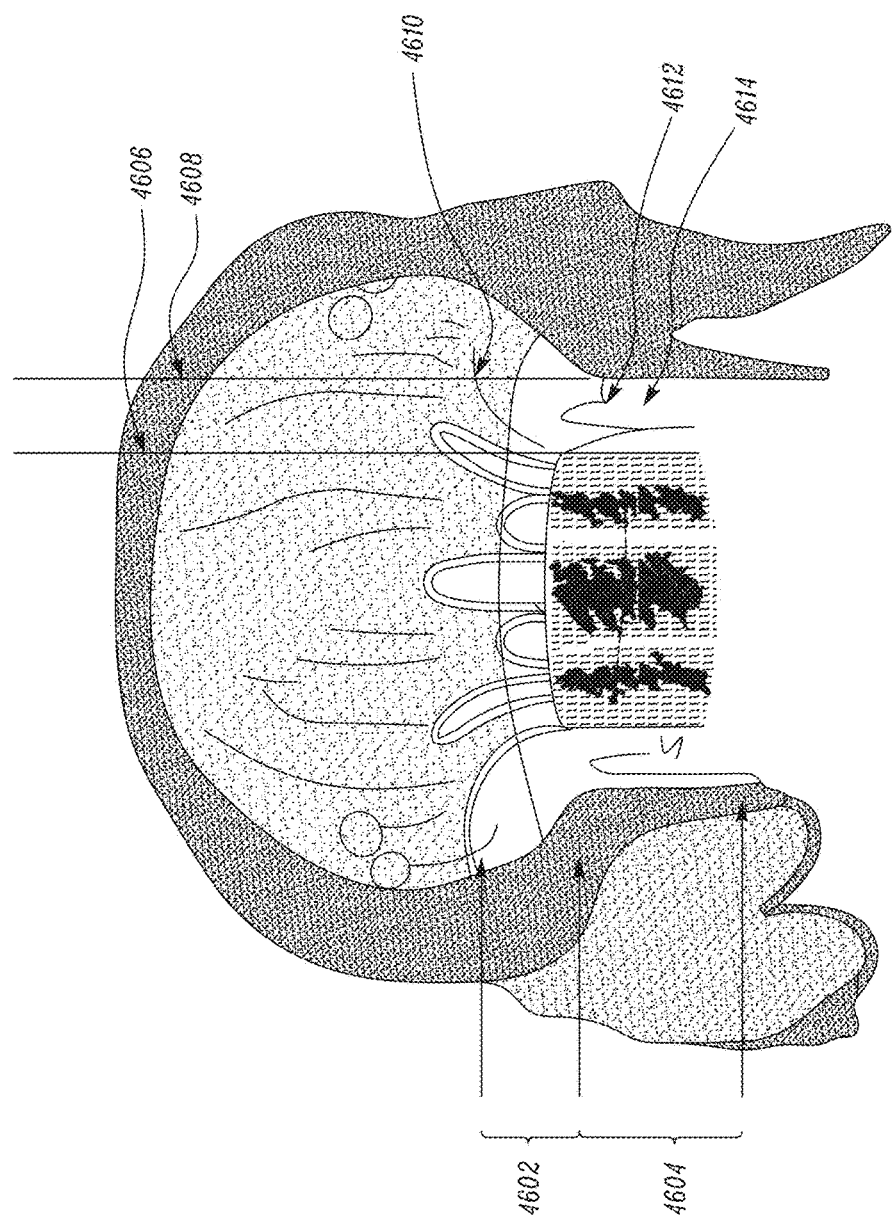
FIG. 41 illustrates an exemplary valve prosthesis formed of the exemplary loops of FIG. 26 used in replacing a mitral valve.

FIG. 41 illustrates an exemplary valve prosthesis formed of the exemplary loops of FIG. 26 used in replacing a mitral valve 4612 at a mitral annulus 4608. The prosthesis may form a new annulus 4606. The valve prosthesis is formed of the exemplary loops attached in a circular arrangement. Each of the primary loops may include a proximal portion 4602 (including, for example, one or more fixation or anchoring components 4610), a distal sub-annular portion 4614 (including, for example, one or more fixation or anchoring components), and a valve housing portion 4604.

Figure 42:
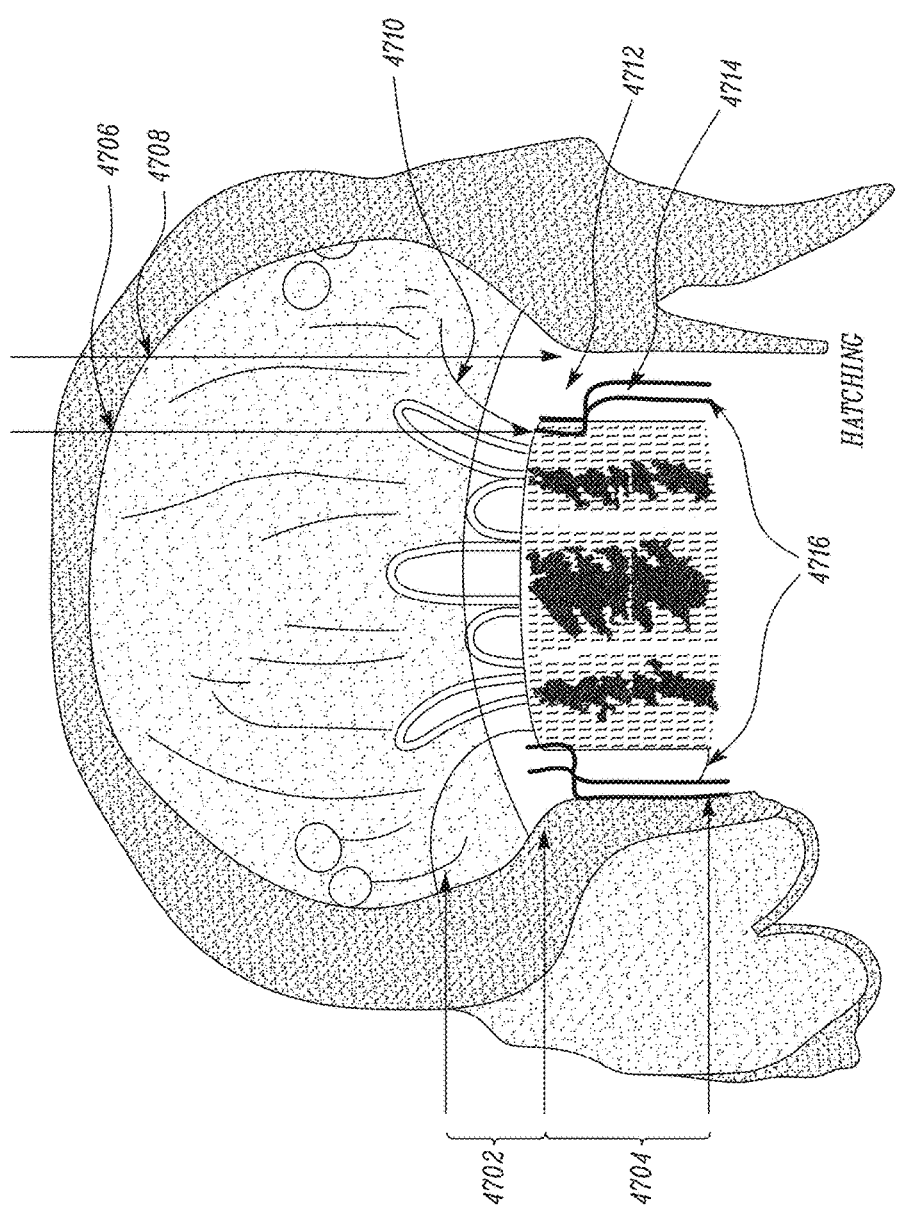
FIG. 42 illustrates an exemplary valve prosthesis formed of exemplary loops having a skirted mid and distal portion used in replacing a mitral valve.

FIG. 42 illustrates an exemplary valve prosthesis formed of exemplary loops having a skirted mid and distal portion used in replacing a mitral valve 4712 at a mitral annulus 4708. The prosthesis may form a new annulus 4706. The valve prosthesis is formed of exemplary loops attached in a circular arrangement. Each of the primary loops may include a proximal portion 4702 (including, for example, one or more fixation or anchoring components 4710), a distal sub-annular portion 4714 (including, for example, one or more fixation or anchoring components), and a valve housing portion 4704. Each loop may have a skirted configuration 4716 at the valve housing portion 4704.

In an exemplary embodiment, an exemplary valve prosthesis may be deployed by a catheter and may self-expandable when deployed at a heart valve annulus. In another exemplary embodiment, the valve prosthesis may be deployed by a catheter and may be expandable by a balloon when deployed at a heart valve annulus.

Figure 43:
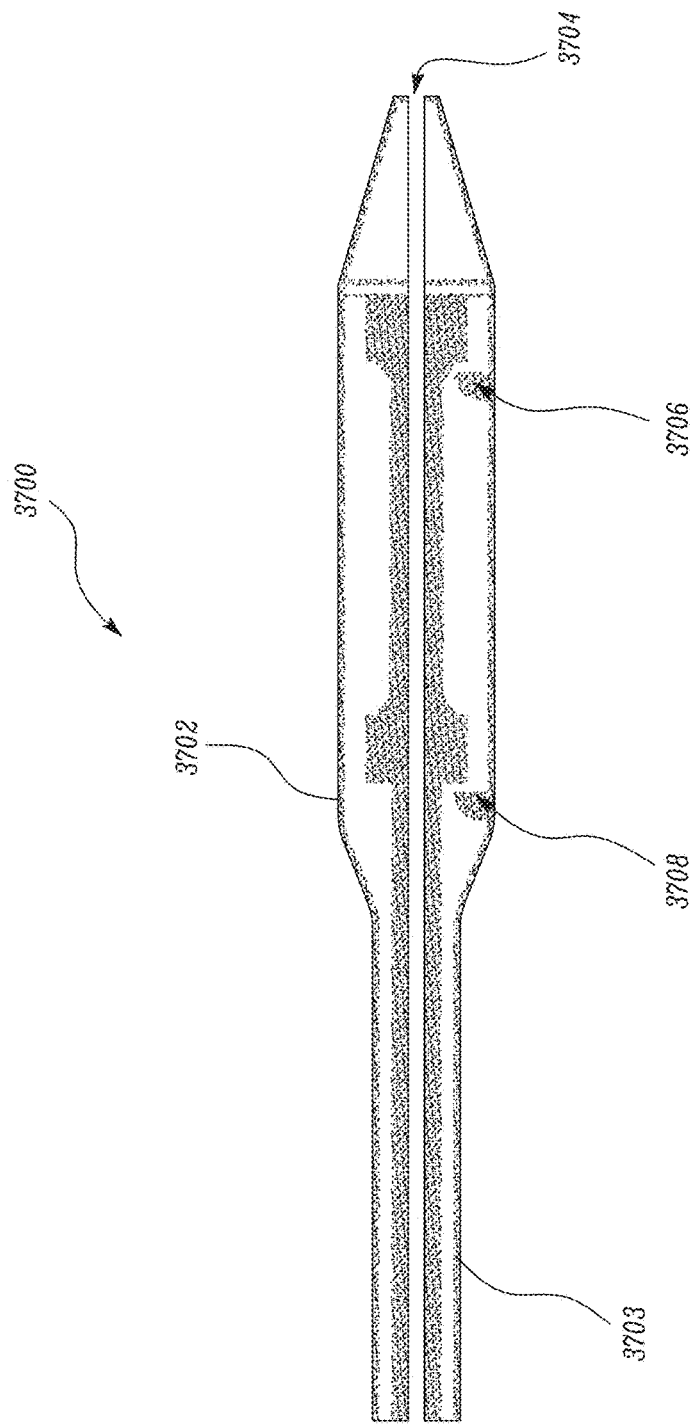
FIG. 43 illustrates an exemplary delivery device for delivering a valve prosthesis to the annulus of a heart valve.

FIG. 43 illustrates an exemplary delivery device 3700 for delivering a valve prosthesis to a heart valve annulus. The device 3700 includes a longitudinal body 3702 in which the valve prosthesis may be disposed. The valve prosthesis may be connected at a proximal end close to the operator to a projection mechanism 3703 that may be actuated to project the valve prosthesis out of the body through a lumen 3704 provided at the front end of the body. The projecting mechanism 3703 may selectively actuate and deploy the proximal primary loops, the proximal secondary loops and the sub-annular loops of the valve prosthesis. The device 3700 may include one or more mechanisms 3706 and 3708 for actuating the projecting mechanism 3703. The device 3700 may allow the valve prosthesis to be retrieved from the patient's body prior to its full deployment and release.

In exemplary embodiments, one or more radio-opaque markers may be placed on the delivery device to facilitate in positioning and deploying a valve prosthesis by the delivery device. The markers may also enhance physician feedback and a tactile feeling. Exemplary markers may include, but are not limited to, radial markers, individual markers, pad printed markers and/or woven monofilament markers.

Before, during and after delivery, imaging and annular mapping of the annulus of the heart valve and its surrounding cardiac anatomy is performed. Considerations of patient safety and the device size may drive the access point on the patient's body that is selected for delivering the valve prosthesis. In an exemplary method for delivering a mitral valve replacement, an exemplary delivery device is inserted over a guide wire into a prepositioned introducer sheath into the femoral vein, and eventually through the patent foramen ovale wall above the valve annulus. The device may be advanced to the left ventricle toward the bottom of its apex.

Before proceeding, imaging, e.g., fluoroscopic, may be performed to image the valve annulus, the surrounding anatomy and the device in relation to the annulus and the anatomy. The device may be radio-opaque and have markers. In another exemplary method, the delivery device may be inserted percutaneously or by off-pump thorocodomy by direct access to the apex, chest and jugular areas of the patient.

Figure 44:
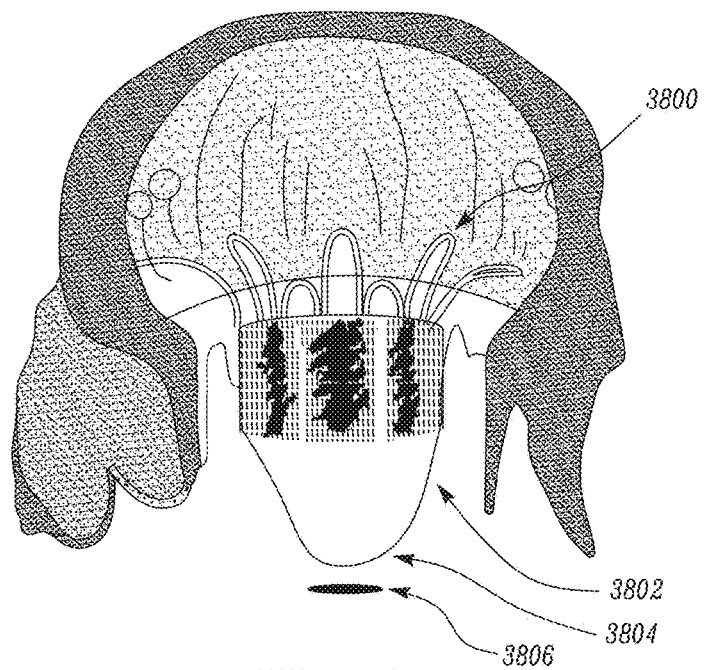
FIG. 44 illustrates an exemplary valve prosthesis that is anchored by one or more anchoring threads that connect to an anchoring mechanism at the bottom of the ventricular apex.

FIG. 44 illustrates an exemplary valve prosthesis 3800 that is anchored by one or more holding strings 3802 that connect to an anchoring mechanism 3804 at the bottom of the ventricular apex 3806. This configuration allows the valve prosthesis to be anchored to the bottom of the apex. If the prosthesis is deployed from the atrium (in an apical approach), the primary loops are first deployed and the sub-annular loops are subsequently deployed. Prior to the delivery device exiting the apex, the anchoring mechanism 3804 is put in place such that the valve prosthesis 3800 is connected to the anchoring mechanism 3804 through the strings 3802. If the prosthesis is deployed in a femoral approach, the anchoring mechanism 3804 is first put in place at the apex 3806, the sub-annular loops are deployed, and subsequently the primary loops are deployed.

In a minimally invasive method illustrated in FIGS. 47A-47D, an exemplary delivery device 4100 may have a left ventricular transapical access. As illustrated in FIG. 47A, an apical wire 4102 may be placed through the mitral valve 4104. As illustrated in FIG. 47B, the delivery device 4100 may be advanced over the wire 4102 through the mitral valve 4104 to the left atrium 4106. Before proceeding, imaging, e.g., fluoroscopic, may be performed to image the valve annulus at the mitral valve 4104, the surrounding anatomy and the device 4100 in relation to the annulus and the anatomy. The device 4100 may be radio-opaque and have markers. As illustrated in FIGS. 47C-47E, the proximal primary loops, the proximal secondary loops and the sub-annular loops of the valve prosthesis, respectively, may be deployed using one or more projection mechanisms in the delivery device.

Figure 45:
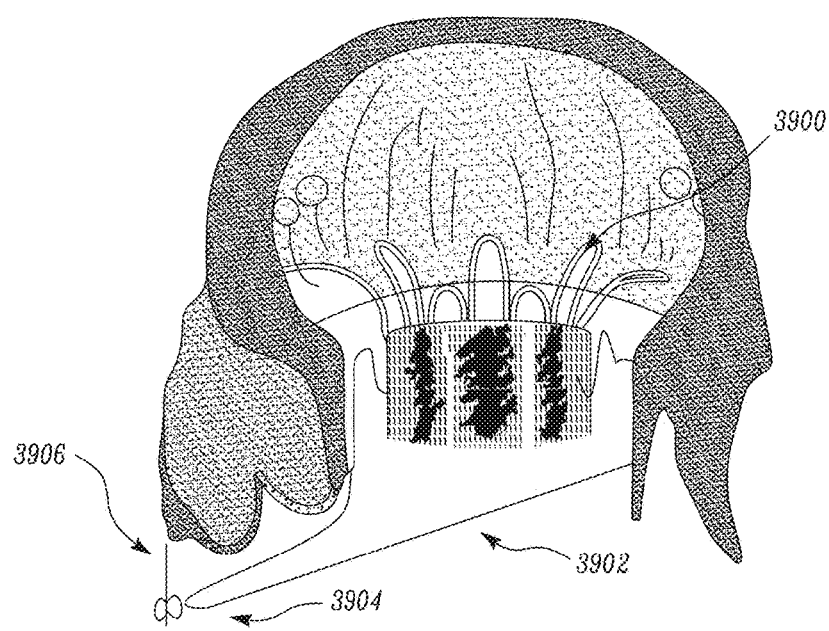
FIG. 45 illustrates an exemplary valve prosthesis that is anchored by one or more holding strings that connect to an anchoring mechanism at a ventricular septal wall.

FIG. 45 illustrates an exemplary valve prosthesis 3900 that is anchored by one or more holding strings 3902 that connect to an anchoring mechanism 3904 at a ventricular septal wall 3906.

Figure 46:
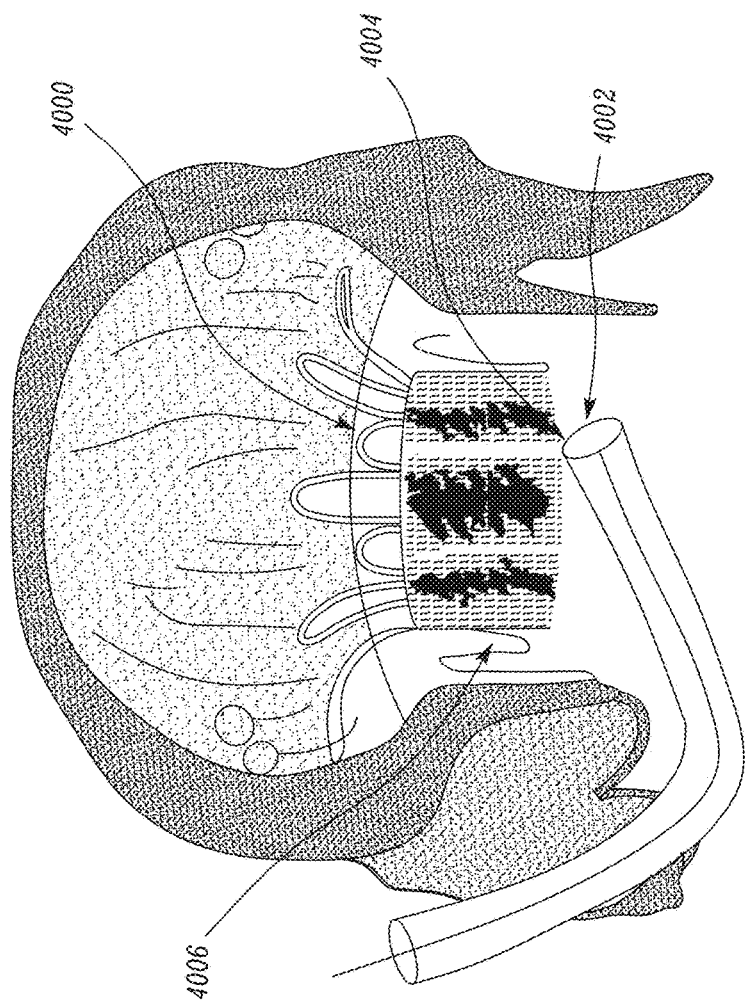
FIG. 46 illustrates an exemplary valve prosthesis that is anchored to the posterior region of a heart valve.

FIG. 46 illustrates an exemplary valve prosthesis 4000 that is delivered by a retrograde catheter system 4002 through the aorta. The valve prosthesis 4000 may be anchored to the ventricle using one or more anchors. The example of FIG. 46 shows two exemplary anchors 4004 and 4006 deployed at either end of the posterior region of the mitral valve to anchor the valve prosthesis 4000 in the annulus.

Further Delivery Systems and Prostheses

The prostheses illustrated above can be installed in place as disclosed above and additionally by applying clips and other fasteners to keep them in place.

In accordance with further aspects of the disclosure, systems and related methods are provided for installing prostheses such as those disclosed above by way of a guide rail system. Such systems can be used for repair of the mitral and tricuspid valves as set forth above, but have equal applicability in other applications. Such systems are particularly advantageous for use in other locations in the lumenal systems of the body for placement of prostheses and the like, as set forth in further detail below.

In accordance with the illustrative embodiments concerning placement of a prosthesis in the mitral and tricuspid valves, it is preferred to perform proper imaging and annular mapping of the mitral valve annulus and adjacent anatomies before, during and after the prosthesis placement procedure. The procedures described herein concerning coronary valves may be performed by way of a minimally invasive incision and suitable access port into the thoracic cavity, or may be performed percutaneously via femoral or jugular access. Before proceeding, all vital signs should be checked, then detailed ICE or 3D echo and fluoroscopic imaging of the valve annulus and surrounding anatomy and its relation to the delivery system components and prosthesis should be performed. The delivery system as well as the prosthesis is preferably provided with appropriate radiopaque markers to facilitate placement as described herein.

Figure 48:
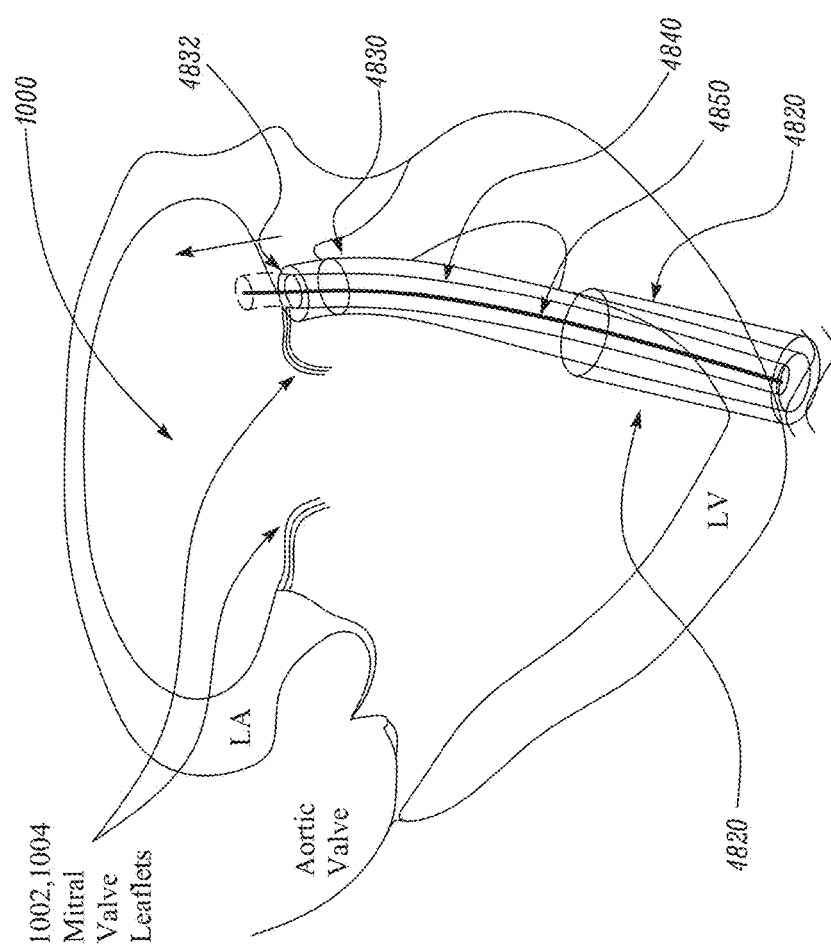
FIG. 48 illustrates a further exemplary delivery system for fixation above and below the mitral annulus.

For purposes of illustration, and not limitation, FIG. 48 illustrates a first step of an exemplary method for implanting a prosthesis in the mitral valve of a patient. The technique begins with introducing an introducer sheath 4820 of delivery system 4800 replacing a mitral valve 1000 having leaflets 1002, 1004. The introducer sheath 4820 is introduced into the left ventricle through the bottom of the ventricle and advanced and directed toward the ventricular side of the mitral annulus. It will be appreciated that the system can be modified for percutaneous delivery and that the present depicted method is only for purposes of illustration. Disposed within the delivery sheath 4820 is the main delivery system 4830 preferably having an articulable distal end as well as one or more radiopaque markers, such as marker bands. The main delivery system 4830 is then advanced and positioned behind the posterior mitral leaflet 1004 just under the annulus to the posterior mitral commissure. The mitral commissures are difficult to detect during surgery, and can be identified, for example, by using two anatomic landmarks: the axis of corresponding papillary muscles and the commissural chordate. Several millimeters of valvular tissue separates the free edge of commissures from the annulus. Distal end 4832 of delivery catheter 4830 is thus articulated to the posterior commissure. Next, an articulable lance, or poker 4850 is advanced through a distal end of a puncture catheter 4840, which is in turn housed within catheter 4830, into the posterior mitral commissure and into the left atrium to provide a path and guide rail for passing the puncture catheter 4840 through the posterior commissure and into the atrium. The puncture catheter 4840 may be of a peelable configuration, if desired. After further imaging to ensure that the procedure has been performed properly, the lance 4850 can be withdrawn back into the puncture catheter 4840, leaving catheter 4840 in path to act as a conduit for placement of further components of the system. The system 4800 can be used in like manner to provide passage for the puncture catheter 4840 through the anterior mitral commissure.

Once the puncture catheter is in place, it is possible to next place a guide rail in place that will anchor and bear against either the atrial or ventricular side of the mitral annulus at the anterior and posterior commissures. If it is desired to place an anchored guide rail wherein the anchor bears against the ventricular side of the valve annulus, a special guide wire/guide member as depicted in FIG. 49 can be used.

For purposes of illustration, and not limitation, guide member 4900 includes a first end 4910 having an anchor disposed thereon. Anchor 4910 is preferably a compliant foldable material, such as PTFE or PS fabric or ePTFE material (as described, for example, in U.S. Pat. No. 6,436,135 to Goldfarb, incorporated by reference herein in its entirety). Anchor 4910 preferably includes radiopaque material. As illustrated, anchor 4910 is attached to a tether 4920, such as of PTFE or other suitable material. Tether 4920 is preferably modified to include radiopaque material, and includes a first end 4922 attached to anchor 4910, and a second end 4924 attached to a first, distal end 4932 of a guide wire/guide member 4930. If desired, a plurality of locks or crimps 4940 can be provided on the tether 4920 to bear against the ventricular side of the annulus and hold anchor 4910 in place against the ventricular side of the annulus, described in further detail below. Guide member 4930 is preferably pre-attached to tether 4920, and preferably has a diameter of 0.35 inches or larger. A proximal docking station 4950 can be provided at a proximal end of the guide member for attachment to a further member that can be used to pull on the guide member 4930 to advance tether 4920 until anchor 4910 is urged against the mitral annulus. FIG. 50 illustrates a modified guide member 5030 that can be used for placement of an anchor 4910 against the atrial side of the mitral annulus, and FIG. 51 illustrates a tether 5120 having an anchor 5110, locks 5140 and docking station or connector 5150, wherein connector/docking station 5150 is adapted and configured to connect with distal docking station 5050a of guide 5030, whereas proximal docking station 5050b fulfills a function similar to docking station 4950. The use of the embodiments depicted in FIGS. 49-51 are described in further detail below.

FIGS. 52A, 53A, 54A, 55A and 56A illustrate a first exemplary method and system for disposing a pair of guide rails in the mitral annulus, wherein anchors are disposed on the underside (ventricular side) of the annulus of the mitral valve by way of the left ventricle using guide member 4900.

Figure 52A:
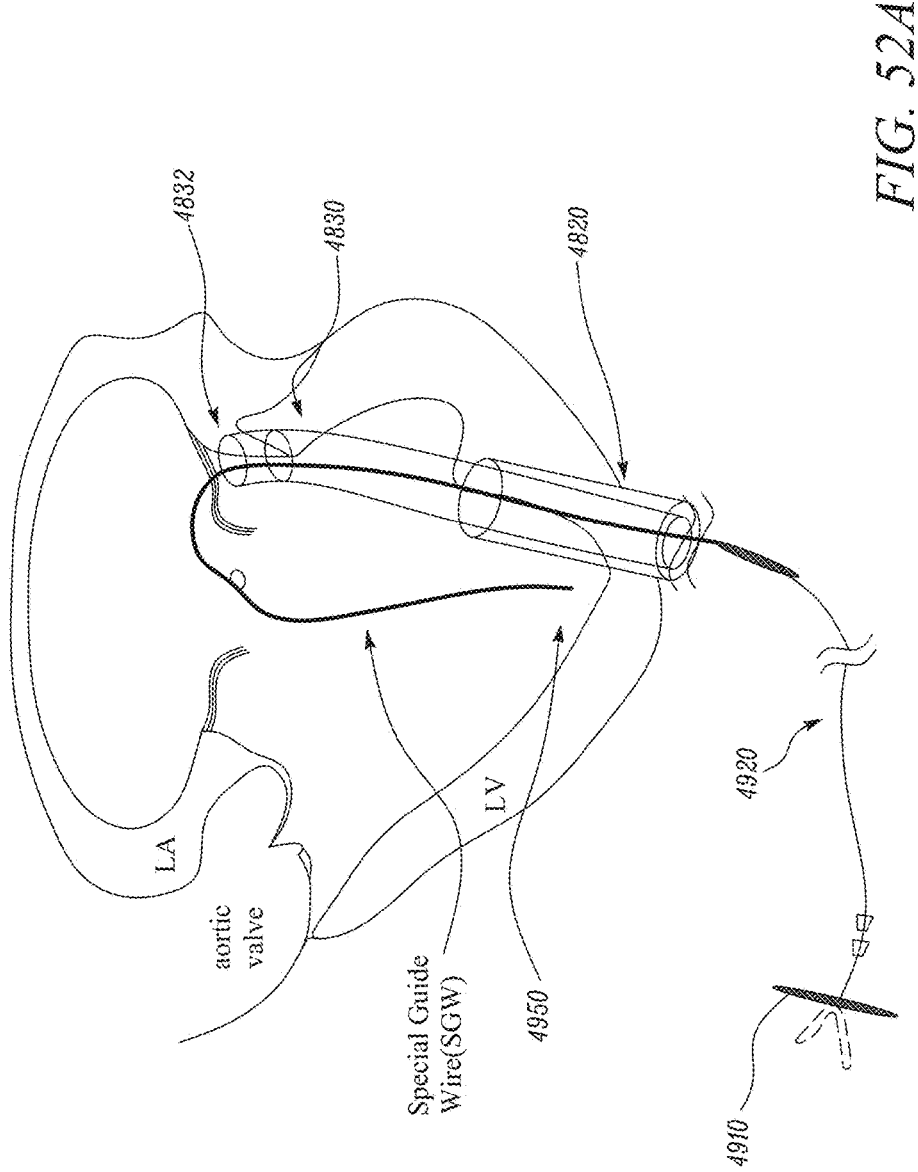
FIGS. 52A, 53A, 54A, 55A and 56A illustrate a first exemplary method and system for disposing a pair of guide rails in the mitral annulus, wherein anchors are disposed on the underside of the annulus of the mitral valve by way of the left ventricle.
Figure 53A:
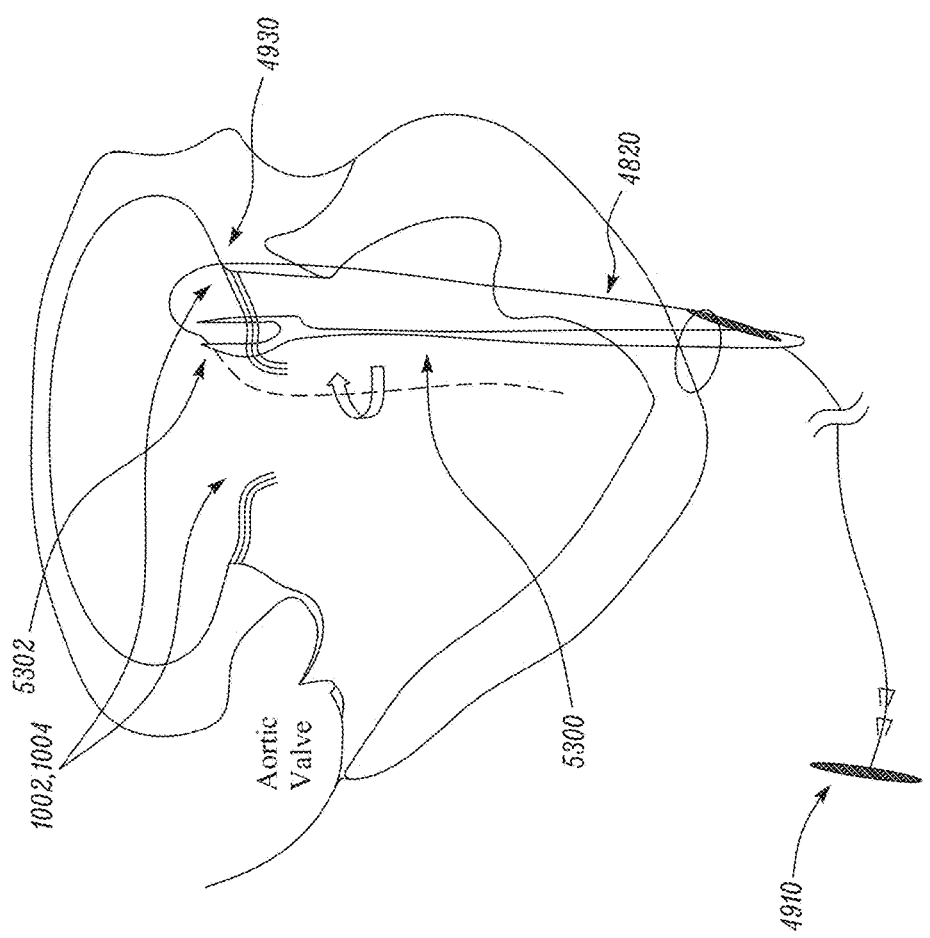
Figure 54A:
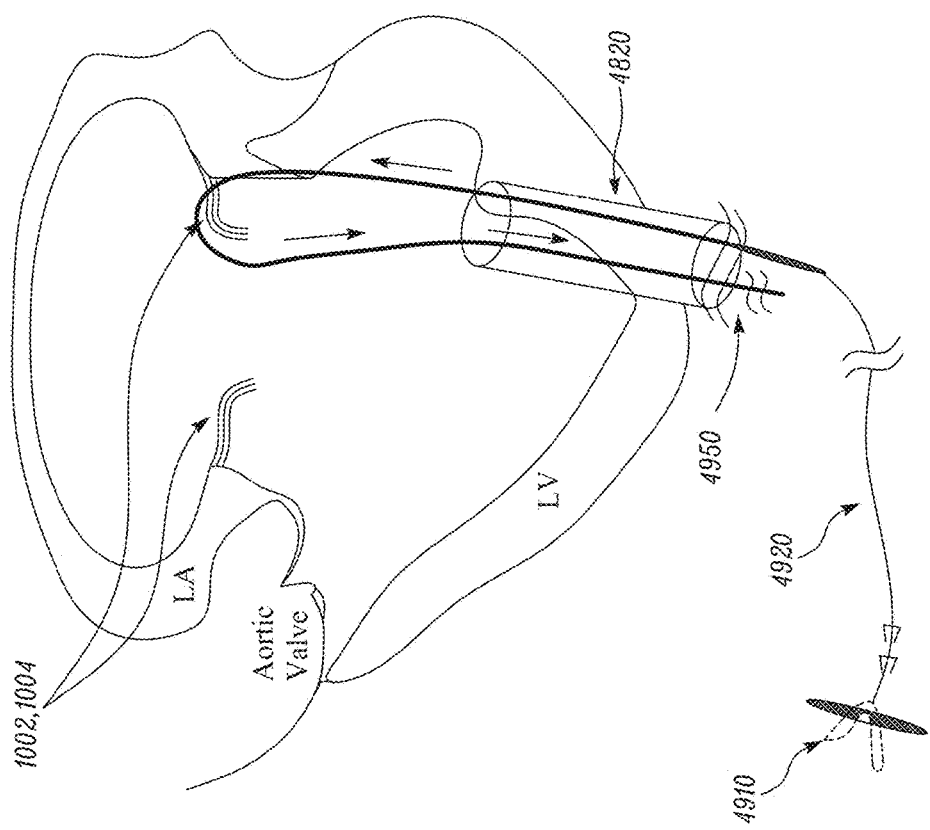
Figure 55B:
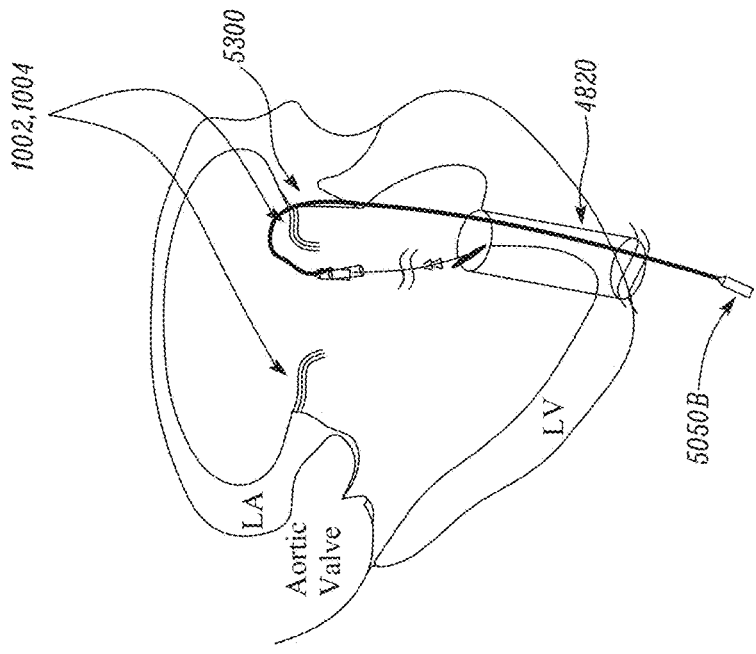
Figure 55A:
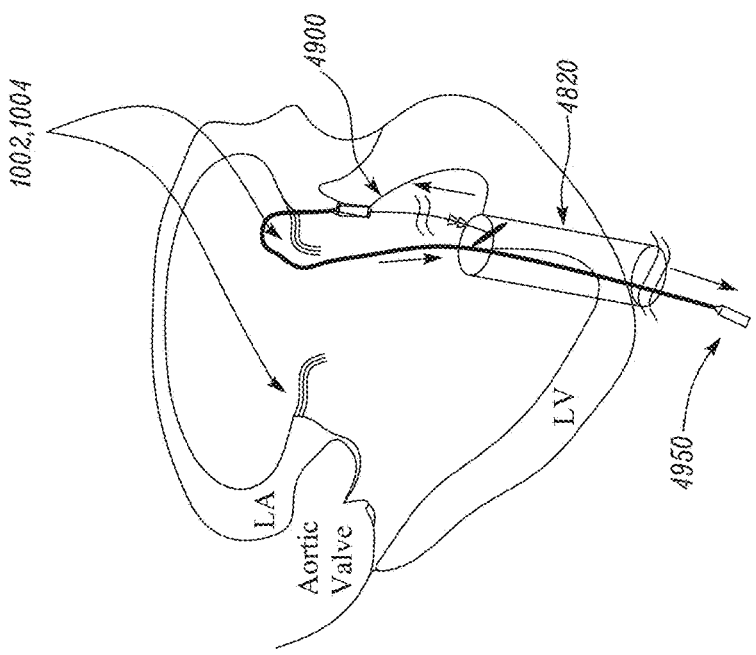
Figure 56B:
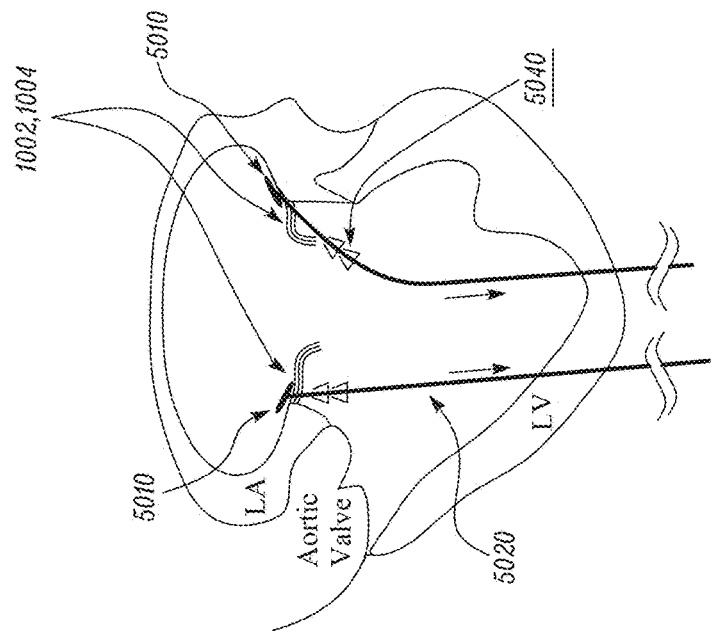
Figure 56A:
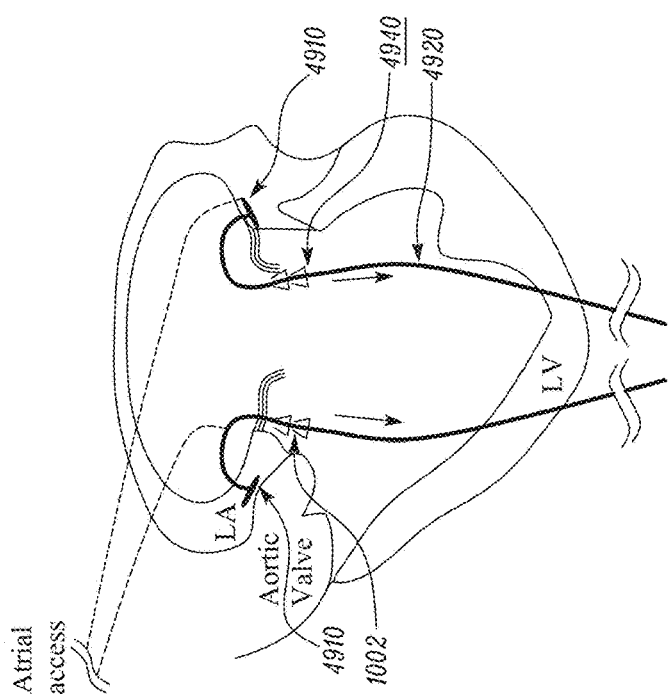

As depicted in FIG. 52A, the puncture catheter 4840 is withdrawn back into the delivery system 4800, and the proximal end 4950 of the special guide wire of the guide member 4900 is advanced through the delivery system, through the incision made by the puncture catheter 4840, and steered toward and through the mitral valve 1000 into the left ventricle. As depicted in FIG. 53A, a forceps, grasper or other device 5300, preferably with a radiopaque marker proximate its distal end 5302, is advanced through the delivery system 4800 and into the left ventricle to capture the end 4950 of the guide 4900. As illustrated in FIG. 54A, the proximal end 4950 of guide 4900 is withdrawn into the introducer sheath 4820 of delivery device 4800. Guidewire section 4930 of guide 4900 is then drawn fully through the commissure of the annulus of the mitral valve. As depicted in FIG. 55A, as the guidewire section 4930 exits the introducer sheath 4820, the tether 4920 is withdrawn from the sheath 4820, and passes through the annulus until the anchor 4910 is urged against the ventricular side of the mitral annulus. The process can then be repeated at the location of the anterior commissure, as depicted in FIG. 56A. At this point, locks/crimps 4940 can be advanced to the atrial side of the annulus and secured in place, resulting in the tethers 4920 being directed through the mitral valve and out of the heart to act as placement guides for a prosthesis.

FIGS. 52B, 53B, 54B, 55B and 56B illustrate a second exemplary method and system for disposing a pair of guide rails in the mitral annulus, wherein anchors are disposed on the upper side (atrial side) of the annulus of the mitral valve by way of the left ventricle using guide member 5000 that includes the combination of guide 5030 and tether 5120.

Figure 52B:
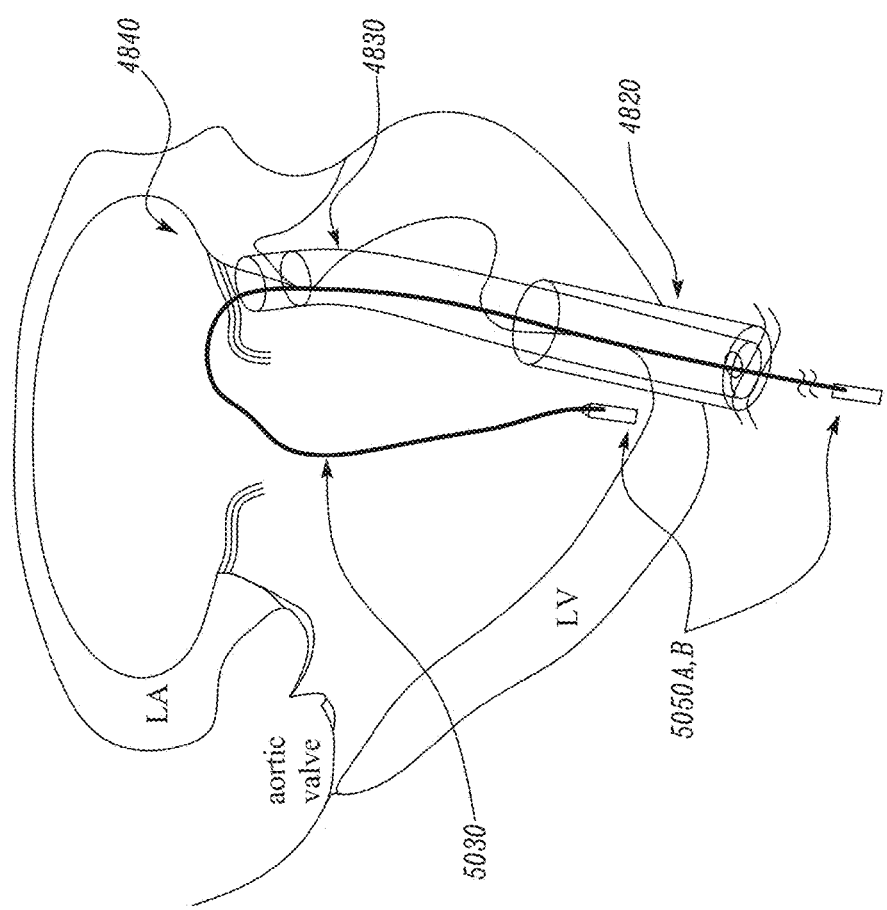
Figure 54B:
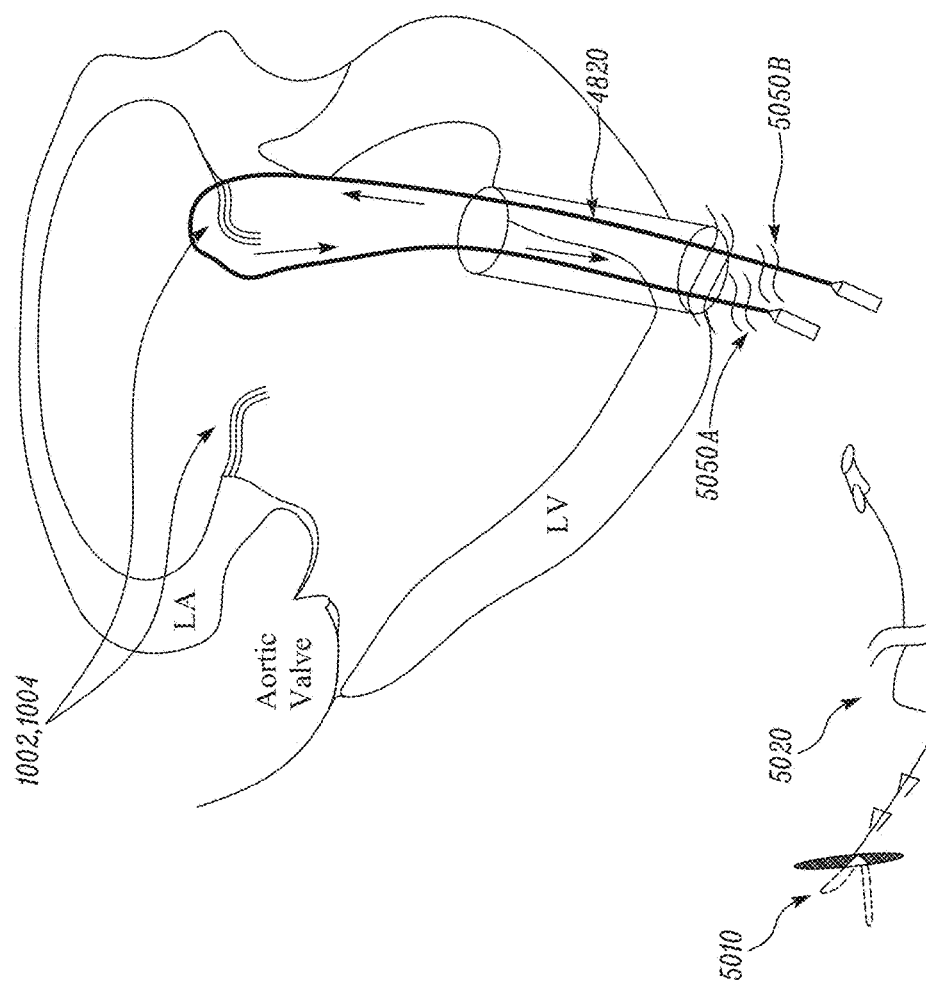

As depicted in FIG. 52B, the puncture catheter 4840 is withdrawn back into the delivery system 4800, and the proximal end 5050a of the special guide wire of the guide member 5000 is advanced through the delivery system, through the incision made by the puncture catheter 4840, and steered toward and through the mitral valve 1000 into the left ventricle. As depicted in FIG. 53B, a forceps, grasper or other device 5300, preferably with a radiopaque marker proximate its distal end 5302, is advanced through the delivery system 4800 and into the left ventricle to capture the end 5050a of the guide 5030. As illustrated in FIG. 54B, the proximal end 5050a of guide 4900 is withdrawn into the introducer sheath 4820 of delivery device 4800. Guidewire section 5030 of guide 5000 is then drawn fully through the commissure of the annulus of the mitral valve. As depicted in FIG. 55B, as the guidewire section 5030 exits the introducer sheath 4820, the tether 5020 is withdrawn from the sheath 4820, and passes through the annulus until the anchor 5010 is urged against the atrial side of the mitral annulus. The process can then be repeated at the location of the anterior commissure, as depicted in FIG. 56B. At this point, locks/crimps 5040 can be advanced to the ventricular side of the annulus and secured in place, resulting in the tethers 5020 being directed through the mitral valve and out of the heart to act as placement guides for a prosthesis.

A variety of devices can be used for locks 4940, 5040. For example, crimpable clips can be used, as well as buckles including a plate with two or more holes therethrough wherein the tether 4920, 5020 is routed through a first hole in the plate from a first side of the plate to the second side of the plate, and then through a second hole from the second side of the plate to the first side of the plate. The tether can then be held stationary with respect to the plate/clip by frictional forces and/or by folding the plate onto itself with forceps to crimp it. Moreover, if desired, the portion of tether 4920, 5020 proximate anchor 4910, 5010 can be provided with ratcheting teeth that engage complementary teeth or a slit in the locks 4940, 5040 such that the ratchet engagement maintains the position of the lock 4940, 5040. It will be appreciated that a variety of other locks can be used, and that these examples are merely illustrative.

Portions of delivery system 4800 (e.g., 4820, 4830, 4840) as well as the prosthesis delivery systems disclosed herein may be made in a variety of ways and from a variety of materials, such as metal, plastic and composite materials. Metal tubes such as stainless steel hypotubes can be used for one or more portions of delivery system 4800 for enhanced pushability alone or in combination with other suitable materials. If metal tubular components are used to make portions of system 4800, they are preferably coated with a lubricious material such as PTFE, other hydrophobic materials or hydrophilic materials. Multilayered polymeric tubes can also be used to form portions of system 4800 that can be formed by coextrusion, dipping processes, or by shrinking tubing layers over one another over a mandrel. Moreover, polymeric tubular members can also be formed by charging a mandrel with static electricity, applying plastic in powder or granular form to the mandrel to form a layer of plastic over the mandrel, and by heating the mandrel to cause the particles to fuse.

If desired, one or more of components 4820, 4830, 4840 as well as the prosthesis delivery systems disclosed herein can include a multi-layered coextrusion, such as those described in U.S. Pat. No. 6,464,683 to Samuelson or U.S. Pat. No. 5,538,510 to Fontirroche. Each of the aforementioned patents is incorporated by reference herein in its entirety. Any surface of various components of the catheters described herein or portions thereof can be provided with one or more suitable lubricious coatings to facilitate procedures by reduction of frictional forces. Such coatings can include, for example, hydrophobic materials such as PolyTetraFluoroEthylene ("PTFE") or silicone oil, or hydrophilic coatings such as Polyvinyl Pyrrolidone ("PVP").

Other coatings are also possible, including, echogenic materials, radiopaque materials and hydrogels, for example. Multilayered polymeric tubes can also be used that include metallic or nonmetallic braiding within or between layers of the tube. A carbon tube can also be used, as well as fiber-reinforced resin materials.

In accordance with further aspects, any portion of delivery system 4800 (particularly portions 4820, 4830, 4840) as well as the prosthesis delivery systems disclosed herein can be provided with a decreasing stiffness along its length from a proximal portion to a distal portion. As will be further appreciated by those of skill in the art, introducer sheath 4820 or delivery catheter 4830 can also include a multiple-lumen extrusion including two, three, four, or more lumens along part of or substantially the entire length thereof. Moreover, stiffening members such as stiffening wires can be used at various locations along portions of components 4820, 4830, 4840 to provide stiffness transitions between relatively stiffer regions and less stiff regions, as well as proximate regions of stress concentration. In accordance with one embodiment, a guidewire lumen 118 is provided along substantially the entire length of elongate body 110 as with typical over the wire ("OTW") catheters. In accordance with another embodiment, a guidewire lumen (not shown) is provided along a distal length of components 4820, 4830 and/or 4840 to permit use of such components as rapid exchange "RX") catheters. This can be useful both when accessing the heart via the thoracic cavity, as well as when accessing the heart via the aortic arch.

The docking station(s) (e.g., 4950, 5050a, 5050b) may include various types of connectors, such as snap fit, threaded and the like. Suitable connectors can be found, for example, in U.S. Pat. Nos. 4,827,941, 5,617,875, 4,917,103, 4,922,923, 5,031,636 and U.S. Reissue Pat. No. 34,466. Each of these patents is incorporated by reference herein in its entirety. An actuator (not shown) may be used to produce relative movement between the various components of the delivery system 4800, as well as other delivery systems described above and below for delivering and deploying a prosthesis. For example, a relatively simple push-pull actuator may be provided. Moreover, it is also possible to use other actuators as are known in the art, such as threaded rotating actuators as described in U.S. Pat. No. 6,488,694 to Lau and U.S. Pat. No. 5,906,619 to Olson, each of which is incorporated by reference herein in its entirety.

It will be further appreciated that the tethers need not be installed at the commissures of the mitral annulus, but instead or in addition may be installed at any portion of the mitral annulus. Thus, while two tethers are depicted, any desired number, (e.g., three, four, five, etc.) may be installed. It will be further appreciated that a like procedure can be performed at the tricuspid valve or other locations within the luminal systems of a patient, discussed in further detail below.

In further accordance with the disclosure, once one or more tethers, or rails, are in place, a prosthesis can be advanced to a location proximate the tether anchor, and secured in place.

For purposes of illustration, and not limitation, as embodied herein and as depicted in FIGS. 57-63, methods and systems are provided for installation of various prostheses proximate the mitral valve of a patient. While only procedures with respect to rails anchored on the ventricular side of the mitral annulus for purposes of brevity, it will be appreciated that such procedures are equally applicable With reference to FIG. 57A, a prosthesis 5700 is provided having a first bottom circumferential end 5712, a second top circumferential end 5714 and defining a general cylindrical body 5730 between the ends. The body may be straight or tapered, and may be flared as desired. Loops 5702 are provided defining the structure of the prosthesis can serve as a conduit for passage of the tethers or rails 4920, 5020. Preferably, channels or conduits 5710 are provided on prosthesis for specifically receiving the tethers or rails 4920, 5020. While a full prosthesis that occupies the full mitral orifice is illustrated in FIGS. 57A-57B, it is similarly possible to provide a prosthesis 5780 that occupies only a portion of the valve upon installation as depicted in FIG. 57(C). As depicted, prosthesis 5780 has a bottom arcuate edge 5782 upon deployment, an upper arcuate edge 5784 upon deployment, and defines a generally arcuate body 5785 upon deployment depicted as including a series of structural loops 5786 connected to a curved planar membrane 5785, and depicted as including a plurality of conduits 5710 for receiving guide rails. Thus, in the case of a mitral valve, one or two half-valves can be installed that sits on one of the leaflets, while in the case of tricuspid valve procedures, a single full prosthesis can be installed, or one or more partial prostheses that occupy one or two thirds of the valve or the entire valve. Thus, in the case of the tricuspid valve, a single implant can be used to replace the entire valve, one third of the valve or two thirds of the valve. Similarly, two prostheses can be used to replace the entire valve, wherein one prosthesis is used to replace one of the leaflets, and the remaining two leaflets are replaced by way of a second prosthesis. In any event, the prosthesis can be made of self expanding material (e.g., NiTi alloys), conventional alloys (e.g., stainless steels) or biodegradable materials. One or more radiopaque markers is preferably provided along the length and/or disposed about the circumference of the valve to facilitate axial and rotational alignment of the prosthesis. It will be further appreciated that a full or partial prosthesis can be provided in accordance with any embodiment described herein that contains no valve at all but that instead provides a fully or partial open channel (illustrated, for example, in FIG. 22) to simply provide patency or to serve as a platform for attaching a second implantable device. Thus, the prosthesis 5700 can be used to provide a platform for installing any desired replacement valve, whether the valve is synthetic and/or made from living tissue. It will be further appreciated that the prosthesis 5700 can be provided with a valve (and/or other portions, as desired) made from living tissue. As further illustrated, two rails are used for placement of the prostheses, but it will be appreciated that any number of rails can be used at any desired location in the valve annulus, or elsewhere in the anatomy, to deliver and install the prosthesis.

Figure 58A:
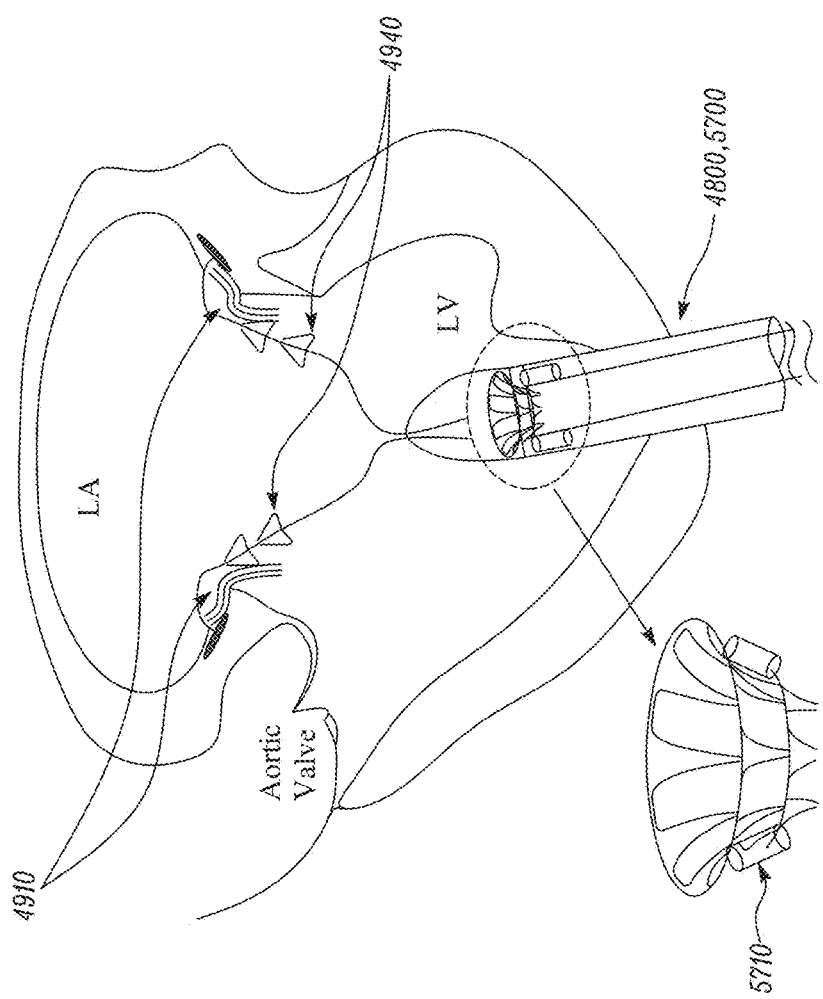
Figure 59A:
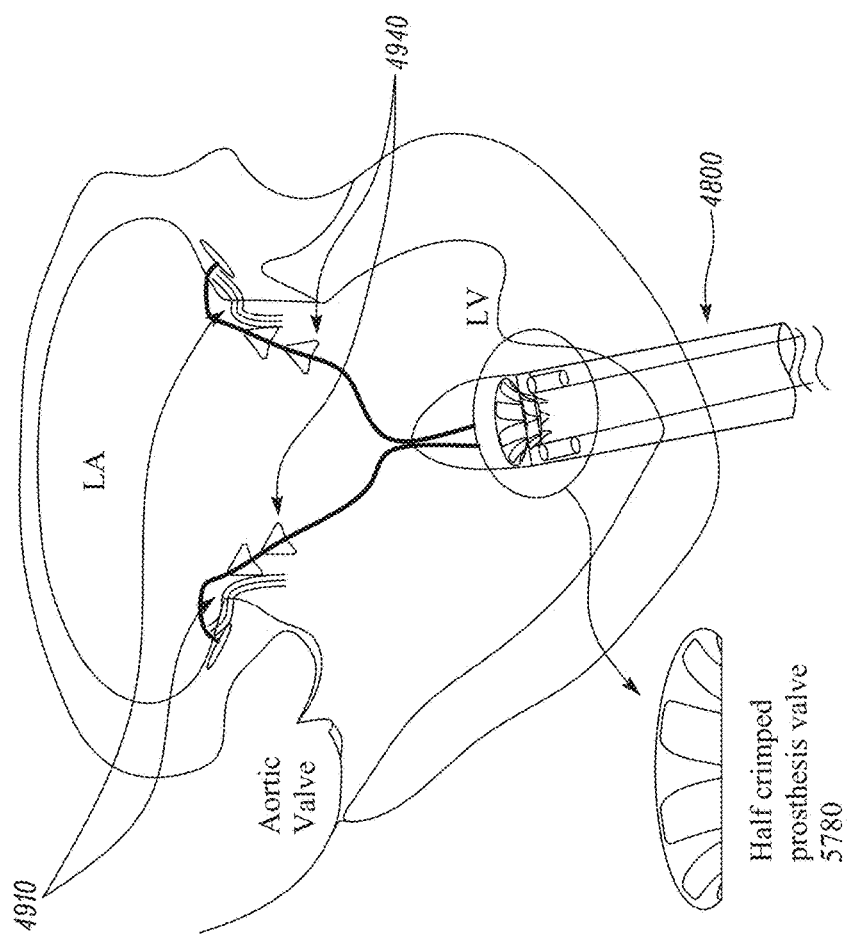
FIGS. 59A-59B and 60B illustrate an exemplary placement of a half prosthesis in the mitral orifice by way of rails anchored from beneath the mitral annulus.
Figure 59B:
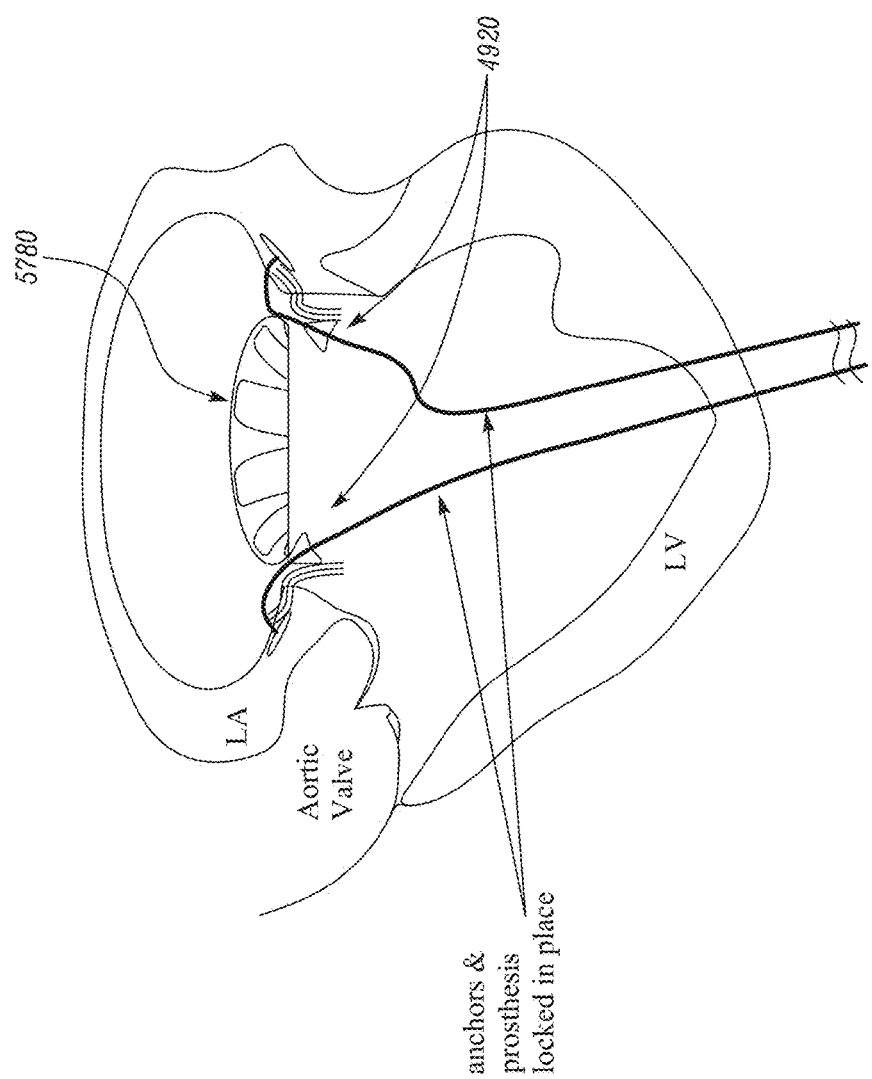
Figure 60B:
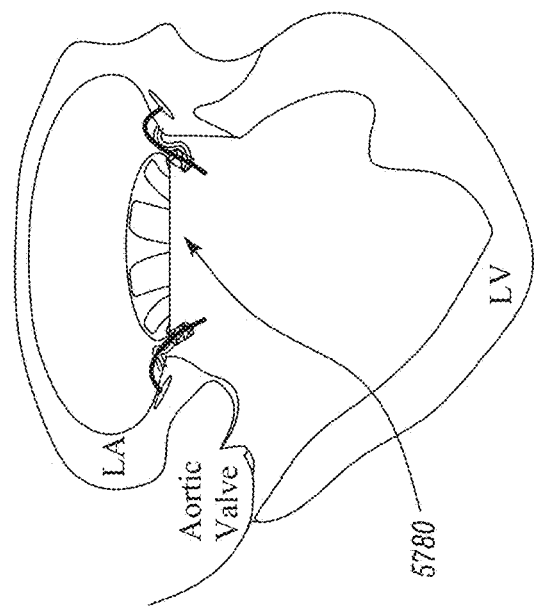
Figure 60A:
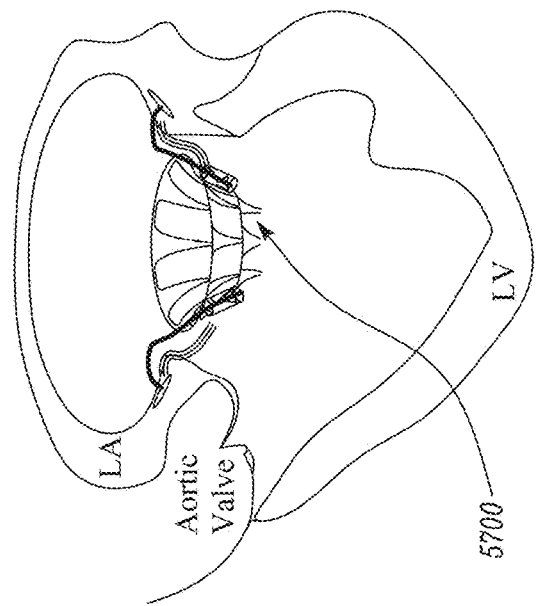

In use, as depicted in FIG. 58A, prosthesis 5700 is disposed over rails/tethers 4920 and advanced toward the mitral orifice along the rails/tethers 4920 as depicted in FIG. 58B. Once initially installed, the prosthesis can be held in place using a variety of techniques as described with respect to anchoring tethers 4920, 5020. FIGS. 59A-59B illustrate a similar installation of half prosthesis 5780. After initial installation, the patient's heart's performance can be monitored and the positioning of the prosthesis can be fine tuned. Once the prosthesis is in its final position, the prosthesis can be locked in place permanently. Clips or locks can be used, moreover, the conduits 5710 can be deformable and can be crushed over rails/tethers 4920, 5020 to lock the prosthesis 5700 in place and tethers removed in FIG. 60A for a full prosthesis and 60B for a partial prosthesis.

In accordance with further embodiments, the disclosure provides a prostheses having one or more tethers attached thereto for installing the prosthesis and techniques for installing the same. In particular, methods are provided including anchoring a rail at a target anatomical location within a patient's lumenal system, advancing a prosthesis having a tether over the rail, and attaching the rail to the tether to secure the prosthesis in place.

Figure 61A:
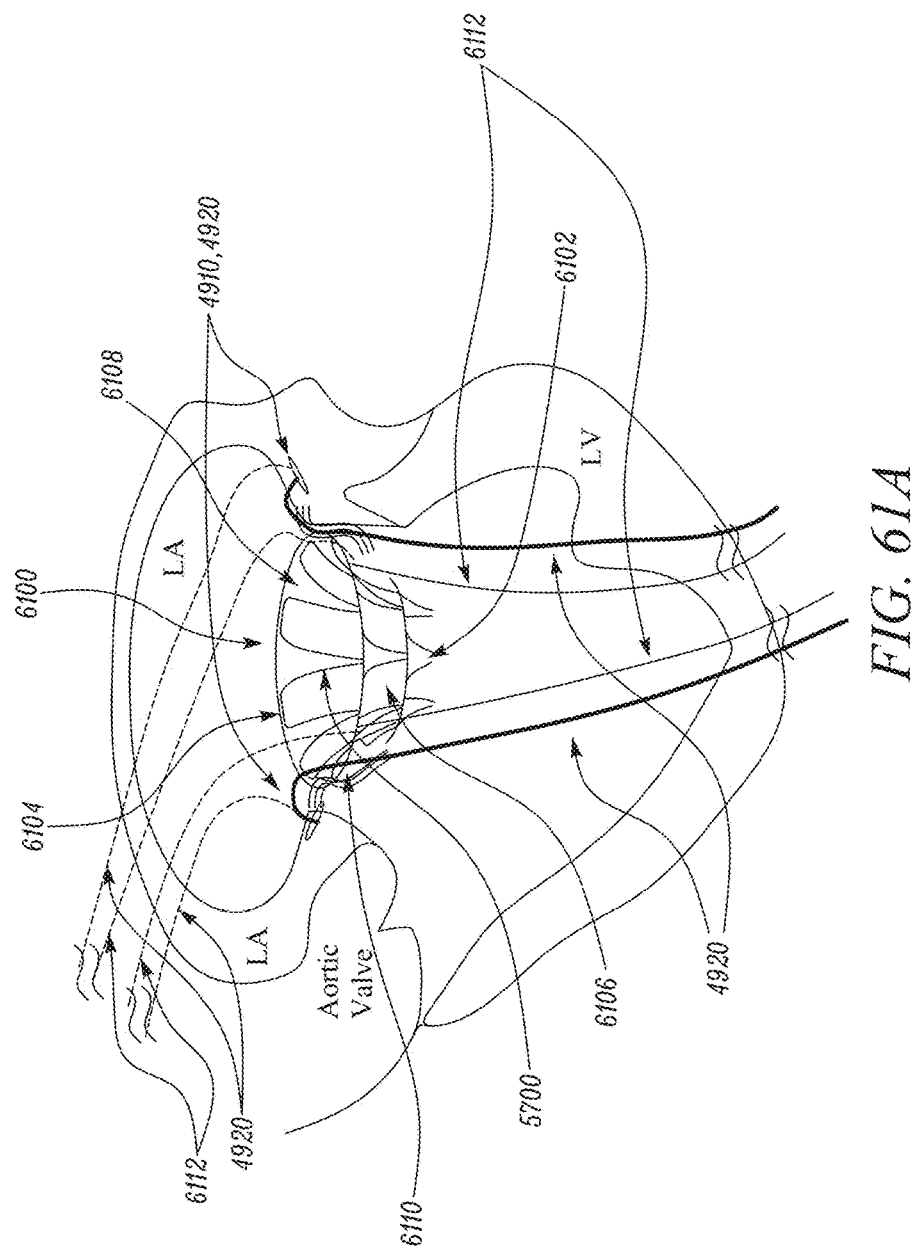

For purposes of illustration, and not limitation, as embodied herein and as depicted in FIG. 61(A), a full mitral valve prosthesis 6100 is provided having a lower circumferential edge 6102 and an upper circumferential edge 6104 defining a generally cylindrical body therebetween defined by a plurality of loops 6108 connected to a membrane 6106. The body may be tapered along its length and/or have flared ends, as desired. The prosthesis 6100 further includes one or more tethers 6112. Prosthesis is installed in the same manner as prosthesis 5700 insofar as it is advanced along rails 4920 via conduits 6110 to its final location. FIG. 61A further depicts the access direction in dotted lines in the case of atrial percutaneous delivery.

Similarly, FIG. 61B depicts a partial (e.g., half) prosthesis 6180 installation in a mitral annulus, wherein the prosthesis includes a bottom arcuate edge 6182 upon deployment, an upper arcuate edge 6184 upon deployment, and defines a generally arcuate body upon deployment depicted as including a series of structural loops 6186 connected to a curved planar membrane 6185, and depicted as including a plurality of conduits 6110 for receiving guide rails as well as one or more tethers 6172. FIG. 61B further depicts the access direction in dotted lines in the case of atrial percutaneous delivery.

In either the case of a full or partial prosthesis, the tethers 4920, 6112; 4920, 6172 are attached to each other to secure the respective prosthesis in place. The tethers can be knotted together via using a knot pusher to push one or more knots along the rails/tethers to a location proximate the prosthesis. Additionally or alternatively, the rails/tethers can be secured to each other by way of clips, crimps, buckles and the like.

Figure 63E:
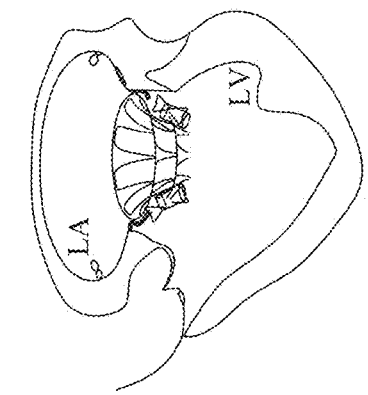

As illustrated in FIGS. 63A, 63B, 63C, 63D, 63E, and 64A-64B, the rails can be anchored within the mitral valve leaflets 1002, 1004. As illustrated in FIG. 63A, mitral leaflets 1002, 1004 are captured by a delivery system 6300. The leaflets are then pierced and an anchor (e.g., 4910) and rail (e.g., 4920) are advanced through the leaflet as depicted in FIG. 63B.

It will be appreciated that a variety of mechanisms can be used to capture the leaflets. If desired, a suturing device can be used to pass a tether/suture through each leaflet. Suitable examples of such suturing devices can be found, for example, in U.S. Pat. Nos. 7,862,572 and 7,993,354. These patents are incorporated by reference herein in their entireties.

Figure 63D:
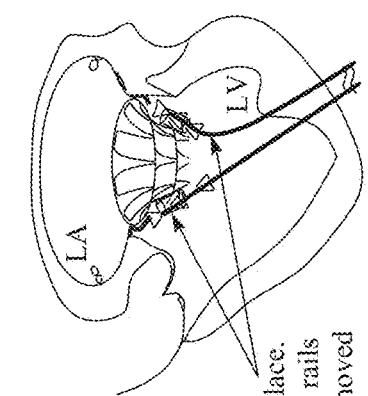
Figure 63C:
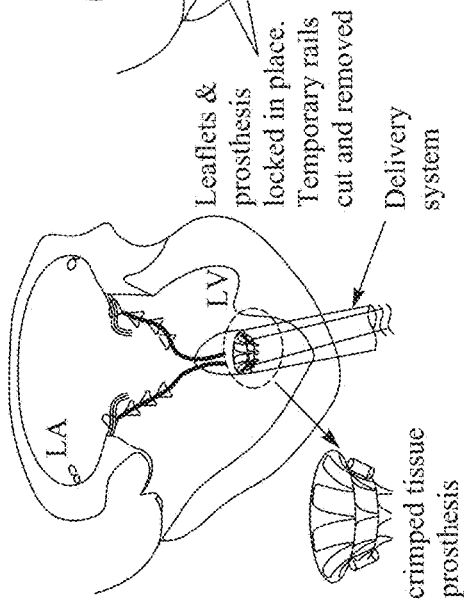

A crimped prosthesis is then advanced over the tethers as illustrated in FIG. 63C, and locked in place as illustrated in FIG. 63D. In FIG. 63E, the tissue prosthesis valve is shown in place, and locked. After checking all the vital signs, the reaming of temporary rails are removed and the procedure is then complete. Once adequate performance of the prosthesis is confirmed, the tethers are cut and installation is complete. As with earlier embodiments a prosthesis with integral tethers can also be used to anchor the tethers to the tethers that are attached to the leaflets as depicted in FIGS. 64A-64B. In FIG. 64A, shows a leaflets dual active fixation apical approach wherein the first of two active fixation rails occurs and the leaflets are attached to the deployed prosthesis. In the $2^{nd}$ fixation, the active fixation rails are attached to a second place. Finally, as shown in FIG. 64A, the two ends of the rails are knotted and advanced to lock the prosthesis in place. In FIG. 64B, the leaflets and annulus dual active fixation and final knotting and locking is shown.

Figure 65:
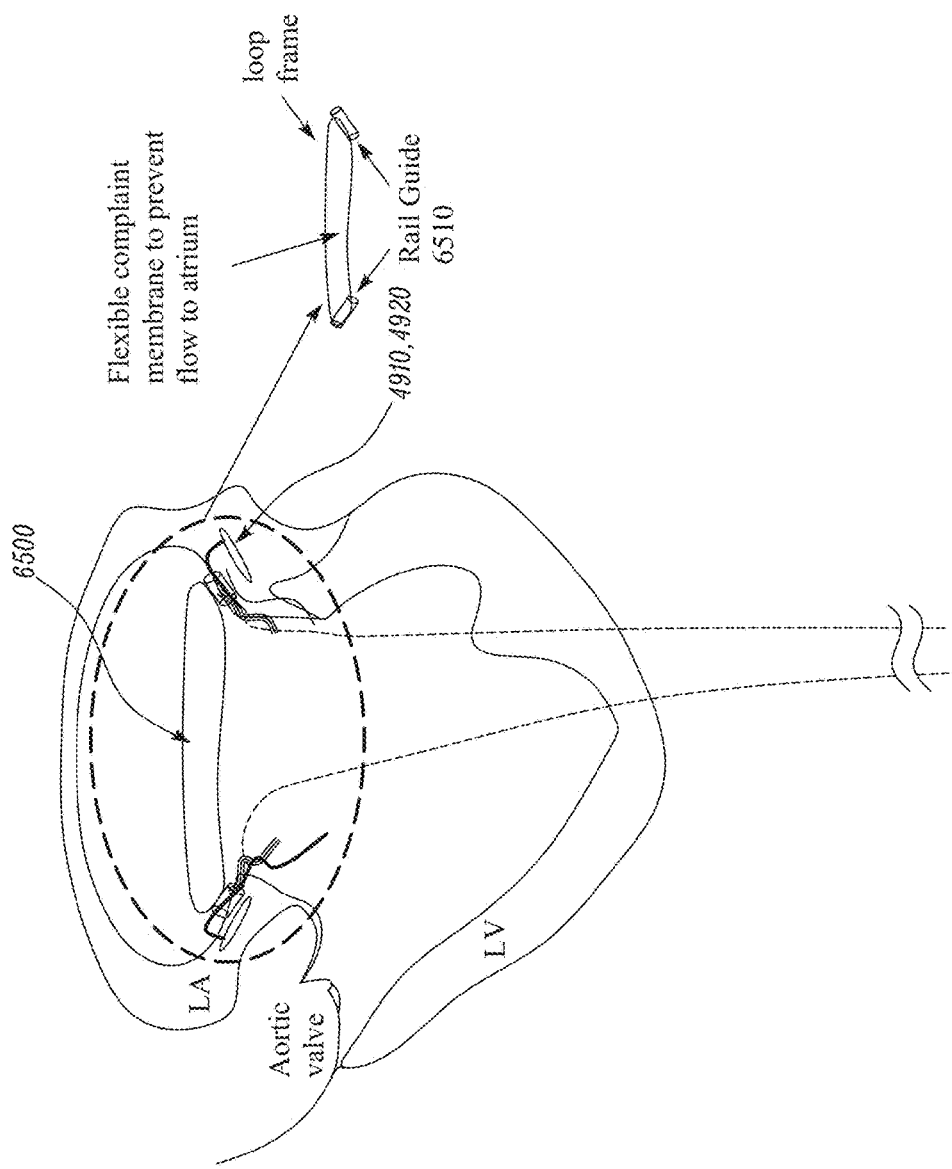
FIG. 65 illustrates an exemplary method and system for treatment of the mitral valve by, inter alia, securing an implant across the mitral valve opening to prevent regurgitation.

In accordance with a further embodiment, and as depicted in FIG. 65, a prosthesis 6500 can be installed above the mitral opening to help control regurgitation. The prosthesis preferably includes a flexible generally planar body housed, for example, in a structural loop that can optionally have conduits 6510 for receiving rails, and can be attached proximate the commissures or elsewhere about the mitral annulus. The prosthesis can be advanced along the rails as discussed herein to facilitate alignment and installation. The rails can be placed in any manner as described herein, including apical or retrograde placement. Preferably, the planar body is made from fabric and/or living tissue that absorbs the force of blood rushing past a defective native mitral valve arrangement to reduce or prevent regurgitation. As such, the prosthesis 6500 sits on the atrial side of the mitral valve, and can fill with and block the flow of blood from the ventricle into the atrium. As such, the size of the prosthesis 6500 should be selected to adequately cover any gap between the native leaflets. Preferably, prosthesis 6500 is installed while the heart is beating and without modifying the native leaflets. It is believed that prosthesis 6500 can be useful in treating various mitral abnormalities, including an enlarged heart, and/or calcification of the existing leaflets, among other disorders. Preferably, the prosthesis 6500 includes living tissue or can accept ingrowth of existing tissue such that the prosthesis 6500 is eventually at least partially composed of a patient's own tissue. As such, prosthesis 6500 can be made by growing a patient's cells over a framework outside of the patient and later installed, and/or the growth of tissue can occur inside of the patient after installation. In another embodiment, prosthesis 6500 is synthetic only and does not include living tissue before or after installation. By way of further example, prosthesis 6500 can later be removed if another procedure is desired, including but not limited to installing a prosthesis similar to prosthesis 6500.

In some embodiments, percutaneous radio frequency mechanical placation can be performed to burn away a portion or all of the original valve leaflets, if desired, to enhance operation.

In accordance with further embodiments, systems and techniques are provided for delivering a prosthesis to a target location within a patient's lumenal system using temporary rails.

For purposes of illustration, and not limitation, and as depicted in FIGS. 66A, 66B, 67A, 68A, 68B, 69-73, systems and techniques are provided showing the use of temporary rails or tethers to help deliver a prosthesis to a target location with in a patient's anatomy by way of apical access. It is believed that such techniques provide enhanced security and safety, especially in dynamic environments, such as the heart, which are hard to visualize, even with motion compensating devices and imaging.

In accordance with the illustrated embodiment, loops that function as rails can be directed over a structural portion of a prosthesis (e.g., conduit or strut) and delivered to a target location. After the prosthesis is deployed and positioned in place, the rails or loops can be used to advance secondary devices to the site, such as clip appliers and the like to anchor the prosthesis in place. After advancing and deploying a secondary device or other devices, the rails/loops can be cut and removed from the patient.

As illustrated in FIG. 66A, the number of the rails/loops that are attached to the prosthesis can be as low as one on either side of the prosthesis, and can be practiced with respect to any prosthesis disclosed herein. Preferably, the loops are preloaded on the prosthesis, which can then be crimped and loaded onto a delivery catheter. Portions of the fixation system (e.g., anchor or retainer/clip delivery mechanisms) can be preloaded over the rails/loops, such as 2 to 3 cm away from the prosthesis annulus, as depicted in FIG. 66B.

FIGS. 67A a-b and c-d illustrate two different exemplary configurations of the fixation system portion of the delivery system. The fixation catheters have a central lumen that hold an anchor and can include an over the wire or rapid exchange structure for advancing the fixation catheters along the temporary loop rails. FIG. 68A illustrates exemplary prostheses and fixation systems for atrial delivery. While it is preferred that the fixation catheters are preloaded on the loop rails, it is similarly contemplated, as shown in FIG. 68B, to load them over the loop rails after the prosthesis is deployed.

FIG. 69 depicts a cross-section of an exemplary delivery system containing a crimped prosthesis and fixation catheters disposed over loop rails in a proximal region. The catheter includes a distal region portion that may include a guidewire port and one or more expandable members or balloons that permit perfusion when deployed. The inflatable member can be used to hold the prosthesis in place with respect to the delivery system when it is deployed to permit the fixation catheters to be used to attach the prosthesis to the anatomy.

Figure 71:
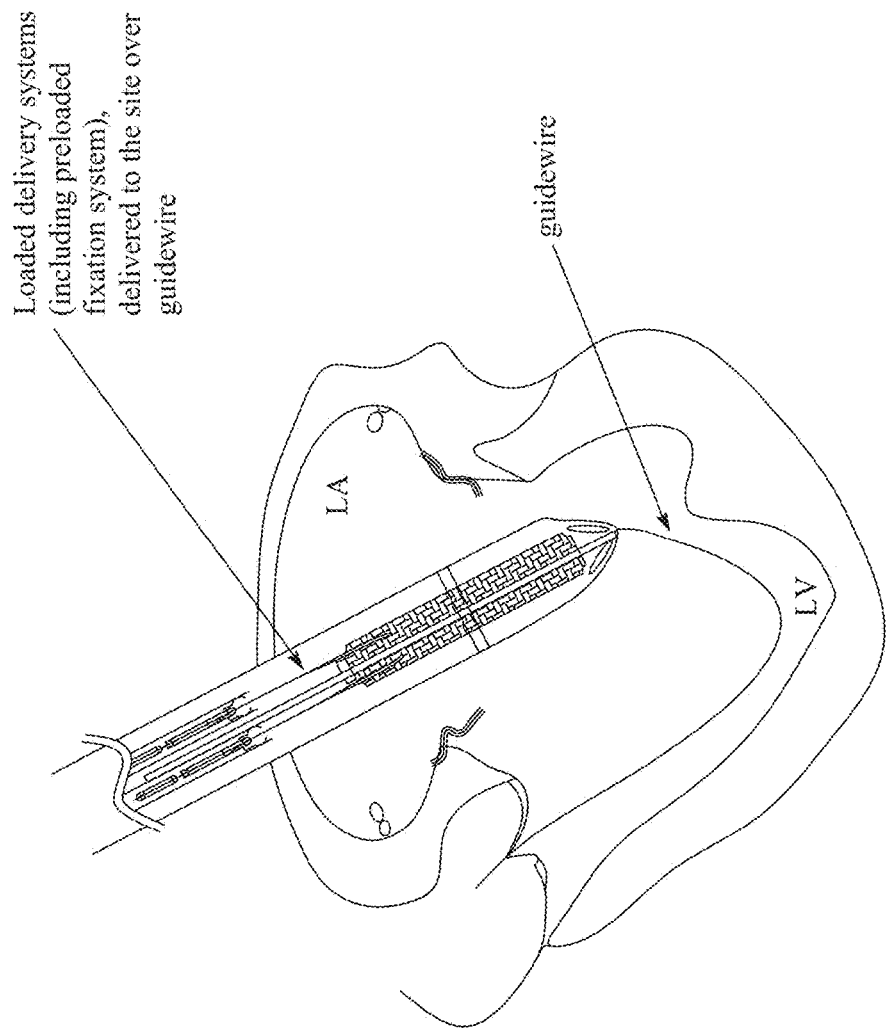

FIG. 70 illustrates the delivery system being advanced to the mitral valve by way of the left ventricle over a guidewire. The distal region of the delivery system is advanced through the mitral orifice and the prosthesis is deployed as illustrated in FIG. 72. Clips or anchors are applied by way of the fixation catheters. Finally, the temporary loops are removed from the patient, leaving the installed prosthesis in place. FIG. 71 illustrates a portion of an alternative method using an atrial approach.

Generally, the prosthesis should be held in place firmly, so the fixation catheters can be advanced to the prosthesis. In an apical access procedure (e.g., FIG. 71), holding and putting light tension in apex direction on the temporary loop rails can prevent the stent from being dislodged, while the fixation catheters are being advanced over the rails to a desired location above the annulus.

The structure of any prosthesis disclosed herein can include resorbable material such that the structures can be resorbed over time. Suitable materials for this purpose can include, for example, one or more of PLA (polylactic acid), PGA (polyglycolic acid), PLA/PGA (copolymers), PCL (polycaprolactone) and the like.

It will be appreciated that the delivery concepts herein using anchored rails have applicability in other procedures. For example, in an alternative embodiment, repair of an abdominal aortic aneurysm can be accomplished by advancing a prosthesis, such as a stent graft outfitted with one or more conduits for receiving the rails and, if desired one or more tethers for being tied to the one or more rails as defined herein. Precise placement of a stent graft can be very important when attempting to deposit a stent graft in the abdominal aorta as a number of arteries branch off from the aorta in this region. Thus, it is advantageous to not have the stent block these vessels. Anchors can be disposed in the vessel wall to provide the rail system in accordance with the description above and the stent graft or other prosthesis can be advanced to the target location and secured in place at the precise desired location. Similar techniques using a rail system can be used to deliver stent or stent graft structures with or without integral tethers at any desired location in a patient's anatomy.

While the delivery of a tethered or other stent or stent graft can take place in an artery or vein, the disclosed rail system can be used to deliver such prostheses into other lumenal systems in a patient. In accordance with one example, the disclosed delivery system can be used to deliver a stent or stent graft into the pulmonary system (e.g., bronchial passages) of a patient. The prosthesis can be loaded onto rails that have been previously installed in accordance with the above-described techniques and then advanced to a precise target location within the patient's lungs and secured in place.

By way of further example, the disclosed delivery system can be used to deliver a stent, stent graft or other prosthesis into the gastrointestinal tract of a patient. The prosthesis can be loaded onto rails that have been previously installed in accordance with the above-described techniques at a target location in the GI tract and then advanced to a precise target location within the patient's lungs and secured in place. For example, it may be necessary to implant a new stomach valve (synthetic or made of living tissue) in a patient or to install a stent or other structure in the bowels of a patient to maintain patency.

By way of further example, the disclosed delivery system can be used to deliver a stent, stent graft or other prosthesis (synthetic or made of living tissue) into the urinary system of a patient. The prosthesis can be loaded onto rails that have been previously installed in accordance with the above-described techniques at a target location, such as the urethra in the region of a partially resected prostate, and then advanced to a precise target location within the urethra and secured in place. By way of further example, a flared prosthesis could also be installed using premounted rails in the exit of the urinary bladder in order to maintain patency.

By way of further example, the disclosed delivery system can be used to deliver a stent, stent graft or other prosthesis (synthetic or made of living tissue) into the reproductive system of a patient. The prosthesis can be loaded onto rails that have been previously installed in accordance with the above-described techniques at a target location, such as the fallopian tube, and then advanced to a precise target location within the fallopian tube and secured in place.

In further accordance with the disclosure, an access port is provided herein having the physical attributes, for example, of the prosthesis of FIG. 1, but wherein the passage through the prosthesis includes an iris or other valve to permit passage of a surgical instrument therethrough. For example, such an instrument can be advanced and installed in an opening in the stomach wall for accessing the thoracic cavity or can be advanced and installed through the vagina to access portions of a patient's abdominal cavity.

One of ordinary skill in the art will appreciate that the present invention is not limited to the specific exemplary embodiments described herein. Many alterations and modifications may be made by those having ordinary skill in the art without departing from the spirit and scope of the invention. Therefore, it must be expressly understood that the illustrated embodiments have been shown only for the purposes of example and should not be taken as limiting the invention, which is defined by the following claims. These claims are to be read as including what they set forth literally and also those equivalent elements which are insubstantially different, even though not identical in other respects to what is shown and described in the above illustrations.

What is claimed is:

1. A prosthesis, comprising:
a) a graft material sleeve; and
b) a plurality of individual, physically separated, independently articulable, independent loops of shape memory wire material coupled to the graft material sleeve at a mid portion of each separate, independent loop such that the mid portions of the loops are spaced from and not directly attached to each other to enhance compliance of the prosthesis when installed in a native valve annulus, wherein:
the mid portion of each said separate, independent loop includes two substantially straight segments of the shape memory wire material;
each said separate, independent loop further includes a proximal portion including a first curved segment of the shape memory wire material connecting proximal ends of the two substantially straight wire segments of the mid portion; and
each said separate, independent loop includes a distal portion including a second curved segment of the shape memory wire material connecting distal ends of the two substantially straight wire segments of the mid portion, wherein the plurality of individual independently articulable loops are configured and arranged to be deployed in a lumenal system of a patient.

2. The prosthesis of claim 1, further comprising:
a) a conduit defining a passage therethrough coupled to and forming a part of the prosthesis; and
b) at least one tether extending through the passage of the conduit for controlling advancement of the prosthesis over and along the at least one tether to a target location.

3. A prosthesis delivery system, comprising:
a) a longitudinal body;
b) a prosthesis according to claim 2 disposed on the longitudinal body;
c) a retractable sheath covering the prosthesis; and
d) the conduit defined through the longitudinal body for housing the least one tether, the conduit having a proximal end and a distal end, the distal end being located proximate the prosthesis.

4. The prosthesis of claim 1, wherein the prosthesis does not include a valve and is configured to receive a separate implantable device.

5. An implant including the prosthesis of claim 4 and a replacement valve installed into a lumen defined by the prosthesis.

6. A valve prosthesis, comprising:
a graft material;
a plurality of individual, separated, parallel, independently articulable, primary, loops of shape memory wire material that are spaced from and not directly attached to each other, and are coupled to the graft material at a mid portion of each separate primary loop to enhance compliance of the prosthesis when installed in a native valve annulus, each of said separate, primary loops having a curved proximal end and a curved distal end, wherein:
the proximal ends of each of the separate, primary loops are independently articulable and configured to act as a first set of fasteners that extend radially and outwardly with respect to the graft material and the mid portion and are configured to attach the valve prosthesis to cardiac tissue on an atrial side of a posterior mitral annulus.

7. The valve prosthesis of claim 6, wherein the distal ends of each of the separate, primary loops are independently articulable and configured to act as a second set of fasteners that extend radially and outwardly from the graft material and are configured to attach the valve prosthesis to cardiac tissue on a ventricular side of the mitral annulus.

8. The valve prosthesis of claim 7, further comprising:
a third set of fasteners that extend radially outwardly with respect to the graft material and said mid portion of said plurality of separate, primary loops and are configured to attach the valve prosthesis to cardiac tissue at or above the mitral annulus, the third set of fasteners being of smaller overall dimension than the plurality of primary loops.

9. The valve prosthesis of claim 7, further comprising:
a set of independently articulable, separate, parallel, secondary, independent loops of shape memory wire material nested within and disposed radially and outwardly with respect to the primary loops, each of said separate, secondary loops having a curved proximal end and a curved distal end and a length that is less than the primary loops, wherein:
the proximal ends of each of the separate, secondary loops are independently articulable and configured to act as a third set of fasteners that extend radially and outwardly with respect to the graft material; and
the distal ends of each of the separate, secondary loops are independently articulable and configured to act as a fourth set of fasteners that extend radially and outwardly with respect to the graft material and are configured to attach the valve prosthesis to cardiac tissue on the ventricular side of the mitral annulus.

10. The valve prosthesis of claim 9, wherein the graft material includes a graft material sleeve, and the separate, secondary loops are coupled to the graft material sleeve at a mid portion of each of the separate, secondary loops.

* * * * *